US008440456B2

(12) United States Patent
Callewaert et al.

(10) Patent No.: US 8,440,456 B2
(45) Date of Patent: May 14, 2013

(54) **NUCLEIC ACIDS OF *PICHIA PASTORIS* AND USE THEREOF FOR RECOMBINANT PRODUCTION OF PROTEINS**

(75) Inventors: Nico Callewaert, Nevele-Hansbeke (BE); Kristof De Schutter, Nieuwerkerken (BE); Petra Tiels, Merelbeke (BE); Yao-Cheng Lin, Yuuijing Township, Tainan County (TW)

(73) Assignees: VIB, VZW, Zwijnaarde (BE); Universiteit Gent, Gent (BE); Research Corporation Technologies, Inc., Tucson, AZ (US)

( * ) Notice: Subject to any disclaimer, the term of this patent is extended or adjusted under 35 U.S.C. 154(b) by 236 days.

(21) Appl. No.: 12/785,286

(22) Filed: May 21, 2010

(65) Prior Publication Data

US 2011/0021378 A1 Jan. 27, 2011

Related U.S. Application Data

(60) Provisional application No. 61/180,502, filed on May 22, 2009.

(51) Int. Cl.
*C12N 15/00* (2006.01)
*C12N 1/19* (2006.01)

(52) U.S. Cl.
USPC .................................. 435/320.1; 435/254.23

(58) Field of Classification Search .................. None
See application file for complete search history.

(56) References Cited

U.S. PATENT DOCUMENTS 6,638,735 B1 10/2003 Rhee et al.
2009/0042264 A1 2/2009 Fatland-Bloom et al.

OTHER PUBLICATIONS

Inan et al., Biotechnol. Bioengineer. 93:771-778, 2005.*
International Search Report dated Aug. 25, 2010.

* cited by examiner

*Primary Examiner* — Nancy T Vogel
(74) *Attorney, Agent, or Firm* — Scully, Scott, Murphy & Presser, P.C.

(57) ABSTRACT

The present invention provides the genome sequence of *Pichia pastoris* and manually curated annotation of protein-coding genes. The invention provides novel nucleic acids, proteins, and related expression vectors useful for genetic engineering of methylotrophic yeast strains, as well as engineered methylotrophic yeast strains particularly *Pichia pastoris*, and use thereof for recombinant production of heterologous proteins including glycoproteins suitable for use in mammals including humans.

4 Claims, 11 Drawing Sheets

(7 of 11 Drawing Sheet(s) Filed in Color)

NUCLEIC ACIDS OF *PICHIA PASTORIS* AND USE THEREOF FOR RECOMBINANT PRODUCTION OF PROTEINS

CROSS REFERENCE TO RELATED APPLICATION

This application claims the benefit of priority from U.S. Provisional Application 61/180,502, filed May 22, 2009.

FIELD OF THE INVENTION

This invention relates generally to novel nucleic acids and recombinant expression technology. In particular, the invention relates to determination and assembly of the genome sequence of *Pichia pastoris*. The invention provides novel nucleic acids, proteins, and related expression vectors useful for genetic engineering of methylotrophic yeast strains, as well as engineered methylotrophic yeast strains particularly *Pichia pastoris* and use thereof for recombinant production of heterologous proteins.

BACKGROUND OF THE INVENTION

The methylotrophic yeast *Pichia pastoris* is by far the most often used yeast species in the production of recombinant proteins and is used in thousands of laboratories worldwide for the production of proteins for fundamental studies, as drug targets and for therapeutic use, and as a model for peroxisomal proliferation and methanol assimilation. The *P. pastoris* expression technology is available from Invitrogen (Carlsbad, Calif.) and from Research Corporation Technologies (Tucson, Ariz.), making it accessible for academic and commercial purposes alike. *P. pastoris* grows to high cell density, provides tightly controlled methanol-inducible transgene expression and efficiently secretes heterologous proteins in defined media. Indeed, several *P. pastoris*-produced biopharmaceuticals that are either not glycosylated (such as human serum albumin) or for which glycosylation is only needed for proper folding (such as several vaccines) are already on the market. *P. pastoris* strains with small, homogenous N-glycans have also been generated, which were then further engineered into human-type N-glycosylation[1,2]. Glyco-engineered products are now moving to clinical development[3]. Moreover, monoclonal antibodies can be made at gram per liter scale in glycosylation-homogeneous strains[4]. For further strain engineering, a better understanding of all aspects of the yeast's protein production machinery is desired, and a number of studies relating to *Pichia*'s secretory system and engineered promoters have been forthcoming[5,6]. However, although *P. pastoris* is widely used for protein production, relatively few genetic tools, engineered strains and data on the biology of this organism are available.

SUMMARY OF THE INVENTION

The present invention provides the determination, assembly and manually curated annotation of the 9.43 Mbp genomic sequence of the GS115 strain of *Pichia pastoris*.

In one embodiment, the invention provides isolated nucleic acid molecules that encode a protein as set forth in any one of SEQ0001-0025, 0027-0126, 0128-0165, 0172-0174, 0176-0200, or 0202-0212, or a protein substantially homologous thereto. In specific embodiments, the nucleic acid molecules contain the coding sequence of an ORF as set forth in any one of SEQ0001-0025, 0027-0126, 0128-0165, 0172-0174, 0176-0200, or 0202-0212, or contain a nucleotide sequence that is substantially homologous to the coding sequence of an ORF as set forth in any one of SEQ0001-0025, 0027-0126, 0128-0165, 0172-0174, 0176-0200, or 0202-0212.

In another embodiment, the present invention provides isolated proteins that have an amino acid sequence as set forth in any one of SEQ0001-0025, 0027-0126, 0128-0165, 0172-0174, 0176-0200, or 0202-0209, or an amino acid sequence substantially homologous thereto.

In still another embodiment, the present invention provides 53 peptides, shown in SEQ0001-0025 and 0027-0054, which are signal peptides of secreted proteins of *Pichia pastoris*. Nucleic acids that encode any of these signal peptides are also parts of the present invention.

In a further embodiment, the present invention provides a set of vectors useful for identification of the most effective choice of signal peptide for any given heterologous protein. Each vector contains a promoter and the coding sequence of one of the signal peptides identified in SEQ0001-0025 and 0027-0054, and a linker sequence or cloning site for inserting or receiving the coding sequence of the heterologous protein. In a specific embodiment, the linker sequence or cloning site simply includes a restriction endonuclease site. The heterologous coding sequence, with the same restriction site at its 5' end, can be joined to the signal peptide coding sequence via restriction enzyme digestion and subsequent ligation. In an alternative embodiment, the linker sequence is an intron sequence functional in *Pichia pastoris* and includes a restriction endonuclease site. The heterologous coding sequence, with the same intron sequence and restriction site at its 5' end, can be joined to the signal peptide coding sequence via the intron sequence. Transcription from the expression vector and subsequent RNA processing in a recipient cell lead to the generation of mRNAs without the intron, from which signal peptide-heterologous protein fusions are produced upon translation. A library of such fusion clones can be transformed into *Pichia pastoris* to select for the most effective choice of signal peptide for any given heterologous protein.

In one embodiment, the invention provides isolated nucleic acid molecules composed of a promoter sequence of any one of the *Pichia pastoris* genes set forth in SEQ0055-0165, 0169-0200, or 0202-0212.

Specific promoters of the present invention include those identified for SEQ0060-0085 (genes involved in glycolysis pathway), SEQ0096-0124 (genes showing high expression levels), SEQ0125-0128 (homologs of *S. cerevisiae* genes whose promoters are frequently used for recombinant expression), SEQ0169-0178 (methanol metabolism genes), and SEQ0202-0208 (genes involved in xylose, arabinose or threhalose metabolism). The promoters of these genes are located within the 1000 bp of the 5' region provided herein, and generally are located within the 500 bp immediately before the start codon of the gene, in some embodiments within 250 bp, 200 bp, 150 bp, 125 bp, 100 bp, 75 bp, 50 bp, 40 bp, or even 25 bp immediately before the start codon of the gene. In certain embodiments, the promoters include a TATA element identified herein in Table 6.

Use of any of the newly identified promoters for expression of a heterologous gene is encompassed by the present invention, including the related expression vectors and cells transformed with any such expression vectors.

In one embodiment, the present invention is directed to expression vectors and engineered methylotrophic yeast strains for increased expression (or overexpression) of one or more *Pichia* proteins involved in the secretory pathway, e.g., those as set forth in SEQ0055-0059, in order to achieve increased protein secretion.

In another embodiment, the present invention is directed to expression vectors and engineered methylotrophic yeast strains for overexpression of *Pichia* glycosylation precursor synthesis enzymes or transporters, e.g. UDP-Gal or UDP-GlcNAc transporters and UDP-Glc-4-epimerase for ER or Golgi localization. Such expression vectors are constructed to contain, from 5' to 3', a promoter functional in the recipient strain, operably linked to a coding sequence as set forth in any one of SEQ0129-0132, and a transcription termination sequence. The encoded protein is preferably also designed to include an ER or Golgi localization signal. Such an expression vector can be introduced into a methylotrophic yeast strain by transformation. Thus, the resulting engineered strains capable of increased expression of a protein encoded by any one of SEQ0129-0132 constitute another embodiment of the invention.

In a further embodiment, the present invention provides a methylotrophic yeast strain in which at least one (i.e., one or more) native gene encoding an O-mannosyl transferase or a beta-mannosyl transferase has been inactivated. In a specific embodiment, the strain is a *Pichia* strain, preferably, a *P. pastoris* strain. An O- or beta-mannosyl transferase knockout *P. pastoris* strain can be generated by inactivating at least one gene as set forth in SEQ0133-0137 or SEQ0210-0212, which can reduce or eliminate unwanted O- or beta-glycosylation of a heterologous protein.

In one embodiment, the present invention provides a methylotrophic yeast strain in which one or more native genes encoding enzymes involved in the ER glycosylation pathway have been inactivated. In a specific embodiment, the native yeast STT3 gene has been inactivated, and optionally the *Leishmania* STT3 gene has been introduced in place thereof. In another specific embodiment, the methylotrophic yeast strain is *P. pastoris* in which the native *Pichia* gene as set forth in SEQ0163 has been inactivated, and the *Leishmania* STT3 gene has been introduced in place thereof.

In another embodiment, the present invention is directed to methylotrophic yeast strains which overexpress one or more of the MNN4 homologs as set forth in SEQ0166-0168, and related expression vectors.

In still another embodiment, the present invention provides a protease-deficient methylotrophic yeast strain. In a specific embodiment, the strain is a *Pichia* strain, e.g., a *P. pastoris* strain. The protease-deficient *Pichia* strain can be generated by inactivating at least one (i.e., one or more) protease-encoding genes as set forth in SEQ0179 and SEQ0181-0186, such that there is no functional protease produced from a disrupted gene. Protease deficient strains allow more stable accumulation of heterologous proteins.

In yet another embodiment, the present invention provides a methylotrophic yeast strain engineered to overexpress a protease inhibitor protein, encoded by the gene set forth in SEQ0180, at an elevated level compared to an unmodified strain. In a specific embodiment, the strain is a *Pichia* strain, e.g., a *P. pastoris* strain. Expression vectors created for making such strains form another embodiment of the invention.

In one embodiment, the present invention is directed to expression vectors and engineered methylotrophic yeast strains for overexpression of at least one *Pichia* chaperones involved in secreted protein folding in the ER. Such expression vectors are constructed to contain, from 5' to 3', a promoter functional in the recipient strain, operably linked to a coding sequence as set forth in any one of SEQ0187-SEQ0200, and a transcription termination sequence. Such an expression vector can be introduced into a methylotrophic yeast strain by transformation. Another embodiment of the invention is directed to engineered methylotrophic yeast strains capable of overexpressing a protein encoded by any one of SEQ0187-SEQ0200. In still another embodiment, methylotrophic yeast strains capable of overexpressing a combination of multiple chaperones are provided, which combination can be selected as most effective for recombination production of a particular heterologous protein.

In a further embodiment, the present invention provides an isolated nucleic acid molecule containing the nucleotide sequence as set forth in SEQ0200, which encodes the 5S rRNA. Use of this nucleic acid in creating vectors to achieve multi-copy integration of a heterologous gene and generate strains having a heterologous gene stably integrated in the genome in multiple copies is also contemplated by the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
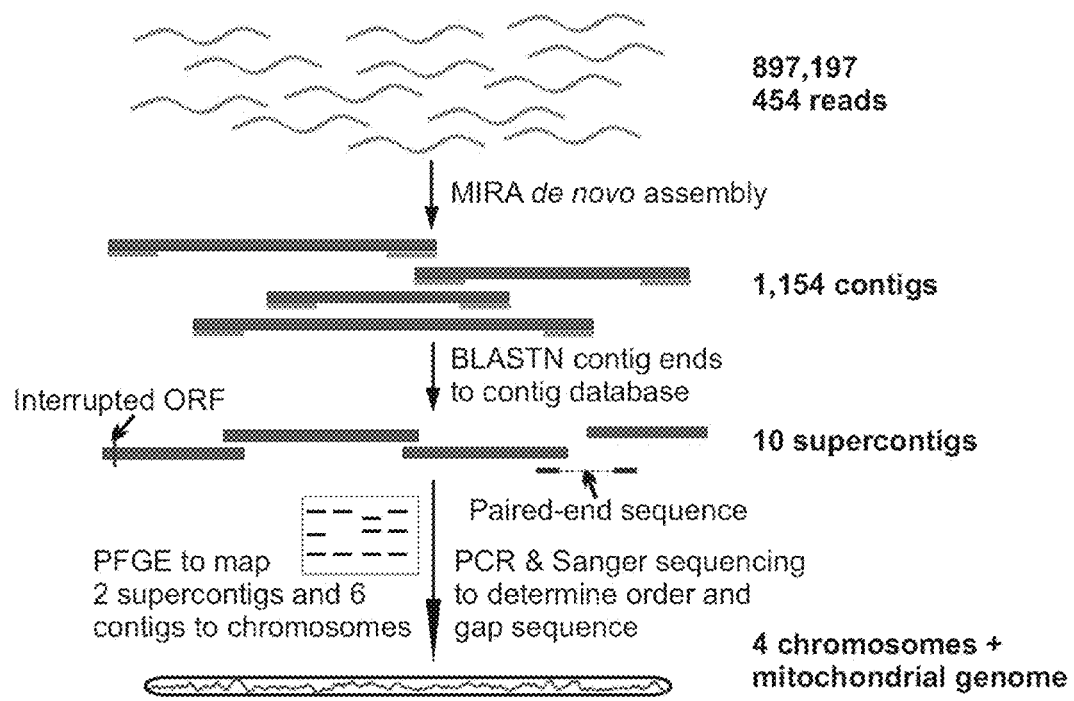
FIGS. 1A-1C. *Pichia pastoris* genome sequencing and overview. 1A. Genome sequencing and assembly strategy. 1B. *P. pastoris* chromosomes and known markers position. Genes that had been previously mapped to the chromosomes through PFGE are indicated in blue, and rDNA repeats in yellow, the 5S rRNA are indicated in yellow with the red arrow. 1C. Phylogenetic tree. The phylogenetic tree was built on the concatenated sequence of 200 single-copy ortholog genes in all of the 6 species. Numbers next to each branch correspond to the number of Pfam domains uniquely present in the corresponding lineage.

The present inventors have determined and assembled the 9.43 Mbp genomic sequence of the GS115 strain of *P. pastoris*, and manually curated annotation of 5,313 protein-coding genes. On this basis, the invention provides novel protein-encoding genes from *Pichia pastoris*, including identification of the 5' upstream region (including promoter), open reading frame (ORF) and 3' downstream region of these genes. The present invention also provides novel *Pichia pastoris* proteins, and certain signal peptides of some of these *P. pastoris* proteins. The nucleic acids and encoded proteins identified herein, as well as the promoters and signal peptides, can be used in engineering methylotrophic yeast strains, particularly *Pichia* strains, for recombinant production of proteins, including but not limited to glycoproteins having glycoforms suitable for therapeutic use in mammals especially humans. In addition to the values and utilities provided by each of the novel molecules individually, the determination and annotation of the genome sequence of *Pichia pastoris* also permit a more complete, overall understanding of *Pichia pastoris* in respect to its protein modification and secretion system as well as methanol metabolism, by providing a complete set of *Pichia pastoris* genes coding for enzymes involved in methanol assimilation, a complete catalog of *Pichia pastoris* orthologs to the *S. cerevisiae* endoplasmic reticulum (ER) folding machinery, and a full collection of genes involved in the ER glycosylation pathway of *Pichia pastoris*. These findings of the present invention enable more efficacious overall design and engineering for recombinant production of heterologous proteins in methylotrophic yeasts.

The various aspects and embodiments of the present invention are described in details below.

General Definitions:

Open Reading Frame (ORF)—An ORF refers to the portion of a gene that begins with the start codon and ends with a stop codon and that encodes a protein. An ORF may include one or more intron sequences.

Coding sequence—This term is used herein to refer to a contiguous sequence of codons of the protein encoded by the ORF and does not include intron.

5' upstream region—This term (or "5' region" or "upstream region" in abbreviation) is used herein to refer to the genomic region 5' relative to the ORF of a gene. Generally speaking, the Sequence file provided herein has set forth a 5' upstream region of approximately 1000 nucleotides, which, in some cases, includes the start and/or stop codons of the previous gene. The 5' upstream region of a gene includes the promoter of the gene. The extent of the 5' region provided herein for each gene is sufficient for targeting recombination to this site, e.g. to delete the entire ORF when used in combination with the 3' downstream region sequence, or to insert a different regulatory region or promoter immediately upstream of the ORF when used in combination with the ORF sequence itself.

Promoter—This term refers to a portion of the 5' upstream region of a gene that directs the transcription of the gene. Promoters are located within the 1000 bp of the 5' upstream region of yeast genes, with a "TATA box" sequence most commonly located at 10-120 bp upstream from the start codon of a gene. A "TATA box" is a DNA sequence (cis-regulatory element) found in the promoter region, and has the core DNA sequence 5'-TATAAA-3' or a variant. A TATA box is usually located 25 base pairs upstream to the transcription site. In about 76% percent of the *Pichia pastoris* genes, at least one of the following TATA-elements has been located—TATAA: 50% of the elements are found 60 to 90 bp upstream of ATG (75% 40 to 110 bp upstream of ATG); TACAA: 78% of the elements are found 50 to 70 bp upstream of ATG; TATA: 50% of the elements are found 10 to 40 bp upstream of ATG; TATATA: 50% of the elements are found 80 to 90 bp upstream of ATG; and TATATATA: 50% of the elements are found 50 to 60 bp of ATG. Details of the TATA boxes of the promoters provided by the present invention are set forth in Table 6. Accordingly, in certain specific embodiments, the promoter of a *Pichia pastoris* gene provided herein is located within the 500 bp immediately before the start codon of the gene; prepferably within 250 bp, 200 bp, 150 bp, 125 bp, 100 bp, 75 bp, 50 bp, 40 bp, or even 25 bp immediately before the start codon of the gene; and in particular embodiments, the promoter includes a TATA element identified herein in Table 6. The precise location and composition of a promoter can be determined by using well known techniques including deletion mapping and site-directed mutagenesis, as further described below.

3' downstream region—This term (sometimes "downstream region" or "3' region" in abbreviation) is used herein to refer to the genomic region 3' relative to the ORF of a gene. Generally speaking, the Sequence file provided herein has set forth a 3' downstream region of approximately 1000 nucleotides, which, in some cases, includes the start and/or stop codons of the next gene. The 3' down region of a gene includes the transcription termination sequence (or 3' termination sequence) of the gene. The extent of the 3' region provided herein is sufficient to target recombination to this site in the chromosome.

Selectable marker—This term refers either to a dominant drug resistance marker or similar dominant marker, or to a more limited prototrphic selection such as HIS, applicable to a host that is defective for the key enzyme supplied by a selectable marker gene.

"Signal peptide" and "mature proteins"—The term "signal peptide" or "signal sequence" refers to the short peptide sequence within a protein precursor synthesized in the cytoplasm that targets the precursor form to the endoplasmic reticulum. Signal peptides are typically cleaved from the precursor form by signal peptidase after the proteins are transported to the ER, and the resulting proteins move along the secretory pathway to their intracellular or extracellular location. For some proteins, cleavage of the signal peptide results in the mature form (i.e., the final, biologically active form) of the protein, while for other proteins, additional proteolytic processing may be required in order to generate the mature form of the protein.

Substantially homologous amino acid sequences—When two or more amino acid sequences are said to be substantially homologous, it is meant that the sequences share a significant degree of similarity, for example, at least 85%, 90%, 95%, 98% or even 99% similarity. The degree of similarity can be determined, for example, as the index calculated using the BLAST or the Lipman-Pearson Protein Alignment program with the following choice of parameters for the latter program: Ktuple=2, Gap Penalty=4, and Gap Length Penalty=12. The term "similarity" includes identity. Substantially homologous proteins can perform or possess substantially the same function; i.e., the enzymatic activities of the proteins differ by not more than 20%, 15%, 10%, or even 5% under a same set of conditions applicable for measuring enzymatic activity. A protein that is substantially homologous to a *Pichia pastoris* protein identified herein is, in some embodiments, a protein of methylotrophic yeast; for example, a protein of *Pichia*.

Substantially homologous nucleotide sequences—When two or more nucleotide sequences are said to be substantially homologous, it is meant that the sequences share a significant degree of identity, for example, at least 85%, 90%, 95%, 98% or even 99% identity. The degree of homology is also reflected by hybridization characteristics. As defined herein, a first nucleic acid sequence that is substantially homologous to a second nucleic acid sequence molecule also hybridizes to the complement of the second nucleic acid sequence under high stringency conditions. "High stringency conditions", as defined herein, include, for example, hybridization at 42° C. in 50% v/v formamide, 1M NaCl, and 1% w/v SDS, and washing at 65° C. in 0.1-2×SSC (e.g., 0.1, 0.2, 0.5, 1 or 2×SCC) and 1% w/v SDS. A nucleic acid that is substantially homologous to a *Pichia pastoris* nucleic acid identified herein is, in some embodiments, a nucleic acid of methylotrophic yeast; for example, a nucleic acid of *Pichia*.

"Heterologous" versus "native"/"endogenous"—The term "heterologous" is used herein in several different contexts to reflect the fact that a molecule is placed in a genetic, molecular or cellular environment that is different than its native environment. For example, when the promoter of a gene is being utilized to drive the expression of a different gene, the promoter will be taken out of its native genetic context and placed in an operable linkage to a heterologous gene. As another example, the signal peptide of a protein can be used to direct the localization of a different protein, i.e., a heterologous protein. Additionally, a methylotrophic yeast strain such as *Pichia* can be transformed with a heterologous nucleic acid, i.e., a nucleic acid which the non-engineered *Pichia* strain does not have. The resulting engineered strain will express the protein encoded by the heterologous nucleic acid, i.e., a heterologous protein.

Gene overexpression—Overexpression of a gene in a methylotrophic yeast is achieved by genetic modification of the yeast such that the expression of the gene is increased (measurable either at the mRNA level or the protein level), as compared to the unmodified yeast. The extent of increase in expression is at least 35%, or at least 50%, or preferably at least 150%, 200%, 250%, 300%, 400% or more. Overexpression of a gene can be achieved by introducing additional expression cassette carrying the gene (as a plasmid vector or integrated into the chromosome), or by replacing the native promoter of the gene with a stronger constitutive or inducible promoter.

Gene inactivation—Inactivation of a gene in a methylotrophic yeast is achieved by genentic modification of the yeast such that substantially no functional protein is produced from the strain, By "substantially", it is meant that the level of functional protein produced from the modified strain is not more than 20%, or 15%, or 10% or even 5% or less of the level of functional protein produced from an unmodified strain. Inactivation of a gene can be achieved by disrupting the genomic ORF of the gene in the strain, or disrupting the native promoter, or replacing the native promoter with a repressible promoter (e.g., repressible by methanol).

Methylotrophic yeast—Methylotrophic yeasts are those capable of growth on methanol, and include yeasts of the genera *Candida*, *Hansenula* (such as *H. polymorpha*, now classified as *Pichia angusta*), *Torulopsis*, and *Pichia* (e.g., *Pichia pastoris*, *Pichia methanolica*, *Pichia angusta* (formerly *Hansenula polymorpha*), *Pichia stipitis*, and *Pichia anomala*).

Chaperones—Chaperones are proteins that assist in the non-covalent folding or unfolding of proteins, mediate the redox potential to assist the formation of disulphide bonds within or between protein subunits, assist in the assembly or disassembly of other macromolecular structures or complexes, and/or translocation of proteins across membranes.

For convenience of discussion, the novel protein-encoding genes identified by the present invention have been grouped based on the functions of the encode proteins and are discussed in details below. Where the utility of a particular group or a particular gene is not specifically discussed, its utilities are apparent based on the function and utility of its homologs) from other yeast species such as *S. cerevisiae* which have been characterized.

Secreted Proteins with a Signal Peptide

In accordance with the present invention, 53 genes have been identified as encoding secreted proteins with a signal peptide. In the annotated Sequence file provided herein, the ORF and the amino acid sequence (with the signal peptide portion shown in bold) of each of the 53 genes are set forth in SEQ0001-0025 and 0027-0054.

In one embodiment, the present invention is directed to isolated nucleic acid molecules comprising a nucleotide sequence that encodes a protein (e.g., a full-length protein) as set forth in any of SEQ0001-0025 or 0027-0054, or encodes a protein that is substantially homologous to a full-length protein as set forth in any of SEQ0001-0025 or 0027-0054.

In a specific embodiment, the present invention is directed to isolated nucleic acid molecules comprising the coding sequence of an ORF as set forth in any of SEQ0001-0025 or 0027-0054, or a nucleotide sequence that is substantially homologous to the coding sequence of an ORF as set forth in any of SEQ0001-0025 or 0027-0054.

In another embodiment, the invention is drawn to an isolated protein comprising an amino acid sequence (e.g., a full-length protein sequence) as set forth in any of SEQ0001-0025 or 0027-0054, or an amino acid sequence substantially homologous thereto.

Figure 7:
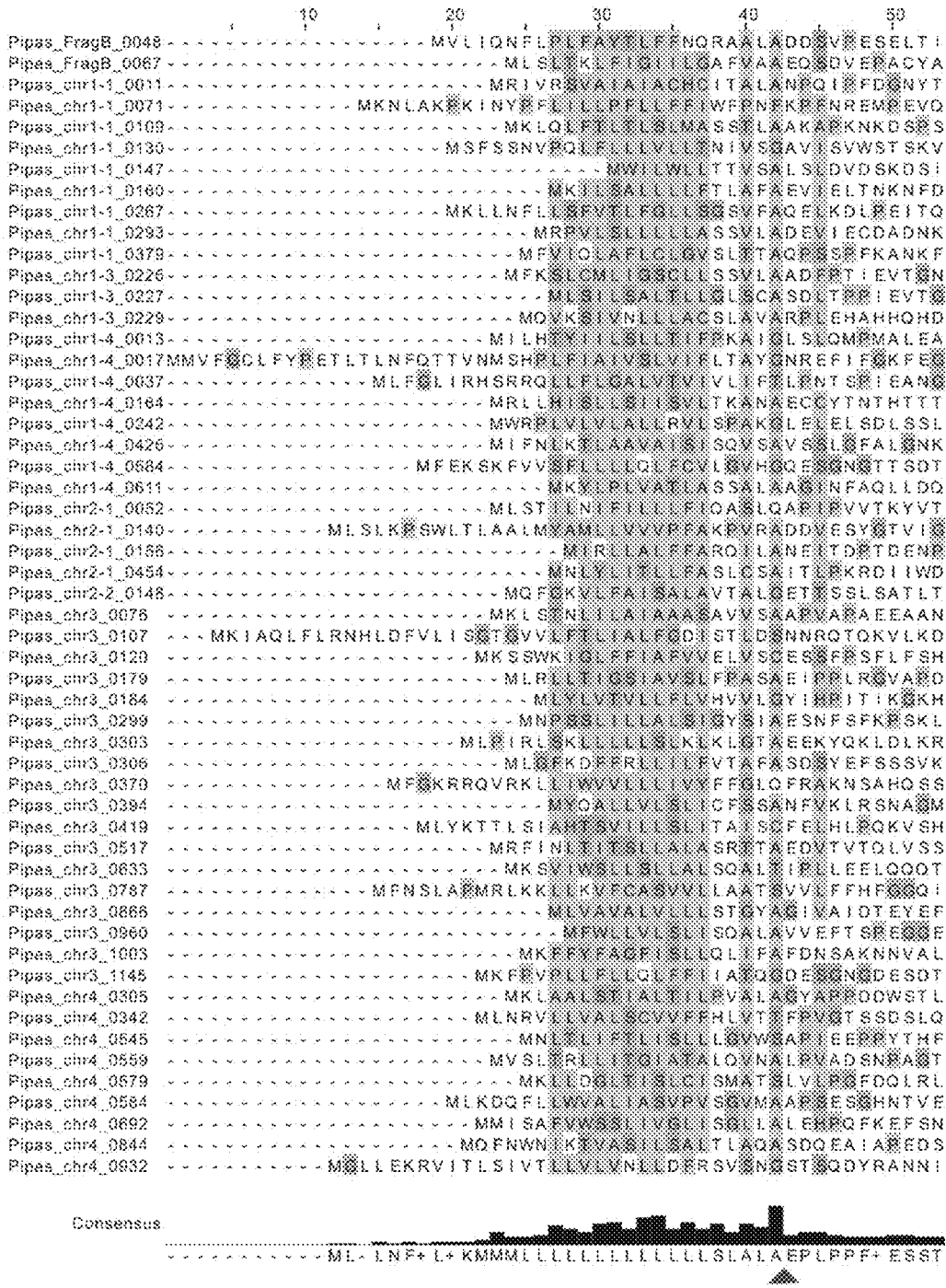
FIG. 7. *P. pastoris* secretion signals (SEQ ID NOS: 781-834, respectively, in order of appearance). 53 SignalP predicted signal peptides were manually curated to be secretion signals based on the function of orthologs. The predicted site of signal peptidase cleavage is indicated by the red triangle. Alignment of these peptides shows a hydrophobic consensus sequence (poly Leu) (SEQ ID NO: 835), and a small amino acid residue at position −1 and −3 from the cleavage site.

In still another embodiment, the invention is directed to the signal peptides of these 53 newly identified genes and uses thereof for recombinant expression of heterologous proteins. These signal peptides are summarized and aligned in FIG. 7. Alignment of these peptides shows a hydrophobic consensus sequence (poly Leu), and a small amino acid residue (such as A, C, G and S) at position −1 and −3 from the cleavage site.

Proteins destined for translocation into the endoplasmic reticulum carry a signal peptide that is recognized upon ribosomal translation by the signal recognition particle, which docks to the translocon, upon which translation continues and the protein is delivered into the ER lumen. The signal peptide is removed by signal peptidase.

When over-expressing a protein destined for secretion, one can either use the protein's native signal peptide if the translocation and signal peptidase machinery of the host cell can efficiently recognize and then process it. Alternatively, the coding sequence of a heterologous signal peptide can be fused to the coding sequence for the mature form of the protein. In *Pichia pastoris*, the signal sequence which has been frequently used is the prepro signal of *S. cerevisiae* alpha mating factor. Whereas this signal works in many cases, processing of the propeptide can be problematic as it requires Kex2p protease cleavage followed by polishing of the newly created N-terminus by Ste13p diaminopeptidase. Therefore, having a large library of *Pichia* signal peptides available is particularly useful. For example, one can screen for effective signal peptide(s) for a given protein desired to be expressed in *Pichia*. In addition, based on the library of signal peptides provided herein, a consensus artificial signal peptide can be designed which can be used to efficiently secrete multiple different heterologous proteins.

To screen the library for a suitable *Pichia* signal peptide for a given target protein desired to be expressed in *Pichia*, an intron functional in *Pichia* (which can be selected from those shown in the Sequence File provided herein) can be cloned before the ORF or coding sequence for the target protein, wherein the intron contains either a unique restriction site or a recognition site for a recombinase. The same intron can be cloned behind (i.e., 3' of) each signal peptide coding sequence in the library, enabling rapid generation of an expression library of signal peptide-target ORF fusions through classical cloning using the unique restriction site or through recombinational cloning. Upon transcription, the intron is removed by the *Pichia* splicing machinery, resulting in an expressed library of in-frame fusion between the coding sequence for one of the signal peptides and the target ORF.

Subsequently, secretion of the target protein by individual members of the expressed library can be evaluated by a suitable technique such as SDS-PAGE analysis, coomassie blue staining, or Western blot. In this way, the suitability of a given *Pichia* signal peptide can be evaluated for secretion of any target protein.

Accordingly, in another embodiment, the present invention is directed to a library of expression vectors, wherein each of the 54 signal peptides is represented in the library. Each expression vector contains, from 5' to 3', a promoter functional in *Pichia*, operably linked to a coding sequence for a signal peptide, and an intron sequence containing a restriction endonuclease recognition site. The expression vector is designed to accommodate insertion of the coding sequence of a target protein, linked in its 5' to the same intron sequence containing the same restriction endonuclease recognition site on the expression vector.

In a further embodiment, the present invention provides an expression vector capable of directing the expression and secretion of a heterologous protein in *Pichia pastoris* or another methylotrophic yeast. The expression vector contains, from 5' to 3', a promoter functional in the recipient strain, operably linked to a coding sequence for the fusion of a signal peptide (identified in SEQ0001-0025 and 0027-0054) and the heterologous protein. Host cells transformed with such an expression vector constitute another embodiment of the present invention.

In another embodiment, the signal sequences from some of the secreted proteins are not cleaved off in the ER, but remain linked to the protein. This is usual for a number of those enzymes involved in the glycosylation pathway (for example those for mannosyl transferases), for secretion chaperones, and for other factors that help secretion in a particular compartment, for example. These signal sequences are useful for the localization of heterologous proteins to target them to particular compartments of the secretory pathway, which may be advantageous to various aspects of posttranslational modification. This may correspond to the same or equivalent compartment in which a heterologous enzyme or protein normally acts in its native cell. Alternatively, it may be a different compartment, but, is effective because it is the same as that in which another enzyme acts or is immediately downstream or upstream of the compartment in which a second enzyme acts, effectively channeling and coordinating the sequence of a metabolic process.

Proteins Potentially Involved in Secretion

In accordance with the present invention, 5 genes have been identified as encoding proteins potentially involved in secretion, including *P. pastoris* homologs of *S. cerevisiae* SEC1, SEC 11, and subunits SPC1, SPC2 and SPC3 of signal peptidase complex. In the annotated Sequence file provided herein, the nucleotide sequences of the 5' upstream region (including promoter), the ORF, and the 3' downstream region, as well as the amino acid sequence, of each of these 5 genes are set forth in SEQ0055 to SEQ0059.

In one embodiment, the present invention is directed to isolated nucleic acid molecules comprising a nucleotide sequence that encodes a protein (e.g., a full-length protein) as set forth in any of SEQ0055 to SEQ0059, or encodes a protein that is substantially homologous to a full-length protein as set forth in any of SEQ0055 to SEQ0059.

In a specific embodiment, the present invention is directed to isolated nucleic acid molecules comprising the coding sequence sequence of an ORF as set forth in any of SEQ0055 to SEQ0059, or a nucleotide sequence that is substantially homologous to the coding sequence of an ORF as set forth in any of SEQ0055 to SEQ0059.

In another embodiment, the invention is drawn to an isolated protein comprising an amino acid sequence (e.g., a full-length protein sequence) as set forth in any of SEQ0055 to SEQ0059, or an amino acid sequence substantially homologous thereto.

In one embodiment, the invention is directed to a methylotrophic yeast strain, for example a *Pichia* strain such as *Pichia pastoris*, which overexpresses the *Pichia pastoris* SEC1 gene as set forth in SEQ0055. Expression vectors for achieving such overexpression are also contemplated by the present invention.

Analysis of mutants of *S. cerevisiae* shows SEC1 to be required for the SNARE mediated docking and fusion of exocytic vesicles. Therefore, overexpression of the native SEC1 gene in *P. pastoris* may facilitate the exocytosis of secretory vesicles. The coding sequence of the *P. pastoris* SEC1 gene can be cloned into an expression vector and is introduced into a methylotrophic yeasr strain. To evaluate whether secretion levels are increased as a result of such overexpression, the quantity of secreted (glyco)proteins per cell can be analyzed.

In another embodiment, the invention is directed to a methylotrophic yeast strain, for example a *Pichia* strain such as *Pichia pastoris*, which overexpresses at least one of the *Pichia pastoris* SEC11, SPC1, SPC2 or SPC3 genes as set forth in SEQ0056-0059. Expression vectors for achieving such overexpression are also provided by the present invention.

Efficient processing of the signal peptide of a secreted protein is essential for high yield and to eliminate the presence of additional amino acids in the secreted protein. Overexpression of one or more subunits of the signal peptidase complex may increase the efficiency and the quality of the processing. To evaluate whether the efficiency of the signal peptide cleavage is improved as a result of overexpression of a subunit of signal peptidase complex, the quantity and the amino acid sequence of a heterologous secreted glycoproteins can be analyzed.

*P. Pastoris* Homologues of Genes Involved in the Glycolysis Pathway

In accordance with the present invention, 26 genes have been identified as encoding proteins involved in the glycolysis pathway. In the annotated Sequence file provided herein, the nucleotide sequences of the 5' upstream region (including promoter), the ORF and the 3' downstream region, as well as the amino acid sequence, of each of these 26 genes are set forth in SEQ0060 to SEQ0085.

In one embodiment, the present invention is directed to isolated nucleic acid molecules comprising a nucleotide sequence that encodes a protein (e.g., a full-length protein) as set forth in any of SEQ0060 to SEQ0085, or encodes a protein that is substantially homologous to a full-length protein as set forth in any of SEQ0060 to SEQ0085.

In a specific embodiment, the present invention is directed to isolated nucleic acid molecules comprising the coding sequence of an ORF as set forth in any of SEQ0060 to SEQ0085, or a nucleotide sequence that is substantially homologous thereto.

In another embodiment, the invention is drawn to an isolated protein comprising an amino acid sequence (e.g., a full-length protein sequence) as set forth in any of SEQ0060 to SEQ0085, or an amino acid sequence substantially homologous thereto.

In a further embodiment, the present invention is directed to the promoters of each of the genes as set forth in SEQ0060 to SEQ0085. Because glycolysis is a central metabolic pathway, the promoters of the genes encoding proteins involved in this pathway are believed to be strong promoters, which can be used for driving overexpression of heterologous genes in methylotrophic yeast such as *P. pastoris*. Accordingly, the present invention provides expression vectors containing any one of the promoters of the genes set forth in SEQ0060 to SEQ0085, operably linked to the coding sequence of a heterologous protein. Methylotrophic yeast strains transformed with such an expression vector are also provided by the invention.

*P. Pastoris* Homologues of Genes Involved in Homologous Recombination

In accordance with the present invention, 10 genes have been identified as encoding proteins involved in the homologous recombination. In the annotated Sequence file provided herein, the nucleotide sequences of the 5' upstream region (including promoter), the ORF and the 3' downstream region, as well as the amino acid sequence, of each of these 10 genes are set forth in SEQ0086 to SEQ0095.

In one embodiment, the present invention is directed to isolated nucleic acid molecules comprising a nucleotide sequence that encodes a protein (e.g., a full-length protein) as set forth in any of SEQ0086 to SEQ0095, or encodes a protein that is substantially homologous to a full-length protein as set forth in any of SEQ0086 to SEQ0095.

In a specific embodiment, the present invention is directed to isolated nucleic acid molecules comprising the coding sequence of an ORF as set forth in any of SEQ0086 to SEQ0095, or a nucleotide sequence that is substantially homologous thereto.

In another embodiment, the invention is drawn to an isolated protein comprising an amino acid sequence (e.g., a full-length protein sequence) as set forth in any of SEQ0086 to SEQ0095, or an amino acid sequence substantially homologous thereto.

In a further embodiment, the invention is directed to methylotrophic yeast strains, especially *Pichia pastoris* strains, wherein one or more of the genes as set forth in SEQ0086 to SEQ0095 have been inactivated. Inactivation of these genes involved in recombination may prevent out-recombination of an expression unit or cassette containing a heterologous gene integrated in the chromosome, therefore potentially "lock" or stabilize the insertion, especially multicopy insertions as further discussed hereinbelow.

Genes with High Expression Levels

In accordance with the present invention, 29 genes have been identified as encoding proteins and showing expression levels 20× higher than GAP1 based on microarray analysis. In the annotated Sequence file provided herein, the nucleotide sequences of the 5' upstream region (including promoter), the ORF and the 3' downstream region, as well as the amino acid sequence, of each of these 10 genes are set forth in SEQ0096 to SEQ0124.

In one embodiment, the present invention is directed to isolated nucleic acid molecules comprising a nucleotide sequence that encodes a protein (e.g., a full-length protein) as set forth in any of SEQ0096 to SEQ0124, or encodes a protein that is substantially homologous to a full-length protein as set forth in any of SEQ0096 to SEQ0124.

In a specific embodiment, the present invention is directed to isolated nucleic acid molecules comprising the coding sequence of an ORF as set forth in any of SEQ0096 to SEQ0124, or a nucleotide sequence that is substantially homologous thereto.

In another embodiment, the invention is drawn to an isolated protein comprising an amino acid sequence (e.g., a full-length protein sequence) as set forth in any of SEQ0096 to SEQ0124, or an amino acid sequence substantially homologous thereto.

In a further embodiment, the present invention is directed to the promoters of each of these 29 genes showing high expression levels. These promoters can be used for driving overexpression of heterologous genes in methylotrophic yeast such as *P. pastoris*. Accordingly, the present invention provides expression vectors containing any one of the promoters of the 29 genes set forth in SEQ0096 to SEQ0124, operably linked to the coding sequence of a heterologous protein. Methylotrophic yeast strains transformed with such an expression vector are also provided by the invention.

Homologs of Promoters Used for Expression of Proteins in *S. Cerevisiae*

In accordance with the present invention, 4 genes have been identified as encoding *P. pastoris* protein homologs of *S. cerevisiae* whose promoters have been used for recombinant expression in *S. cerevisiae*, including SEQ0125 (homolog of *S. cerevisiae* glycerol-3-phosphate dehydrogenase 1 (GPD1) and GPD2), SEQ0126 (homolog of *S. cerevisiae* alcohol dehydrogenase 1 (ADH1) and ADH2), SEQ0127 (homolog of *S. cerevisiae* PHO5, although partial promoter and the ORF of the *Pichia pastoris* gene have been reported in the art), an SEQ0128 (homolog of *S. cerevisiae* sulfite reductase beta subunit ECM17). In the annotated Sequence file provided herein, the nucleotide sequences of the 5' upstream region (including promoter), the ORF and the 3' downstream region, as well as the amino acid sequence, of each of these 4 genes are set forth in SEQ0125 to SEQ0128.

In one embodiment, the present invention is directed to isolated nucleic acid molecules comprising a nucleotide sequence that encodes a protein (e.g., a full-length protein) as set forth in any of SEQ0125, SEQ0126 or SEQ0128, or encodes a protein that is substantially homologous to a full-length protein as set forth in any of SEQ0125, SEQ0126 or SEQ0128.

In a specific embodiment, the present invention is directed to isolated nucleic acid molecules comprising the coding sequence of an ORF as set forth in any of SEQ0125, SEQ0126 or SEQ0128, or a nucleotide sequence that is substantially homologous thereto.

In another embodiment, the invention is drawn to an isolated protein comprising an amino acid sequence (e.g., a full-length protein sequence) as set forth in any of SEQ0125, SEQ0126 or SEQ0128, or an amino acid sequence substantially homologous thereto.

In a further embodiment, the present invention is directed to the promoters of each of these 4 genes. These promoters can be used for driving expression of heterologous genes in *Pichia pastoris* or another methylotrophic yeast species. Expression vectors containing any of these promoters, operably linked to a heterologous coding sequence, and methylotrophic yeast strains transformed with any such expression vectors, are contemplated by the invention.

Genes Involved in Nucleotide Sugar Synthesis and Transport

In accordance with the present invention, 4 genes have been identified as encoding proteins involved in nucleotide sugar synthesis and transport, including UDP-GlcNAc transporter (SEQ0129), UDP-glucose-4-epimerase (SEQ0130), HUT1 (putative role of transporting UDP-galactose into Golgi) (SEQ0131), and a putative UDP-galactose transporter (SEQ0132). In the annotated Sequence file provided herein, the nucleotide sequences of the 5' upstream region (including promoter), the ORF and the 3' downstream region, as well as the amino acid sequence, of each of these 4 genes are set forth in SEQ0129 to SEQ0132.

Figure 3A:
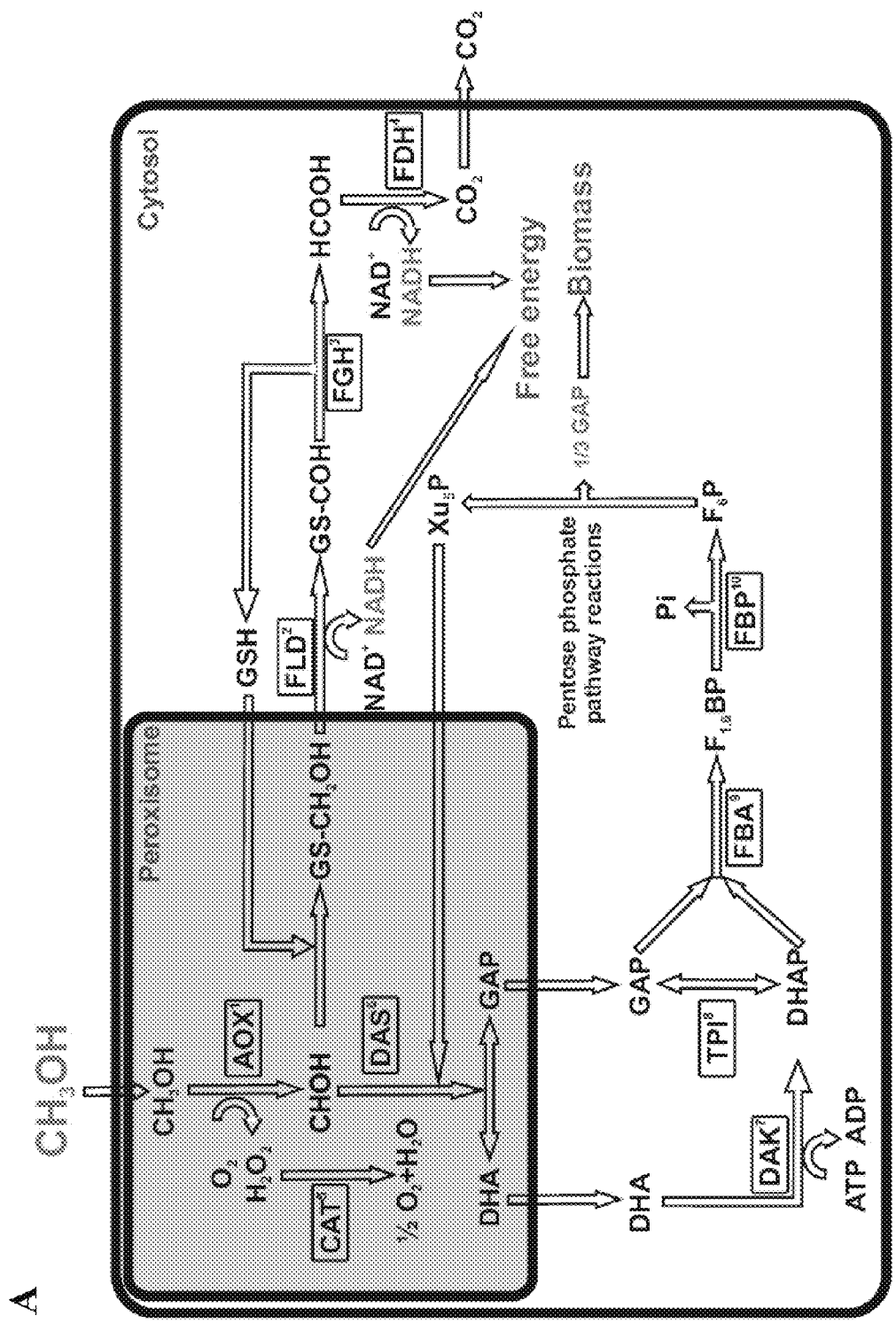
FIGS. 3A-3B. *Pichia pastoris* pathways. 3A. Methanol utilisation pathway in *Pichia pastoris*. A detailed table with the genes coding for the respective enzymes is shown in Table 5A. Abbreviations: [1]AOX: alcohol oxidase, [2]FLD: formaldehyde dehydrogenase, [3]FGH: S-formylglutathione hydrolase, [4]FDH: formate dehydrogenase, [5]CAT: catalase, [6]DAS: dihydroxyacetone synthase, [7]DAK: dihydroxyacetone kinase, [8]TPI: triosephosphate isomerase, [9]FBA: fructose-1,6-bisphosphate aldolase, [10]FBP: fructose-1,6-bisphosphatase; DHA: dihydroxyacetone, GAP: glyceraldehyde-3-phosphate, DHAP: dihydroxyacetone phosphate, $F_{1,6}BP$: fructose-1,6-bisphosphate, $F_6P$: fructose-6-phosphate, $P_i$: phosphate, $Xu_5P$: xylulose-5-phosphate, GSH: glutathione. 3B. Protein secretion pathway. Schematic representation of the secretion pathway in *P. pastoris*. A detailed table with the genes coding for the components involved in the represented complexes or processes is shown in Table 5B. The nascent protein is translocated to the ER by the Sec61 complex and N-glycosylation sites are glycosylated with the dolichol-linked $Glc_3Man_9GlcNAc_2$ oligosaccharide precursor by the OST complex. After processing of the signal peptide, the protein is folded by the aid of chaperones. ER N-glycan processing results in $Man_8GlcNAc_2$ type glycan. O-glycosylation is also initiated in the ER by the protein-O-mannosyltransferases. After transport to the Golgi apparatus, the N-glycans are further processed to the yeast-typical hypermannosyl-type glycans. In GlycoSwitch-engineered strains, the hypermannosylation is abolished and the glycans are processed to Gal$_2$GlcNAc$_2$Man$_3$GlcNAc$_2$. After processing of the pro-domain, the protein is secreted in the growth medium, where it may be a substrate for yeast proteases.
Figure 3B:
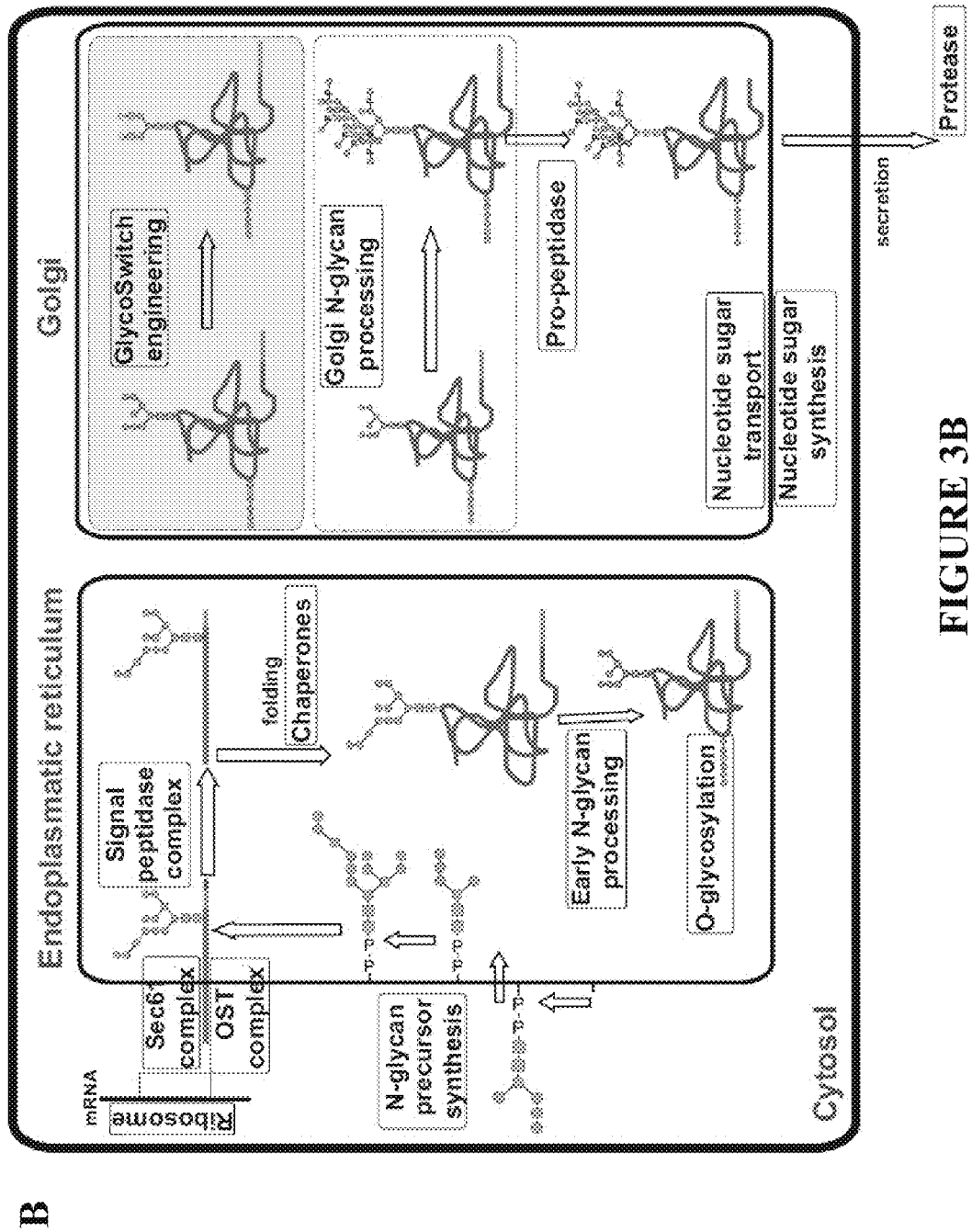

Efforts have been made to re-engineer the entire glycosylation pathway of *Pichia pastoris* in order to produce complex or hybrid type N-glycans (N-glycosylation humanization technology[1,2]; see also FIG. 3*b*). The heterologous glycosyltransferases needed for this engineered glycosylation processing utilize the sugar-nucleotides UDP-GlcNAc and UDP-Gal as monosaccharide donors. The identification of a UDP-GlcNAc transporter in the *Pichia* genome is consistent with the fact that UDP-GlcNAc is known to be synthesized in yeasts for the synthesis of cell wall chitin. However, no galactosylated glycoconjugates in *P. pastoris* have been previously described. It has been shown that the mere overexpression of a *Pichia* Golgi-targeted version of human beta-1,4-galactosyltransferase I is sufficient to achieve galactosylation of secreted glycoproteins[7]. While this finding may suggest that *Pichia* produces UDP-Gal and transports it into the Golgi apparatus, the present invention provides the molecular basis for the first time by identifying an endogenous cytoplasmic UDP-Glc-4-epimerase, and clear homologs of Golgi UDP-Galactose transporters. See also Table 5B. Researchers have previously overexpressed a heterologous UDP-Glc-4-epimerase in fusion to the galactosyltransferase to achieve higher levels of UDP-Gal in the yeast Golgi apparatus[2,8]. The identification of the *Pichia pastoris* proteins involved in nucleotide sugar synthesis and transport permits more effective glycan engineering in this and other methylotrophic yeasts.

In one embodiment, the present invention is directed to isolated nucleic acid molecules comprising a nucleotide sequence that encodes a protein (e.g., a full-length protein) as set forth in any of SEQ0129 to SEQ0132, or encodes a protein that is substantially homologous to a full-length protein as set forth in any of SEQ0129 to SEQ0132.

In a specific embodiment, the present invention is directed to isolated nucleic acid molecules comprising the coding sequence of an ORF as set forth in any of SEQ0129 to SEQ0132, or a nucleotide sequence that is substantially homologous thereto.

In another embodiment, the invention is drawn to an isolated protein comprising an amino acid sequence (e.g., a full-length protein sequence) as set forth in any of SEQ0129 to SEQ0132, or an amino acid sequence substantially homologous thereto.

In a further embodiment, the present invention is directed to expression vectors to achieve increased expression in *Pichia* of native glycosylation precursor synthesis enzymes or transporters, e.g. UDP-Gal or UDP-GlcNAc transporters and UDP-Glc-4-epimerase for ER or Golgi localization. It is believed that increased expression of these proteins can increase homogeneity of final hybrid or complex type glycoform on the heterologous protein designed to be expressed in the same strain. The expression vectors contain the coding sequence of one of the desirable glycosylation precursor synthesis enzymes or transporters, which is placed in operable linkage to a promoter functional in recipient host cells. The promoters that control the expression of the precursor synthesis enzymes or transporters can be selected to be induced by similar conditions to those directing the expression of the heterologous protein.

In another embodiment, the invention provides methylotrophic yeast strains especially *Pichia* strains which overexpress one or more native or *Pichia pastoris* glycosylation precursor synthesis enzymes or transporters, e.g. UDP-Gal or UDP-GlcNAc transporters and UDP-Glc-4-epimerase for ER or Golgi localization Genes Involved in O-Glycosylation In accordance with the present invention, 5 genes have been identified as encoding proteins involved in O-glycosylation. In the annotated Sequence file provided herein, the nucleotide sequences of the 5' upstream region (including promoter), the ORF and the 3' downstream region, as well as the amino acid sequence, of each of these 5 genes are set forth in SEQ0133 to SEQ0137.

In one embodiment, the present invention is directed to isolated nucleic acid molecules comprising a nucleotide sequence that encodes a protein (e.g., a full-length protein) as set forth in any of SEQ0133 to SEQ0137, or encodes a protein that is substantially homologous to a full-length protein as set forth in any of SEQ0133 to SEQ0137.

In a specific embodiment, the present invention is directed to isolated nucleic acid molecules comprising the coding sequence of an ORF as set forth in any of SEQ0133 to SEQ0137, or a nucleotide sequence that is substantially homologous thereto.

In another embodiment, the invention is drawn to an isolated protein comprising an amino acid sequence (e.g., a full-length protein sequence) as set forth in any of SEQ0133 to SEQ0137, or an amino acid sequence substantially homologous thereto.

In addition to N-glycosylation, yeasts also O-glycosylate secreted proteins with oligomannosyl-glycans that differ from the mucin-type O-glycosylation in humans[9]. No robust engineering approach has yet been developed to overcome this issue prior to this invention. The identification herein of the *Pichia* protein-O-mannosyltransferases that initiate this modification in the ER permits genetic modification of *Pichia* to reduce O-glycosylation.

Specifically, in a further embodiment, the present invention is directed to methylotrophic yeast strains, e.g., *Pichia* such as *P. pastoris* strains, in which one of more of the identified O-mannosyl transferase genes are inactivated to reduce or eliminate unwanted O-glycosylation of a heterologous protein.

Genes Encoding Mannosyltransferases

In accordance with the present invention, 18 genes have been identified as encoding mannosyltransferases, including 14 α-mannosyltransferases. In the annotated Sequence file provided herein, the nucleotide sequences of the 5' upstream region (including promoter), the ORF and the 3' downstream region, as well as the amino acid sequence, of each of these 18 genes are set forth in SEQ0138-0152 and 0210-0212.

In one embodiment, the present invention is directed to isolated nucleic acid molecules comprising a nucleotide sequence that encodes a protein (e.g., a full-length protein) as set forth in any of SEQ0138-0152 or 0210-0212, or encodes a protein that is substantially homologous to a full-length protein as set forth in any of SEQ0138-0152 or 0210-0212.

In a specific embodiment, the present invention is directed to isolated nucleic acid molecules comprising the coding sequence of an ORF as set forth in any of SEQ0138-0152 or 0210-0212, or a nucleotide sequence that is substantially homologous thereto.

In another embodiment, the invention is drawn to an isolated protein comprising an amino acid sequence (e.g., a full-length protein sequence) as set forth in any of SEQ0138 to SEQ0152, or an amino acid sequence substantially homologous thereto.

In terms of N-glycosylation, methylotrophic yeasts such as *P. pastoris* modify proteins with a range of heterogeneous high-mannose glycans, which introduce a large amount of heterogeneity in the protein (reducing downstream processing efficiency and complicating product characterization) and induce fast clearance from the bloodstream. The highly immunogenic terminal alpha-1,3-mannosyl glycotypes that are abundantly produced by *S. cerevisiae* are not detected on *Pichia*-produced glycoproteins. Consistently, no ortholog of the *S. cerevisiae* MNN1 gene (encoding the alpha-1,3-mannosyltransferase) has been found in the *Pichia* genome. However, *Pichia* glycoproteins can in some cases be modified with beta-1,2-mannose residues[10], reminiscent of antigenic epitopes on the *Candida albicans* cell wall[11]. *P. pastoris* AMR2 beta-mannosyltransferase, which has been documented in the art, has been identified in the genome. 3 homologs of AMR2 beta-mannosyltransferase have also been identified (SEQ0210-0212), thus providing the basis for reducing the levels of undesired beta-mannosylation.

Specifically, in a further embodiment, the present invention is directed to methylotrophic yeast strains, particularly *Pichia* strains, in which one of more of the identified *P. pastoris* mannosyltransferase genes are inactivated, for example, the homolog genes of AMR2 beta-mannosyltransferase as set forth in SEQ0210-0212, to reduce or eliminate unwanted beta-mannosylation of a heterologous protein.

Genes Encoding Proteins Involved in ER Glycosylation Pathway

In accordance with the present invention, 13 genes have been identified as encoding proteins involved in the ER glycosylation pathway. In the annotated Sequence file provided herein, the nucleotide sequences of the 5' upstream region (including promoter), the ORF and the 3' downstream region, as well as the amino acid sequence, of each of these 13 genes are set forth in SEQ0153 to SEQ0165.

In one embodiment, the present invention is directed to isolated nucleic acid molecules comprising a nucleotide sequence that encodes a protein (e.g., a full-length protein) as set forth in any of SEQ0153 to SEQ0165, or encodes a protein that is substantially homologous to a full-length protein as set forth in any of SEQ0153 to SEQ0165.

In a specific embodiment, the present invention is directed to isolated nucleic acid molecules comprising the coding sequence of an ORF as set forth in any of SEQ0153 to SEQ0165, or a nucleotide sequence that is substantially homologous thereto.

In another embodiment, the invention is drawn to an isolated protein comprising an amino acid sequence (e.g., a full-length protein sequence) as set forth in any of SEQ0153 to SEQ0165, or an amino acid sequence substantially homologous thereto.

In a further embodiment, the invention is directed to methylotrophic yeast strains, especially *Pichia* strains such as *P. pastoris*, in which one or more of the genes as set forth in SEQ0153-0165 have been inactivated. An alternative to modification of glycans after transfer to a protein is the modification of the glycan precursor before transfer to the protein. Inactivation of enzyme activities in the synthesis of the glycan precursor in the ER can result in glycolysation of proteins with modified glycan structures. In the event that inactivation of one of the genes as set forth in SEQ0153-0165 results in a lethal phenotype as the generated glycan-precursor is a non-optimal substrate for further processing steps, overexpression of a downstream enzyme, or expression of a modified or alternative downstream enzyme (e.g., LmSTT3 as further discussed below), may overcome this defect.

In still another embodiment, the invention is directed to the use of the *Pichia pastoris* STT3 gene sequence as set forth in SEQ0163 to disrupt the chromosomal STT3 gene, and optionally, to further insert a heterologous STT3 gene, such as the *Leishmania* STT3 gene into the *Pichia pastoris* STT3 locus.

In yeast, STT3 is a part of the oligosaccharyl-transferase (OT) complex which transfers the lipid linked oligosaccharide to the protein. *Leishmania major* has four STT3 paralogues, of which 3 could complement a yeast stt3 deletion. Furthermore, it has been reported that LmSTT3 does not work in the OT-complex but is active as a dimeric complex. It is suggested that the various LmSTT3 dimeric complexes display different protein substrate specificities at the level of individual glycosylation sequences. In addition, the LmSTT3D dimeric complex has a relaxed specificity with respect to the lipid linked oligosaccharide substrate. In contrast to the homogenous OT-complex, LmSTT3 OTase has no reduced transfer efficiency of glycans lacking α-1,2-linked mannoses on the B and C branch[12], Replacing the *Pichia pastoris* STT3 by LmSTT3D can provide glycosylation flexibility when the native OT-complex of *Pichia pastoris* is unable to transfer modified lipid-linked oligosaccharides to the protein.

"Knock-in" of LmSTT3—The coding sequence of the LmSTT3D gene is amplified by PCR using specific primers. The coding sequence is subsequently cloned into the expression plasmid using unique restriction sites which places the coding sequence under control of a promoter of the expression plasmid, these restriction sites are incorporated in the primers. The expression vector contains a sequence of the *Pichia pastoris* STT3 gene ("PpSTT3"). Prior to transformation in the *P. pastoris* strain, the plasmid containing the LmSTT3 expression cassette was digested with a unique site in the PpSTT3 sequence to facilitate integration. Transformants are selected for by using the selection marker present on the expression plasmid. To evaluate whether glycosylation is increased, N-glycans derived from secreted glycoproteins are analyzed by DSA-FACE capillary electrophoresis.

"Knock-out" of PpSTT3—The coding sequences of the LmSTT3D gene is amplified by PCR using specific primers. The coding sequence is subsequently cloned into the expression plasmid using unique restriction sites which place the coding sequence under control of a promoter of the expression plasmid, these restriction sites are incorporated in the primers. The expression vector contains two *Pichia pastoris* sequences flanking the LmSTT3 expression cassette, these sequences are upstream and downstream of the PpSTT3 gene. Prior to transformation into the *P. pastoris* strain, the plasmid containing the LmSTT3 expression cassette was digested with restriction endonuclease(s), excising the LmSTT3 cassette containing the PpSTT3 sequences. Transformants are selected by using the selection marker present in the expression cassette. To evaluate whether glycosylation is increased, N-glycans derived from secreted glycoproteins are analyzed by DSA-FACE capillary electrophoresis.

Other Genes Encoding Proteins Involved in the Glycosylation Pathway

In accordance with the present invention, 3 genes have been identified as encoding additional proteins involved in the glycosylation pathway (*S. cerevisiae* MNN4 homologs). In the annotated Sequence file provided herein, the nucleotide sequences of the 5' upstream region (including promoter), the ORF and the 3' downstream region, as well as the amino acid sequence, of each of these 3 genes are set forth in SEQ0166 to SEQ0168.

In one embodiment, the invention is directed to methylotrophic yeast strains which overexpress one or more of the MNN4 homologs to promote the core type phosphorylation of N-glycans. Increased phosphorylation of recombinant proteins can be useful in directing the protein for uptake throught the mannose-6-phosphate receptor[13]. Expression vectors for achieving such elevated expression are also part of the present invention. To evaluate whether manno-phosphorylation is increased from such modified strains, N-glycans derived from secreted glycoproteins after 48 hours culture in YPD medium are analyzed by DSA-FACE capillary electrophoresis. The amount of $Man_8GlcNAc_2$ will be drastically reduced in favor of two structures that migrate faster (compared to $Man_8GlcNAc_2$) and that are likely to contain one (P) and two (PP) phosphate residues, respectively. Assuming that both peaks derive from the $Man_8GlcNAc_2$ peak, the amount of $Man_8GlcNAc_2$ converted to phosphorylated glycans can be quantitated.

Genes Encoding Proteins Involved Methanol Metabolism

In accordance with the present invention, 10 genes have been identified as encoding proteins involved in methanol metabolism. In the annotated Sequence file provided herein, the nucleotide sequences of the 5' upstream region (including promoter), the ORF and the 3' downstream region, as well as the amino acid sequence, of each of these 10 genes are set forth in SEQ0169 to SEQ0178. While some of these genes have been documented in the art, the promoters have not been identified prior to the present application.

The commonly used methanol-inducible promoters in *P. pastoris*, the alcohol oxidase I (AOXI) promoter and the formaldehyde dehydrogenase (FLD) promoter, drive the production of enzymes needed for methanol assimilation and therefore produce extremely high levels of these transcripts upon switching the carbon source to methanol. The *P. pastoris* genome sequence has now allowed identification of all genes coding for enzymes involved in methanol assimilation (FIG. 3A and Table 5A) and their promoters, which are useful for driving transgene expression in *P. pastoris*.

In one embodiment, the present invention is directed to isolated nucleic acid molecules comprising a nucleotide sequence that encodes a protein (e.g., a full-length protein) as set forth in any of SEQ0172-SEQ 0174 or SEQ0176 to SEQ0178, or encodes a protein that is substantially homologous to a full-length protein as set forth in any of SEQ0172-SEQ 0174 or SEQ0176 to SEQ0178.

In a specific embodiment, the present invention is directed to isolated nucleic acid molecules comprising the coding sequence of an ORF as set forth in any of SEQ0172-SEQ 0174 or SEQ0176 to SEQ0178, or a nucleotide sequence that is substantially homologous thereto.

In another embodiment, the invention is drawn to an isolated protein comprising an amino acid sequence (e.g., a full-length protein sequence) as set forth in any of SEQ0172-SEQ 0174 or SEQ0176 to SEQ0178, or an amino acid sequence substantially homologous thereto.

In a further embodiment, the present invention is directed to the promoters of the genes disclosed in SEQ0169 to SEQ0178. These promoters can be placed in an operable linkage to a heterologous gene for methanol-inducible recombinant expression in *Pichia pastoris*. Therefore, expression vectors, host cells and methods of recombinant expression by utilizing any of the promoters disclosed in SEQ0169 to SEQ0178 are also embodiments of the present invention.

Genes Encoding Protein Homologs of *S. Cerevisiae* Proteases and Protease Inhibitor In accordance with the present invention, 8 genes have been identified as encoding protein homologs of *S. cerevisiae* proteases or protease inhibitors. In the annotated Sequence file provided herein, the nucleotide sequences of the 5' upstream region (including promoter), the ORF and the 3' downstream region, as well as the amino acid sequence, of each of these 8 genes are set forth in SEQ0179 to SEQ0186. SEQ0179 sets forth a *Pichia pastoris* gene encoding a serine-type peptidase. SEQ0180 sets forth a *Pichia pastoris* gene encoding a serine-type endopeptidase inhibitor. SEQ0181-0186 sets forth *Pichia pastoris* genes coding for aspartic-type endopeptidases.

In one embodiment, the present invention is directed to isolated nucleic acid molecules comprising a nucleotide sequence that encodes a protein (e.g., a full-length protein) as set forth in any of SEQ0179 to SEQ0186, or encodes a protein that is substantially homologous to a full-length protein as set forth in any of SEQ0179 to SEQ0186.

In a specific embodiment, the present invention is directed to isolated nucleic acid molecules comprising the coding sequence of an ORF as set forth in any of SEQ0179 to SEQ0186, or a nucleotide sequence that is substantially homologous thereto.

In another embodiment, the invention is drawn to an isolated protein comprising an amino acid sequence (e.g., a full-length protein sequence) as set forth in any of SEQ0179 to SEQ0186, or an amino acid sequence substantially homologous thereto.

In a further embodiment, the present invention is directed to vectors for inactivating one or more of the Pichia proteases, and to Pichia strains having one or more of the protease genes inactivated.

In another embodiment, the present invention is directed to expression vectors capable of expressing the serine-type endopeptidase inhibitor (SEQ0180) in a methylotrophic yeast strain such as P. pastoris, and methylotrophic yeast strains such as P. pastoris engineered transformed with such expression vector to produce the endopeptidase inhibitor at an elevated level.

The protease-deficient Pichia strains and strains that produce the endopeptidase inhibitor at an elevated level (i.e., overpression), are believed to allow more stable accumulation of a heterologous protein expressed in these strains. Such strains may be useful especially for producing recombinant immunoglobulins.

Genes Encoding Chaperones

In accordance with the present invention, 14 genes have been identified as encoding chaperones. In the annotated Sequence file provided herein, the nucleotide sequences of the 5' upstream region (including promoter), the ORF and the 3' downstream region, as well as the amino acid sequence, of each of these 14 genes are set forth in SEQ0187 to SEQ0200.

In one embodiment, the present invention is directed to isolated nucleic acid molecules comprising a nucleotide sequence that encodes a protein (e.g., a full-length protein) as set forth in any of SEQ0187 to SEQ0200, or encodes a protein that is substantially homologous to a full-length protein as set forth in any of SEQ0187 to SEQ0200.

In a specific embodiment, the present invention is directed to isolated nucleic acid molecules comprising the coding sequence of an ORF as set forth in any of SEQ0187 to SEQ0200, or a nucleotide sequence that is substantially homologous thereto.

In another embodiment, the invention is drawn to an isolated protein comprising an amino acid sequence (e.g., a full-length protein sequence) as set forth in any of SEQ0187 to SEQ0200, or an amino acid sequence substantially homologous thereto.

The present invention has now provided a complete catalog of orthologs of the S. cerevisiae ER folding machinery. This information is especially useful for design of an efficacious folding system. In one embodiment, the present invention is directed to expression vectors and engineered Pichia strains for increased expression of one or more native Pichia chaperones. The chaperone coding sequences can be placed under the control of a promoter selected to be induced by similar conditions to those for heterologous protein expression. Expression libraries of multiple chaperones can be screened to identify the most effective combination of chaperon expression for a particular heterologous protein. For example, a series of libraries of chaperones can be created, with each library having a different drug resistance marker incorporated for selection, such that either successive or combinatorial introduction of members of these libraries into a strain expressing a heterologous protein may be selected.

5S Ribosomal RNA Gene

In accordance with the present invention, the P. pastoris 5S ribosomal RNA gene has been identified and set forth in SEQ0201.

One strategy for optimizing protein expression levels in a recipient cell is to increase copy number of the expression cassette. This effort has been hampered by the absence of knowledge regarding sequences which occur multiple times in the Pichia genome and could be used for stable multi-copy strain generation through homologous recombination-mediated targeting of such multi-copy sequences. The 5S rRNA coding-sequence of Pichia pastoris provides the basis for multi-copy targeting. Contrary to the situation in S. cerevisiae, the 5S rRNA-coding sequence is not a part of the rDNA repeat locus in Pichia pastoris, and many copies of the 5S rRNA coding-sequence are spread over the 4 chromosomes of Pichia pastoris (FIG. 1B), thus providing an ideal targeting site for multi-copy integration.

To practice this aspect of the invention, the 5S rRNA coding sequence can be placed in a vector which also carries an expression cassette of interest and a selectable marker. The selectable marker can be a dominant selection marker that confers drug resistance, or a marker that confers phenotype selectable based on prototrophy. A unique restriction site is made or designed to be available within the 5S rRNA coding sequence. The vector is linearized by using the restriction enzyme that cleaves in the 5S rRNA coding sequence. The linearized vector is transformed into Pichia pastoris, and drug-resistant clones are isolated at increasing drug concentrations. Those clones that are resistant against the highest drug concentrations are expectedly those that have taken up the largest number of expression cassettes. Alternatively, when the selectable marker supplies an enzyme (e.g., HIS4), the clones that grow faster in the appropriate seletable media are identified as having multicopy integration. This procedure can be repeated until an optimal number of expression cassettes in the strain is obtained. Protein production in the selected strains is evaluated using methods known in the art.

Accordingly, the present invention also provides expression vectors capable of mediating multi-copy integration of an expression cassette onto the chromosomes of Pichia pastoris, as well as Pichia pastoris containing multiple copies of the expression cassette, stably integrated into the chromosomes. An expression cassette, as used in the present context, refers to a nucleic acid that includes, from 5' to 3', a promoter, the coding sequence of a heterologous protein of interest, and a 3' downstream sequence including a transcription termination sequence.

Genes Encoding Proteins Involved in Xylose, Arabinose and Threhalose Metabolism

In accordance with the present invention, 8 genes have been identified as encoding proteins involved in xylose, arabinose or threhalose metabolism. In the annotated Sequence file provided herein, the nucleotide sequences of the 5' upstream region (including promoter), the ORF and the 3' downstream region, as well as the amino acid sequence, of each of these 7 genes are set forth in SEQ0202 to SEQ0209.

In one embodiment, the present invention is directed to isolated nucleic acid molecules comprising a nucleotide sequence that encodes a protein (e.g., a full-length protein) as set forth in any of SEQ0202 to SEQ0209, or encodes a protein that is substantially homologous to a full-length protein as set forth in any of SEQ0202 to SEQ0209.

In a specific embodiment, the present invention is directed to isolated nucleic acid molecules comprising the coding sequence of an ORF as set forth in any of SEQ0202 to SEQ0209, or a nucleotide sequence that is substantially homologous thereto.

In another embodiment, the invention is drawn to an isolated protein comprising an amino acid sequence (e.g., a full-length protein sequence) as set forth in any of SEQ0202 to SEQ0209, or an amino acid sequence substantially homologous thereto.

In still another embodiment, the present invention is directed to the promoters of the genes disclosed in SEQ0202 to SEQ0209. These promoters are expected by the induced by specific sugars (xylose and arabinose metabolism pathway by C5 sugars, and threhalose pathway by α-1,1-disaccharides) can be placed in an operable linkage to a heterologous gene for inducible recombinant expression in Pichia pastoris. Therefore, expression vectors, host cells and methods of recombinant expression by utilizing any of the promoters disclosed in SEQ0202 to SEQ0209 are also embodiments of the present invention.

General Methodology

Gene Knockouts

To reduce the protease, protein-O-mannosyltransferase or beta-mannosyltransferase activity in Pichia pastoris, the genes encoding these enzymes are inactivated. This is achieved through standard yeast genetics techniques. Examples of such techniques include gene replacement through double homologous recombination, in which homologous regions flanking the gene to be inactivated are cloned in a vector flanking a selectable marker gene (such as an antibiotic resistance gene or a gene complementing an auxotrophy of the yeast strain). Alternatively, the homologous regions can be PCR-amplified and linked through overlapping PCR to the selectable marker gene. Subsequently, such DNA fragments are transformed into Pichia pastoris through methods known in the art, e.g., electroporation. Transformants that then grow under selective conditions are analyzed for the gene disruption event through standard techniques, e.g. PCR on genomic DNA or Southern blot. In an alternative experiment, gene inactivation can be achieved through single homologous recombination, in which case, e.g. the 5' end of the gene's ORF is cloned on a promoterless vector also containing a selectable marker gene. Upon linearization of such vector through digestion with a restriction enzyme only cutting the vector in the target-gene homologous fragment, such vector is transformed into Pichia pastoris. Integration at the target gene site is confirmed through PCR on genomic DNA or Southern blot. In this way, a duplication of the gene fragment cloned on the vector is achieved in the genome, resulting in two copies of the target gene locus: a first copy in which the ORF is incomplete, thus resulting in the expression (if at all) of a shortened, inactive protein, and a second copy which has no promoter to drive transcription.

Alternatively, transposon mutagenesis is used to inactivate the target gene. A library of such mutants can be screened through PCR for insertion events in the target gene.

The functional phenotype (i.e., deficiencies) of an engineered/knockout strain can be assessed using techniques known in the art. For example, a deficiency of an engineered strain in protease activity can be ascertained using any of a variety of methods known in the art, such as an assay of hydrolytic activity of chromogenic protease substrates, band shifts of substrate proteins for the select protease, among others. A deficiency in protein O-mannosylation can be detected by mass changes of expressed O-glycosylated proteins and through mass spectrometrical techniques designed to detect the sites of O-glycosylation (such as beta-elimination in 18O—H2O), used in a comparative experiment with the same protein expressed in a non-engineered strain. Beta-mannosyltransferase deficiency can be detected through glycan analysis of expressed proteins that are beta-mannosylated in non-engineered strains or through loss of signal with beta-mannosyl specific antibodies.

Gene Over-Expression

To increase the expression level in Pichia pastoris of desirable genes such as polypeptide-folding-promoting proteins, UDP-Gal or UDP-GlcNAc transporters and UDP-Glc-4-epimerase, the ORFs or coding sequences of such genes are cloned under the control of a promoter of desired strength and regulation (such as the methanol-inducible AOXI, AOXII or FLD promoters, or the constitutively expressed GAP or TEF1alpha promoter), in a vector also containing a selectable marker gene functional in Pichia pastoris. To increase transformation efficiency and/or target the vector to a selected genomic locus, the vector may be linearized in a genome-homologous sequence, although this is not essential. Subsequently, such vector is transformed into Pichia pastoris using techniques known in the art.

Promoter Analysis and Usage

Cloning of the promoters and generating engineered yeast strains—The promoter sequence is amplified from Pichia pastoris genomic DNA with primers designed to the 5' and 3' regions of the sequences provided herein. The corresponding PCR fragment is cloned in an appropriate vector by blunt or TA ligation or by restriction-ligation cloning using restriction sites, not present in the promoter, adapted to the primer. The promoter is subsequently cloned upstream of a gene of interest in a yeast expression vector. The expression vector is transferred into the Pichia pastoris strain according to protocols described by Cregg and Russel[14]. To generate stable transformants via homologous recombination, the vector is cleaved in a P. pastoris DNA segment (e.g., the P. pastoris promoter) with unique restriction sites. This allows integration into the genome by single crossover type insertion[15]. Transgenic yeast can be obtained on medium containing the selection marker or on medium lacking the complemented amino acid.

Analyzing promoter activity—To analyze the promoter activity, stable strains are generated as an example: a strain containing a marker gene under control of the promoter of interest and a reference strain with the marker gene controlled by a reference promoter. Quantitative analysis of expression levels of this marker can determine the relative activity of the promoter.

Identifying promoter sequence and cis-acting elements—For the identification of the promoter sequence, a 5'-deletion series is generated by PCR on P. pastoris genomic DNA as template. For this deletion series, a set of forward primers is designed which hybridize at different distance from the start. As reverse primer, a primer is used that hybridizes to the 3' end of the suggested promoter sequence. In a first screen, the promoter deletions can be done in steps of 100 bp. By this a rough estimation of the promoter size can be made. Later a second screen in this region can be performed with smaller deletion steps. The promoter deletions are cloned in an expression vector, in front of a marker gene which allows to quantify the expression. Analysis of expression levels compared to the whole sequence will allow identification of the promoter.

To identify cis-acting elements, a series of 3'-deletion fragments of the promoter are obtained next to the 5'-deletions in a similar fashion. In addition, a minimal promoter is fused to the 3'-deletion fragments to compensate for the loss of the TATA-box. Further, combinations of the 3' deletions (without minimal promoter) and 5' deletions are made by overlapping PCR. Expression vectors are generated containing the promoter fragments controlling the expression of a marker gene. Analysis of the activity of these promoter fragments can identify regulatory elements in the promoter.

In addition to the methanol-inducible promoters of the Alcohol Oxidase I gene and the formaldehyde dehydrogenase I gene, and the constitutively active promoter of the glyceraldehyde-3-phosphate dehydrogenase gene, the present invention provides additional *Pichia pastoris* genes involved in the glycolysis pathway, methanol assimilation, xylose, arabinose and threhalose metabolisms. The promoters of these genes can be used for driving overexpression of heterologous genes.

For those promoters of the genes in the methanol utilization pathway, the xylose metabolism, the arabinose metabolism and the threhalose metabolism, these promoters can be used for inducible expression of a heterologous gene. To assess the inducibility of these promoters by methanol, xylose, arabinose or threhalose, the expression of their endogenous gene can be compared by qPCR of cells grown in medium with or without addition of the rsepective carbon sources. For example, *P. pastoris* wild type cells are grown in BMGY (uninduced condition), centrifuged and induced in BMMY (for methanol induction), in media containing xylose, in media containing arabinose or in media containing threhalose, respectively. At different time points, samples will be taken. At every time point, RNA is isolated from the yeast cells, treated with DNAse to remove all genomic DNA and then the mRNA converted into cDNA. On all genes to be tested, primers are designed (by Primer3Plus Software) and tested for amplification of the gene. To be able to compare the expression of the different genes, a good reference gene (e.g., actin; GAPDH or PDA1) is included. All reference genes are tested in uninduced and induced conditions by qPCR and the best reference gene is chosen by the geNorm software. After selecting the best reference gene, qPCR with primers on the reference gene and primers on the gene of interest can be performed on every sample. Thereafter, the relative quantity ($RQ=2^{\Delta Cq}$, with $\Delta Cq$ the difference in PCR cycles between induced and non-induced condition) of every gene can be calculated (qBASEPlus software). From these RQs, the ratio of the gene of interest (GOI) relative to to the reference gene ($NRQ=RQ_{GOI}/RQ_{REF}$) is determined. When different genes are investigated, the gene that is most upregulated in the induced condition can be identified. The promoter driving this gene can then be used to drive expression of a heterologous test gene.

Counterpart Genes from Other Methylotrophic Yeast Species

Given the availability of the *Pichia pastoris* genome and annotation, counterpart genes from other methylotrophic yeast species, e.g., other *Pichia* species, can be isolated. Isolation of such counterpart genes can be useful in generating engineered methylotrophic yeast strains other than *Pichia pastoris* for recombinant production of heterologous glycoproteins.

Other Methylotrophic Yeast Species as Genetic Engineering Host

The present invention contemplates the use of a methylotrophic yeast strain, including but not limited to *Pichia* strains such as *Pichia pastoris*, as the host for genetic engineering and recombinant production of proteins including glycoproteins. While the identification of native *Pichia pastoris* genes and their constituents (such as promoters, signal peptides, proteins including enzymes and chaperons) are preferred choices for engineering a *Pichia pastoris* strain, these choices are believed to also work for other methylotrophic yeast strains, especially other *Pichia* strains closely related to *Pichia pastoris*.

Combination of Genetic Modifications

Embodiments described herein can be combined as appropriate. For example, genetic modifications of a strain, such as usage of inducible promoters, usage of signal peptides, inactivation of one or more protease genes, overexpression of nucleotide sugar synthesis and transport, inactivation of O- or beta-mannosylation, expression of chaperones, and multi-copy integration, for example, can be combined in any manner desirable.

The present invention is further supported and illustrated by the following examples.

EXAMPLE-1

This Example describes the methods employed to identify, assemble and annotate the full genomic sequence of *P. pastoris* GS115 strain.

DNA Preparation

*P. pastoris* GS115 (Invitrogen, Carlsbad, Calif.) is a strain derived from the wild type strain NRRL-Y 11430 (Northern Regional Research Laboratories, Peoria, Ill.). It has a mutation in the histinol dehydrogenase gene (HIS4) and was generated by nitrosoguanidine mutagenesis at Phillips Petroleum Co. It is the most frequently used *Pichia* strain for heterologous protein production.

*P. pastoris* genomic DNA was prepared according to a published protocol with minor modifications. Instead of vortexing, the samples were shaked in a Mixer Mill (Retsch) for 2 minutes.

Sample Preparation and Sequencing with Roche/454 Genome Sequencer FLX

The shotgun library of *P. pastoris* for sequencing on the Genome Sequencer FLX (GS FLX) was prepared from five micrograms of intact genomic DNA. Based on random cleavage of the genomic DNA[16] with subsequent removal of small fragments with AMPure™ SPRI beads (Agencourt, Beverly, Mass.), the resulting single-stranded (sst) DNA library showed a fragment distribution between 300 and 900 bp with a maximum of 574 bp. The optimal amount of sstDNA library input for the emulsion PCR[16] (emPCR) was determined empirically through two small-scale titrations leading to 1.5 molecules per bead used for the large-scale approach. A total of 64 individual emPCRs were performed to generate 3,974,400 DNA carrying beads for two two-region-sized 70×75 PicoTiterPlates (PTP) and each region was loaded with 850.000 DNA carrying beads. Each of the two sequencing runs was performed for a total of 100 cycles of nucleotide flows[16] (flow order TACG) and the 454 Life Sciences/Roche Diagnostics software Version 1.1.03 was used to perform the image and signal processing. The information about read flowgram (trace) data, basecalls and quality scores of all high quality shotgun library reads was stored in a Standard Flowgram Format (SFF) file which was used by the subsequent computational analysis (see below).

Within this sequencing project, a paired end library of *P. pastoris* (strain GS115) was prepared for subsequent ordering and orienting of contigs (see computational analysis below). Six micrograms of intact genomic DNA was sheared hydrodynamically (Hydroshear-Genomic Solutions, Ann Arbor, Mich.) and purified with AMPure™ SPRI beads (Agencourt, Beverly, Mass.) into DNA fragments of about 3 kbp in length. After methylation of Eco RI restriction sites, a biotinylated hairpin adaptor was ligated to the ends of the *P. pastoris* DNA fragments, followed by Eco RI digestion with a subsequent circularization. The restriction of the circularized DNA fragments with Mme I, the subsequent ligation of paired end adaptors and the amplification of the remaining DNA fragments resulted in a double-stranded paired end library with 130 bp in length. For the following eight individual emPCRs of the paired end library, 1.5 molecules per bead were used to generate 339,480 DNA-carrying beads of which 280,000 were loaded onto a region of a four-region sized 70×75 PTP. The subsequent sequencing run with the GS FLX was performed for a total of 42 cycles of nucleotide flow (see above) and the 454 Life Sciences/Roche Diagnostics software Version 1.1.03 was used to perform the image and signal processing. The information about read flowgram (trace) data, basecalls and quality scores of all high quality shotgun library reads was also stored in a SFF file which was used by the subsequent computational analysis.

Computational Analysis of GS FLX Shotgun and Paired End Reads

An automatic assembly pipeline (in-house software, Eurofins MWG Operon) was used to de novo assemble the generated shotgun and paired end reads.

For de novo assembly of the *P. pastoris* genome sequence, a total of 897,197 good quality base called, clipped shotgun reads with an average read length of 243 bp and a total of 70,500 good quality base called, clipped 20 bp-Paired End tag reads were used.

Within this pipeline, the information about all sequences and their quality was extracted from the SFF- into a FASTA-file and subsequently converted into CAF format, the input format of choice of the used assembler mira (version 2.9 26×3) for contig creation. The provided mate and size information (i.e., forward and reverse read and the 3 kbp of length) of the paired end reads was used to scaffold the resulting contigs from the de novo assembly[17].

Figure 4:
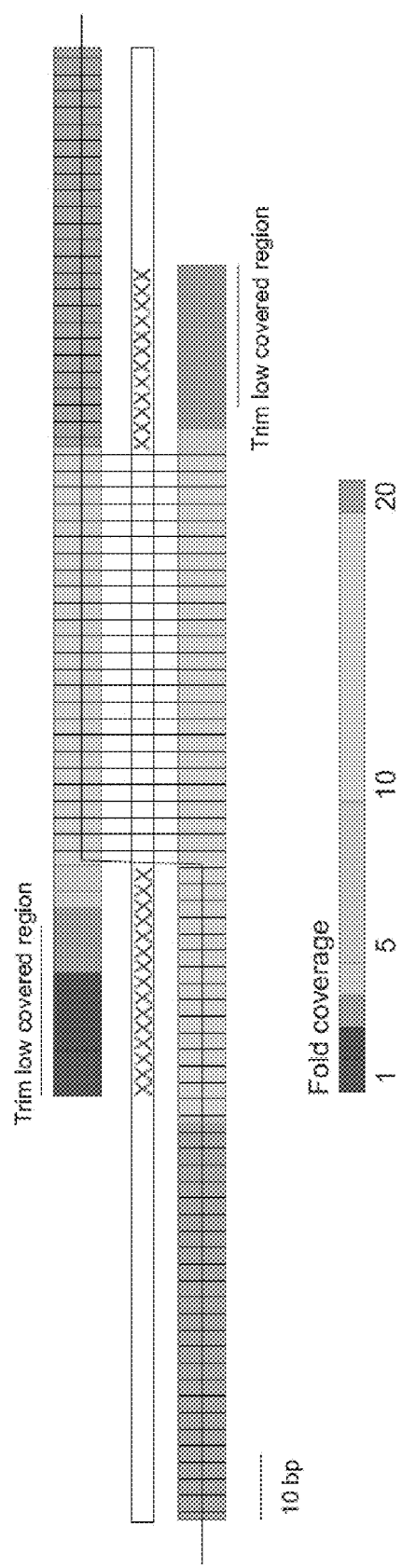
FIG. 4. Contig overlap processing. Conflicts at contig overlaps, due to low coverage of the sequence represented by "XXX", are resolved by trimming the extreme ends of the contig. Contig coverage is represented by heatmap. Low fidelity overlap regions (P-value>$e^{-50}$) were PCR amplified and Sanger sequenced.

Assembly (FIG. 1A and FIG. 4)

The initial assembly contained 1,154 contigs with 9.6 Mbp sequence and 20× sequencing depth. The contig N/L50 was 40/77 kbp. Assembly of the contigs was performed manually, based on homology between the contig ends. 13 contigs were assigned to chromosomes by identification of the chromosomal markers previously described[10] (Chromosome 1: HIS4, ARG4, OCH1, PASS, PRB1, PRC1; Chromosome 2: PAS8, GAP; Chromosome 3: DAS1, URA3, PEP4; Chromosome 4: AOX1, AOX2). Starting from these contigs, contigs with homologous contig ends were identified by BLASTN search with 500-1000 bp of the contig ends to a database with the contig sequences. Contigs sharing homology with a P-value<e-20 were assumed to be linked. Pools of potentially linked contigs were assembled to supercontigs by the SeqMan assembly software (DNASTAR inc, Madison, Wis., USA). The resulting contig junctions were curated by removing the low-coverage ends of either joined contig. In the cases where the BLASTN P-value was >e-50, the junction was PCR-amplified and Sanger-sequenced (primer sequences: Table 1). This resulted in 10 supercontigs, with 9.1 Mbp of sequence, and a remaining 7 unassembled contigs. The supercontig N/L 50 was 3/1.544 Mbp.

The mitochondrial genome was also assembled and had extremely high coverage (859.9 fold), indicating the presence of approx. 43 mitochondrial genomes per cell in *P. pastoris* when grown on glucose as carbon source.

Gap Joining and Finishing

Supercontigs were linked by mapping contigs to paired-end scaffolds (n=1) and automated prediction of protein-coding sequences revealed a partial ORF at the end of a supercontig, homologous to a WD40 domain protein in other yeasts (including *Pichia guillermondii* homolog PGUG 04385). Finding the other part of this ORF on one of the unassembled contigs allowed joining of this supercontig to one of the as yet unassembled contigs. This was confirmed by PCR and Sanger sequencing.

Figures 1B, 1C:
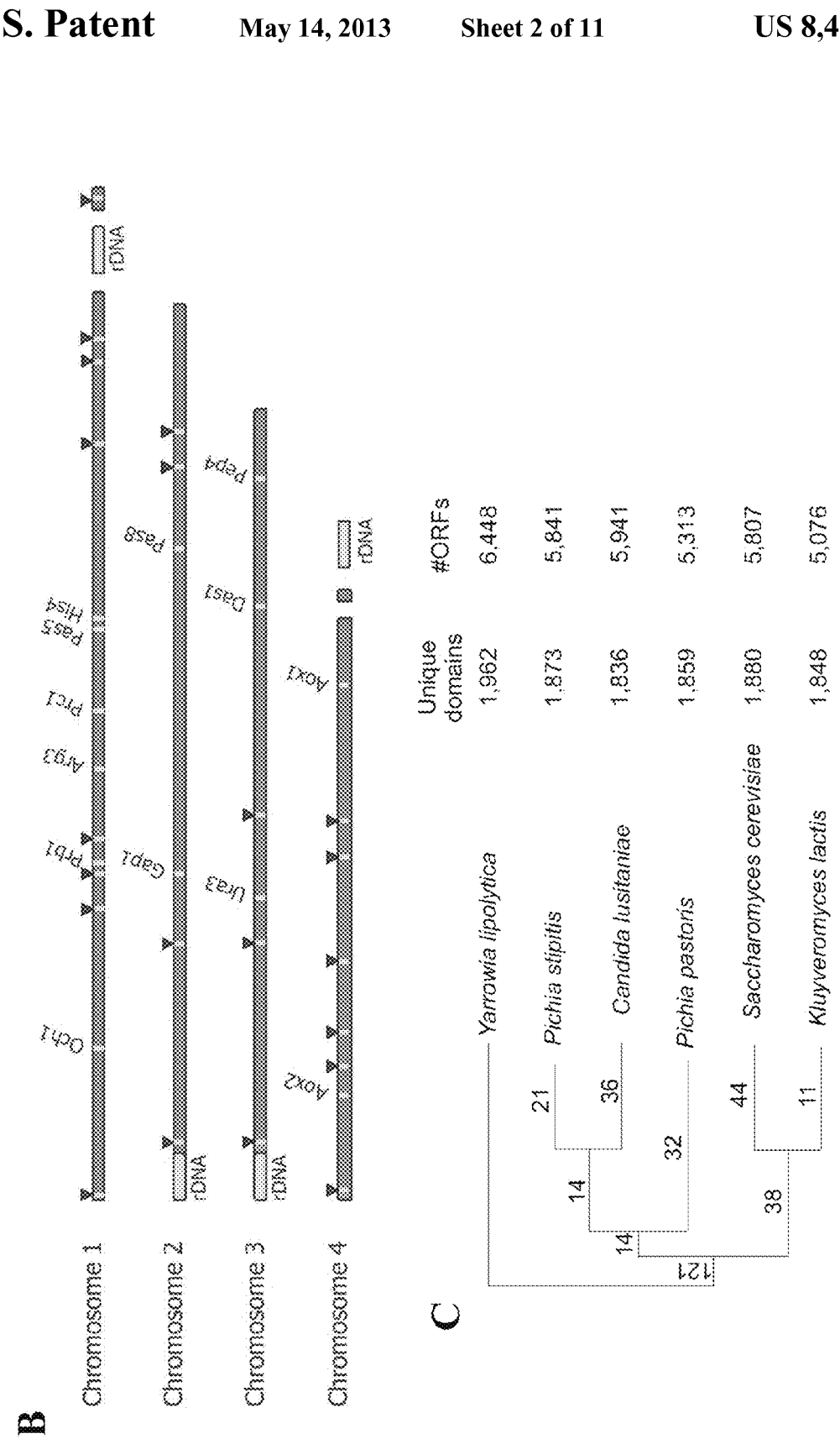
Figures 2A, 2B:
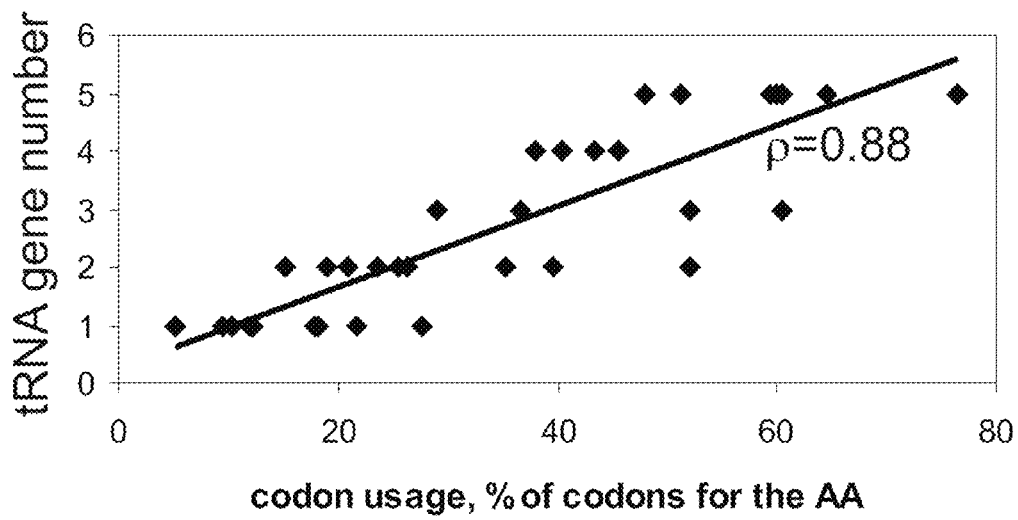
FIGS. 2A-2B. *Pichia pastoris* codon usage. 2A. Codon usage in the *P. pastoris* ORFeome. The relative abundance of a codon is represented as a percentage of the total codon usage for the amino acid. 2B. Correlation of tRNA genes and codon usage. Graph shows correlation between the codon usage in relation to the number of genes coding for tRNAs recognising this codon (Spearman rho=0.88, P<0.0001).
Figures 5A, 5B:
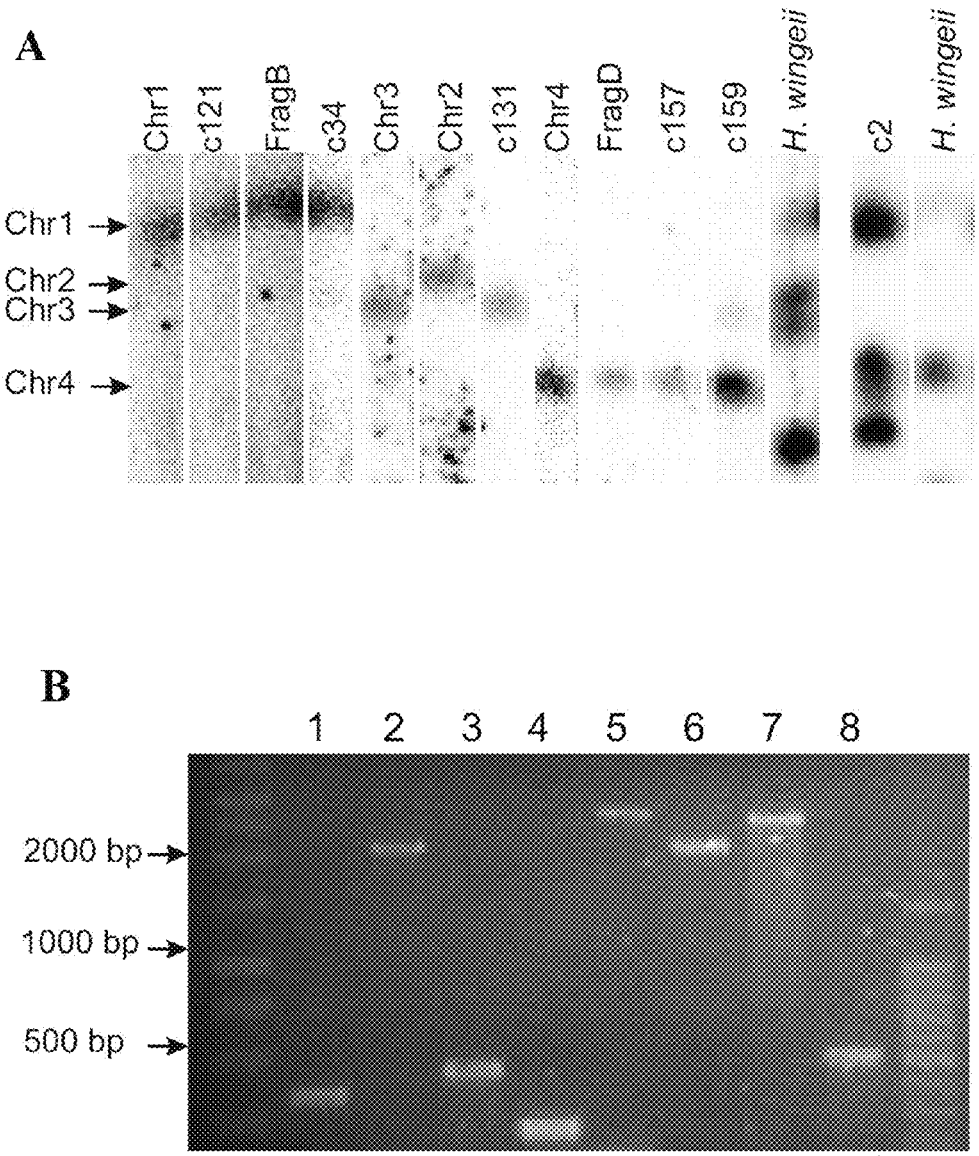
FIGS. 5A-5C. Chromosome assembly. 5A. By PFGE and Southern blot detection, 2 supercontigs (FragB and FragD), 4 contigs (c121, c34, c131, c157, c159) and the contig containing the rDNA repeats (c2) were located on the different chromosomes. Every lane of the blot was incubated with a probe on an open reading frame of the indicated genome fragment. A probe on HIS4, GAP, URA3 and AOX1 was chosen to detect chromosome 1, 2, 3 and 4, respectively. The *H. wingeii* chromosomes were used as marker for the PFGE, but they also gave a signal on the blot with the conserved c2 probe. The rightmost 2 lanes derived from a different gel than the rest of the figure, and chromosomes 2 and 3 were not well resolved on this gel. Presence of an rDNA locus (corresponding to contig c2) on both of these chromosomes was ascertained through PCR. 5B. Result of the PCRs performed to join the supercontigs and contigs. Lanes 1-8 are PCR with primers 1&4, 2&5, 6&25, 12&26, 8&9, 23&62, 15&60 and 17&21, respectively. 5C. Representation of the chromosomes assembled by the supercontigs and contigs. The numbers in blue represent PCR primers that were chosen on each end of the supercontigs and contigs (~200 bp from the end). The size of the gap is depicted between each supercontig and contig.
Figure 5C:
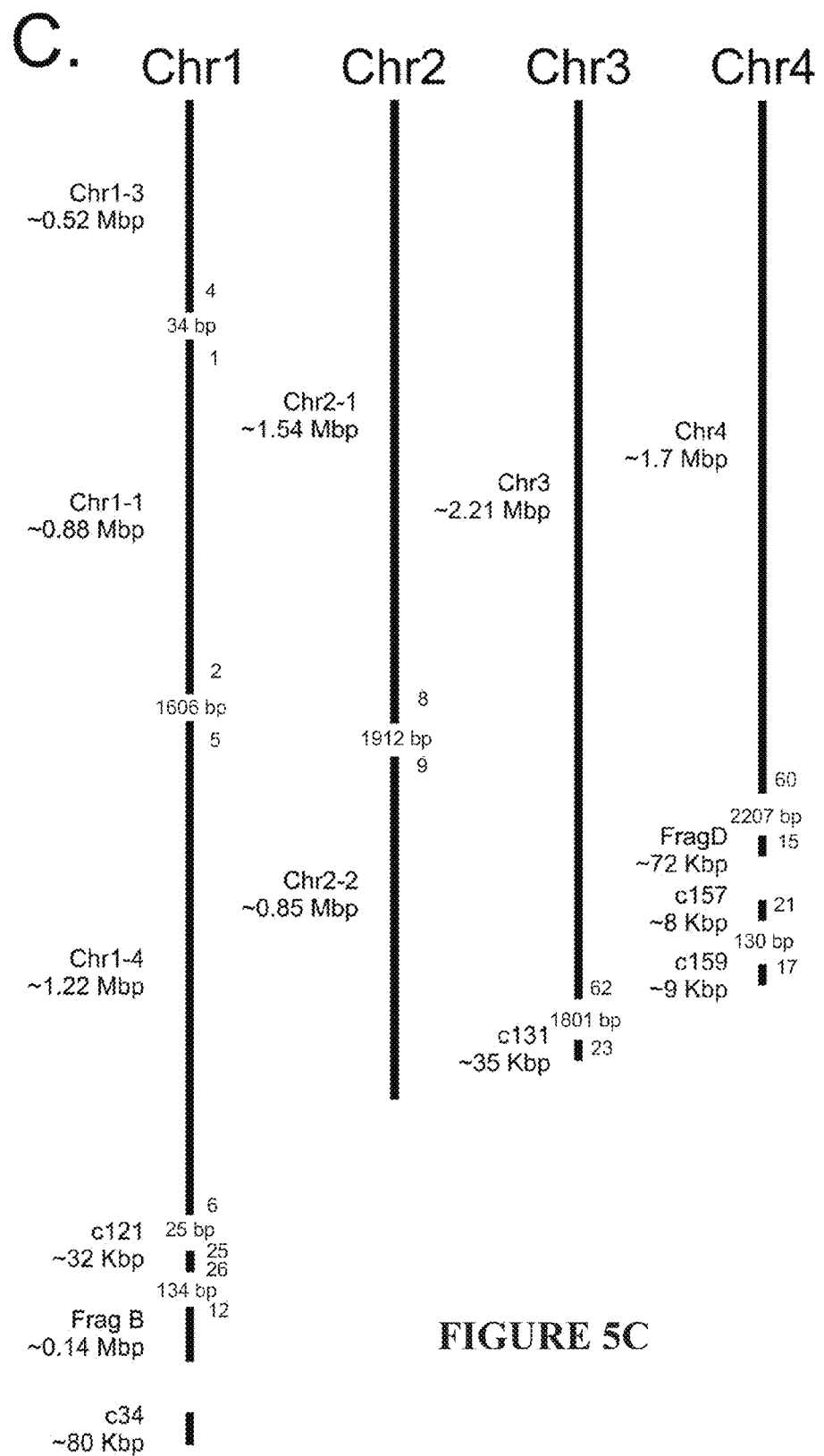

Seven of the 9 thus generated supercontigs could be assigned to a specific chromosome when they contained one or more of the 13 genes for which chromosomal location had been previously established[10] (FIG. 1B and FIG. 5C). For those two supercontigs and the 6 unassembled contigs where this was not the case, Southern blot analysis of pulsed-field gel electrophoresis-separated *Pichia pastoris* chromosomes (see below) was used for the assignment (FIG. 5A). After assignment to the chromosomes, orientation of the supercontigs and contigs on the chromosomes was determined by PCR analysis with primers on the contig ends (Table 1). Gaps were PCR-amplified using primers flanking these regions (Table 1) and sequenced by Sanger sequencing for finishing.

rDNA repeat regions were detected by Southern blot on all four PFGE-separated chromosomes (FIG. 5A). The Southern signal on chromosomes 1 and 4 was as strong as that on chromosomes 2 and 3 combined. Through PCR, the location and orientation of the rDNA locus was determined to be at one end of Chromosomes 2 and 3 (FIG. 1B). The attempts at verification of the rDNA locus position on chromosomes 1 and 4 (still containing 1 gap) were inconclusive.

Pulsed-Field Gel Electrophoresis (PFGE)

A BioRad contour-clamped homogeneous electric field CHEF DRIII system was used for PFGE. Chromosomal DNA was prepared in agarose plugs with the CHEF Genomic DNA Plug kit (BioRad) following the instructions of the manufacturer. A 0.8% agarose gel in 1× modified TBE (0.1 M Tris, 0.1 M Boric Acid, 0.2 mM EDTA) was used to separate the chromosomes. The gel was electrophoresed with a 106° angle at 14° C. at 3 V/cm for 32 h, with a switch interval of 300 s, followed by 32 h with a switch interval of 600 s and 24 h with a switch interval of 900 s. After separation, the chromosomes were visualized with ethidium bromide and the different contigs were mapped onto the chromosomes by Southern blot. Therefore, the gel was incubated in 0.25 M HCl for 30 minutes, followed by capillary alkali transfer of the DNA onto a Hybond N+ membrane (Amersham). The probes were prepared by PCR on an open reading frame. For chromosome specific probes, a part of the coding sequence of HIS4 (chromosome 1), GAP (Chromosome 2), URA3 (chromosome 3) and AOX1 (chromosome 4) was used. The probes were random labelled with α $^{32}$P dCTP, using the High Prime kit (Roche).

Automatic Gene Structure Prediction & Functional Annotation

Figure 6:
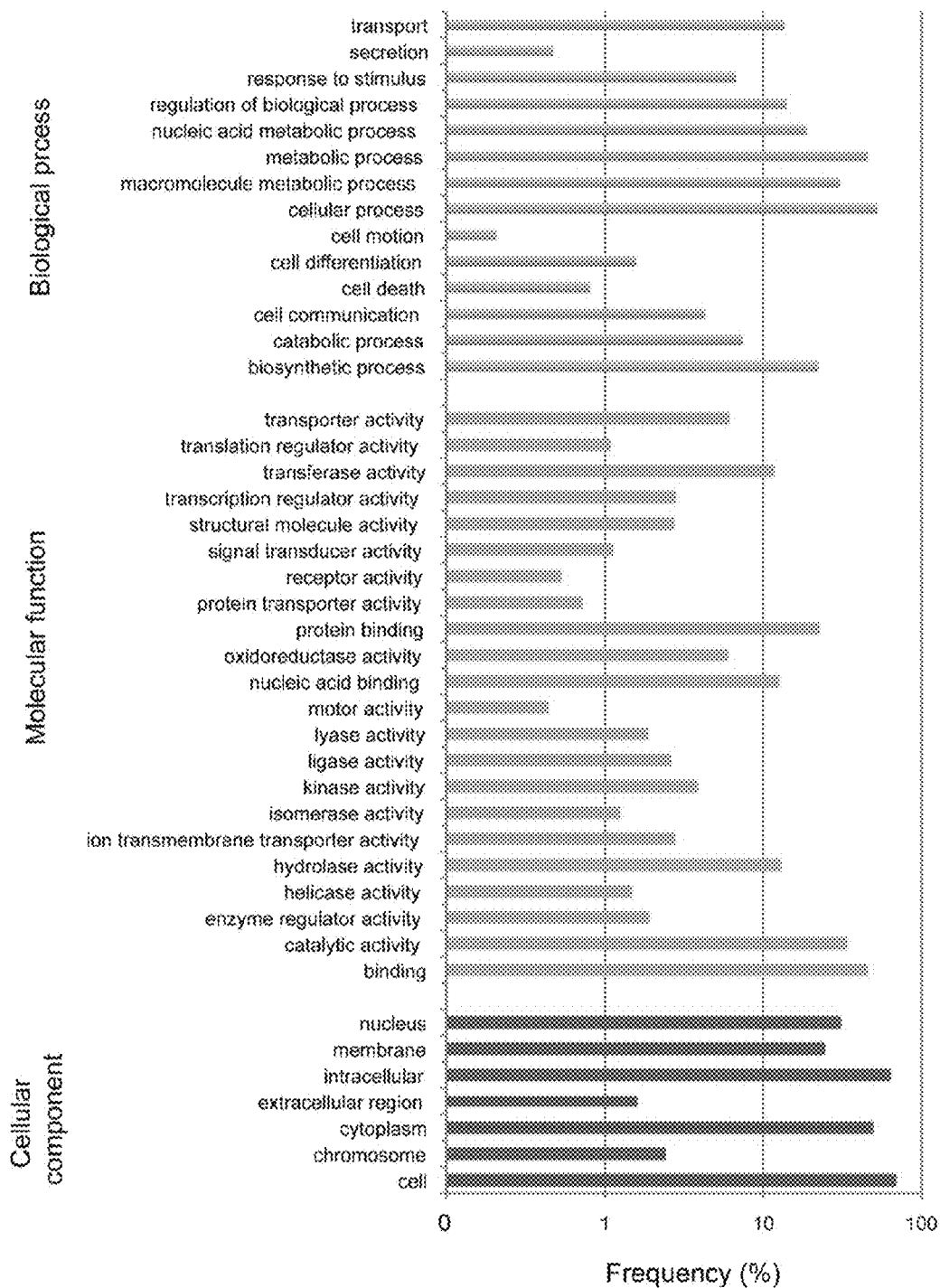
FIG. 6. Distribution of gene ontology terms assigned to *P. pastoris*. A total of 4,262 *P. pastoris* genes were assigned with gene ontology (GO) terms: 3,142 genes with molecular function assignment, 3,647 genes with cellular component assignment and 3,182 genes with biological process assignment.

Protein-coding genes were predicted by the integrative gene prediction platform EuGene[18] (FIG. 6). A specific EuGene version was trained based on 108 manually checked *P. pastoris* genes. Documented genes from *P. stipitis* and *S. cerevisiae* were used to build *P. pastoris* orthologous gene models allowing the training of *P. pastoris*-specific Interpolated Markov Models for coding sequences and introns. Splice sites were predicted by NetAspGene[19] and gene prediction from GeneMarkHMM-ES[20] trained for *P. pastoris* and AUGUSTUS[21] (*Pichia stipitis* model) were used to provide alternative gene models for EuGene prediction. The UniProt and the fungi RefSeq protein database were searched against the supercontig sequence by BLASTX to identify the coding area. The DeCypher-TBLASTX program was used to search the conserved sequence area between the *P. pastoris*, *P. stipitis* and *Candida guilliermondii* genomes.

All predicted protein-coding genes were searched against the yeast protein database, UniProt[22] and RetSeq[23] fungi protein database by BLASTP. Protein domains were detected by InterProScan[24] with various databases (BlastProDom, FPrintScan, PIR, Pfam, Smart, HMMTigr, SuperFamily, Panther and Gene3D) through the European Bioinformatics Institute Web Services SOAP-based web tools. Signal peptide and transmembrane helices were predicted by SignalP and TMHMM respectively. GO (Gene Ontology) terms[25] were derived from the InterProScan result and the KEGG (Kyoto Encyclopedia for Genes and Genomes) pathway and EC (Enzyme Commission) numbers were annotated by the annot8r pipeline.

Expert Gene Structure/Functional Annotation

The gene structure prediction and the database search results from various databases were formatted and stored in a MySQL relational database. A multiple alignment of each protein-coding gene with the top 10 best hits against the UniProt, RefSeq fungi and yeast protein database was built by MUSCLE[26]. A BOGAS (Bioinformatics Online Genome Annotation System) *P. pastoris* annotation website was setup as the workspace for expert annotators. The initial aim of BOGAS is to provide a workspace for gene structure and functional annotation. The editing of gene structure or gene function assignment is directly updated to the MySQL relational database through the web interface. All of the modification from expert annotators is traceable and reversible by the database system. Once the expert annotator modified the gene structure and change the translated protein product, the system will automatically trigger the update function to check the protein domain and protein database. BOGAS also provides a search function where users can search for genes by sequence similarity (BLAST), gene id, gene name or InterPro domain. Each predicted *Pichia* gene's structure and the similarity search result were visually inspected through an embedded strip-down version of ARTEMIS. The splice sites of each gene were carefully checked and compared with *S. cerevisiae* and *P. stipitis* loci. A functional description of each gene was added to the gene annotation when a closely related homologous gene was available.

Estimate of the Gene Space Completeness

Parra et al.[27] proposed a set of core eukaryotic genes (CEGs) to estimate the completeness of genome sequencing and assembly programmes. The CEGs contains 248 genes across six model organisms (*H. sapiens, D. melanogaster, C. elegans, A. thaliana, S. cerevisiae* and *S. pombe*) of which ~90% are single copy in *D. melanogaster, C. elegans, S. cerevisiae* and *S. pombe*. The protein-coding genes identified in this invention were checked with the HMM profile from the CEGs dataset by the HMMER package. All of the 248 CEGs were present in our curated gene set with full HMM domain coverage. Further, FUNYBASE (FUNgal phYlogenomic dataBASE)[28] provides 246 single-copy ortholog clusters in 21 sequenced fungal genomes. These single-copy protein sequences were extracted from the FUNYBASE website and built the HMM model for each cluster. The corrected *P. pastoris* protein sequences were searched with the FUNYBASE HMM database. All of the FUNYBASE models were presented in our gene catalog with complete domain coverage.

Detection of rRNA and tRNA Loci

Ribosomal RNAs were detected automatically by INFERNAL 1.0 (INFERence of RNA ALignment) against the Rfam[29] database and manually confirmed by BLASTN search with *S. cerevisiae* homologs to the *P. pastoris* genome sequence. Localization of the ribosomal DNA locus was assayed by PFGE and PCR.

Transfer RNAs were automatically predicted by tRNA Scan-SE 1.21[30] and manually confirmed by BLASTN search with the *S. cerevisiae* homologs to the *P. pastoris* genome sequence.

Codon Usage

Nucleotide sequences of the predicted *P. pastoris* ORFeome were analyzed with ANACONDA 1.5[31]. In addition to calculation of the codon use, the analysis by ANACONDA generates a codon-pair context map for the ORFeome. This map shows one colored square for each codon-pair, the first codon corresponds to rows and the second corresponds to columns in the map. Favored codon pairs are shown in green, underrepresented ones are shown in red.

Phylogenetic Tree Reconstruction of Fungal Genomes

The phylogenetic tree was based on 200 single-copy genes which were present in 12 sequenced fungal genomes. A multiple sequence alignment was constructed using the MUSCLE program and gap removal by in-house script based on the BLOSUM62 scoring matrix. The maximum likelihood tree reconstruction program TREE-PUZZLE[32] (quartet puzzling, WAG model, estimated gama distribution rate with 1000 puzzling step) was used for phylogenetic tree reconstruction. The tree was well supported by 1000 bootstraps in each node.

Comparative Analysis of Gene Family and Protein Domain

The predicted proteomes used in this study were those of six hemiascomycetes (*P. pastoris, S. cerevisiae, K. lactis, P. stipitis, C. lustianiae* and *Y. lipolytica*)[33,34]. In order to obtain the gene families, a similarity search of all protein sequences from the 6 fungi (all-against-all BLASTP, e-value 1e-10) was performed. Gene families were constructed by Markov clustering[35] based on the BLASTP result. All predicted protein sequences from the six genomes were searched against the Pfam[36] database to obtain the protein domain occurrence in each species. The protein domain loss and acquisition was counted based on the Dollo parsimony principle by the DOLLOP program from the PHYLIP package[37].

EXAMPLE-2

This Example describes the results of assembly and annotation of the full genomic sequence of *P. pastoris* GS115 strain.

Genome Sequencing and Assembly

Prior to this invention, very little was known about the genome features of *P. pastoris*. Ohi et al.[38] reported that the *P. pastoris* genome was organized in 4 chromosomes with a total estimated size of 9.7 Mbp (+/- a few hundred kbp, as the pulsed field gel electrophoresis technique has a relatively poor accuracy). In addition, Ohi et al. assigned 13 *P. pastoris* genes to the different chromosomes.

During the course of this invention, chromosome assembly was completed according to the strategy shown in FIG. 1A. 454/Roche sequencing[16] (GS-FLX version) was utilized to highly oversample the genome (20x coverage) and generated 70,500 paired-end sequence tags, to enable the assembly of all but 7 contigs into only 9 "supercontigs" (plus the mitochondrial genome) using automated shotgun assembly and BLASTN-based contig end joining (see Example 1 and FIG. 4). Upon assigning these supercontigs to the 4 chromosomes (see Example 1 and FIGS. 5A-5C), the order of the supercontigs was determined through PCR and Sanger sequencing of the amplificates. Through these finishing experiments, the 4 chromosomal sequences were reconstructed (FIG. 1B; results summarized in Table 2), with only 2 gaps remaining (one on chromosomes 1 and 4 each). A ribosomal DNA (rDNA) repeat sequence was present in the assembly as a separate contig of 7450 bp, with exceptionally high coverage (328.8 fold). Given that sequence coverage all over the assembly very closely approximates 20×, it has been interpreted that there are approximately 16 copies of the rDNA repeat region, thus accounting for about 119 kbp in sequence. These rDNA loci were detected on all chromosomes (Example 1, FIG. 1B and FIG. 5A). The rDNA locus contains the 18S, 5.8S and 26S rRNA coding sequences. Unlike the *S. cerevisiae* 5S rRNA, which is present in the repeated rDNA locus, the 21 copies of the *P. pastoris* 5S ribosomal RNA (rRNA) were found to spread across the chromosomes. While the chromosomes of *P. pastoris* GS115 were estimated to be (from chromosome 1 to 4): 2.9, 2.6, 2.3 and 1.9 Mbp based on pulsed-field gel electrophoresis (PFGE)[38], it was estimated after assembly in this invention to be 2.88 (2.8+0.08), 2.39, 2.24 and 1.8 (1.78+0.017) Mbp. Including the estimated 0.12 Mbp of rRNA repeats, the genome size of *P. pastoris* was determined to be 9.43 Mbp. The *P. pastoris* genomic sequences are deposited in Genbank.

Genome Sequence Accuracy Estimation

A concern with genome sequences largely generated through 454 sequencing was the potential for "indel errors" at homopolymeric sequences[39]. An analysis of the occurrence of such sequences in the *P. pastoris* genome was conducted. Two approaches were followed to estimate the accuracy of the genome sequence. First, 39 peer-reviewed Genbank coding sequences of *P. pastoris* strain GS115 were retrieved (Table 3; a total sequence length of 70,295 bp). These sequences were compared to the genome sequence of this invention, and 84 differences were encountered. To determine which sequence was correct, PCR was performed on GS115 genomic DNA and the amplificates were Sanger-sequenced. In all but 2 cases, the Sanger sequences confirmed the genome sequence of this invention, and thus the error rate was estimated to be 1 in 35,147 bp. In an alternative approach, all open reading frames encoding proteins with at least one clear homolog in the databases were analyzed. If an interrupted ORF was found to have clear homology to the 5' part of the homologs, immediately followed by a coding sequence with clear homology to the 3' part, the most logical interpretation would be that there was a frame-shift error mutation in the genome sequence (i.e. both coding sequences are extremely likely to be linked into one open reading frame (ORF)). On this premise, frameshift errors were found in 2.7% (106) of the 3,997 genes for which such analysis could be made, totaling 6.11 Mbp of coding sequence. Assuming (fairly conservatively) that such error would have been detected if it has occurred in the first ⅔ of the ORF, a frame-shift error rate in the coding sequences was determined to be 1 in 37,716 bp. Both of the approaches above show that high-coverage 454 sequencing indeed yielded highly accurate genome sequences.

Pichia Pastoris Phylogenetic Position

Phylogenetic analysis (FIG. 1C; Example 1) shows that *P. pastoris* diverged before the formation of the CTG clade (yeasts which translate the CUG codon into serine instead of leucine[13]).

Genome Sequence Annotation: Protein-Coding Genes

Protein-coding genes were automatically predicted using the EuGene[18] prediction platform (Example 1) and these gene models were manually curated for functional annotation, accurate translational start and stop assignment, and intron location. This resulted in a 5,313 protein-coding gene set of which 3,997 (75.2%) were found to have at least one homolog in the National Center for Biotechnology Information (NCBI) protein database (BLASTP e-value 1e-5, sequence length ≦20% difference and sequence similarity ≧50%). The protein-coding genes were found to occupy 80% of the genome sequence. According to recently proposed measures for genome completeness, the genome was searched for highly conserved single (or low) copy gene sets: CEG with 248 genes across six model organisms[15], and FUNYBASE[16] with 246 genes with orthologs in 21 fungi. All genes from both gene-sets were found to be present in our proteome with full domain coverage.

In accordance with this invention, 1,285 genes were assigned to the Kyoto Encyclopedia of Genes and Genomes (KEGG) metabolic pathways[40], and 4,262 of genes were annotated with Gene Ontology (GO) terms[25,41]. The GO slim categories of *P. pastoris* are presented in FIG. 6. A secretion signal peptide was predicted in 9% of the genes[42] and 4,274 of proteins were predicted to contain InterPro domains[23]. These include 2,320 distinct Pfam domains. In comparing the presence and absence of protein domains with five other yeasts proteomes, 32 domains in 32 genes were identified as specific to *P. pastoris*. The two fungi in the CTG clade of which the genomes have been sequenced (*P. stipitis* and *C. lusitaniae*) share 71 gene families which were found to be absent in *P. pastoris*.

Codon (pair) optimization of transgenes to the expression host organism often yields substantial improvements in recombinant protein yield[43]. *P. pastoris*' codon usage is shown in FIG. 3A. Overall, the codon usage is similar to the one for *S. cerevisiae* (the same codons being preferred by both organisms for all amino acids). Some synonymous codon pairs are also more or less frequently used than expected (the "codon pair bias"). As previously reported for *S. cerevisiae*[44], underrepresented and overrepresented codon pair clusters were observed.

Genome Sequence Annotation: tRNA Genes tRNA coding genes were automatically predicted and manually confirmed by BLASTN with *S. cerevisiae* homologs, which identified 123 nuclear tRNA genes (Table 4), compared to 274 in the *S. cerevisiae* genome[45]. *P. pastoris* has three tRNA families not present in *S. cerevisiae* (tR(UCG), tL(CAG) and tP(CGG)), but also lacks one tRNA family (tL(GAG)).

Interestingly, a positive correlation was found between the number of tRNA genes for a given codon and the frequency of use of this codon (Spearman rho=0.88; P<0.0001, FIG. 3C).

EXAMPLE-3

This Example describes experiments conducted to test whether overexpression in engineered Glycoswitch *Pichia pastoris* an endogenous UDP-GlcNAc transporter, UDP-Gal transporter and UDP-Glc-4-epimerase can increase glycan conversion efficiency of these strains, thus resulting in more uniform glycosylation patterns.

Results

Expression vectors for these three genes as described in the experimental procedures below. In these vectors, the transporter or epimerase gene was placed under control of the AOX1 promoter. Selection of these vectors was based on G418 (for UDP-GlcNAc transporter) or hygromycin (for UDP-Gal transporter and UDP-Glc-4-epimerase).

These vector were transformed into GSGnM5 (UDP-GlcNAc transporter) or GSGalGnM5 (UDP-Gal transporter and UDP-Glc-4-epimerase). Clones for all three strains were methanol induced and relative contribution of the glycans was assessed (Table 7). Similar results were obtained using clones from a separate transformation.

It is possible that overexpression of these genes can have a beneficial influence on the glycan conversion efficiency in fermentation conditions.

Experimental Procedures:

Strains and growth conditions—*Escherichia coli* MC1061 was used as the host strain for all molecular experiments. *E. coli* was cultivated in LB medium containing the appropriate antibiotics for selection. The *Pichia pastoris* GlycoSwitch GnMan5 and GalGnMan5 strains expressing recombinant human alfa-antitrypsin were used in this analysis. TheGn-Man5 strain is a GS115 (Invitrogen, Carlsbad, Calif., USA)—derived strain that modifies its glycoproteins predominantly with GlcNAcMan5GlcNAc2 N-glycans due to inactivation of Och1 and overexpression of an ER-localized *T. reesei* α-1,2-mannosidase and a Golgi-localized human GlcNAc transferase. The GalGnM5 strain was derived from the GnM5 strain by transformation of the latter with a Golgi-localized human Galactosyl transferase fused to the *S. cerevisiae* UDP-Glc-4-epimerase Gal10. This strain predominantly modifies its glycoproteins with GalGlcNAcMan5GlcNAc2 N-glycans. *Pichia pastoris* cultures were grown in YPD medium, minimal medium or BMGY and induced in BMMY medium. All *Pichia pastoris* media were prepared as described in the *Pichia* instruction manual (Invitrogen, Carlsbad, Calif., USA).

Vector construction—All molecular experiments were carried out according to standard procedures (Sambrook et al., 1989). Phusion polymerase was used in PCR reactions according to manufacturer's instructions (Finnzymes, Espoo, Finland). To construct the expression vectors for the activated sugar transporters (UDP-GlcNAc transporter and UDP-Gal transporter) and the UDP-Glucose-4-epimerase, the genes were amplified by PCR on genomic DNA. The primers for the PCR reaction were designed to amplify the complete gene with the stop codon and to incorporate a SaIt site downstream of UDP-GlcNAcT and a BstBI restriction site upstream and a NotI site downstream of the UDP-GalT and UDP-Glc-4-epimerase genes to allow subcloning. After amplification, the genes were cloned into pCR®4Blunt-TOPO® (Invitrogen, Carlsbad, Calif., USA) and sequenced. After BstBI/NotI digestion the UDP-GalT and UDP-Glc-4-epimerase genes were ligated into the pPICHygMnn2DmManII vector in which the Mnn2-ManII fusiongene was removed by BstBI/NotI digest. Similarly, UDP-GlcNAcT was cut from the TOPO clone by BstBI/SalI digest and ligated into the pPICKanMnn2SpGal10hGalT vector in which the Mnn2-Gal10-GalT fusiongene was removed by BstBI/SalI digest. After selection of good clones, the expression vectors are opened by PmeI or SalI digest for transformation of *Pichia pastoris* strains. Insertion of the vector in the *Pichia pastoris* genome of PmeI opened vectors were expected to be targeted to the AOX1 promoter locus while SalI opened vectors were expected to insert in the gene of interest.

Yeast treatments—Cells were grown in 5 ml BMGY medium at 30° C. After 48 h of incubation, the medium of the cultures was replaced by BMMY. The induction was performed for 48 h by spiking the cultures twice a day with 1% methanol. The cultures were harvested by centrifugation for 5 minutes at 3000 g. Medium and cell pellet were frozen at −20° C.

Glycosylation analysis—N-linked glycans were analysed using DNA sequencer-assisted fluorophore-assisted carbohydrate electrophoresis (DSA-FACE) as described previously (Laroy et al., 2006).

EXAMPLE-4

This Example describes experiments conducted to test the effect of overexpression of chaperone genes identified hereinabove on yield of heterologous proteins.

Results

Of the endogenous chaperone genes in the genome of *Pichia pastoris*, three ER-resident chaperones were selected for testing: ROT1, SHR3 and SIL1. Expression vectors for these genes were generated as described in the experimental procedures. In these vectors, the chaperone genes are under control of the GAP promoter.

For transformation of these vectors into the GlycoSwitch Man5 strain, two approaches were used. In the first approach, the construct were targeted to the GAP promoter by linearization of the vectors with AvrII. In the second approach, random integration was achieved by linearization of the vectors with EcoRV. Transformants were selected on medium containing 100 μg/ml nourseothricin. Clones for all three chaperone constructs, in both transformations, were grown and intra-cellular proteins were extracted and run on SDS-PAGE gel. For detection of chaperone expression, a Western blot analysis was performed using an antibody against the His-tag. Expression was shown for ROT1 (31 kDa) and SHR3 (28 kDa). No expression could be observed for SIL1 (44 kDa).

To analyse the effect of the chaperones on heterologous expression and secretion of IL10 and IFN-β, two approaches were followed. In the first approach, the GSM5 strains expressing the chaperone were transformed with an IL10- or IFNβ-expression plasmid. In the second approach, GSM5 strains expressing IL10 or IFN-b were transformed with expression vectors for ROT1 or SHR3. ROT1- or SHR3-expressing GSM5 strains were transformed with pPIC92mIL10, linearized with StuI or with pPIC9MFhIFNb2, linearized with BstBI. Individual clones were isolated on minimal medium and used for expression experiments. Secretion of IL10 or IFN-β in the medium upon methanol induction was assessed by SDS-PAGE and Coomassie Brilliant Blue staining.

IL10 or IFN-β expressing GSM5 strains were transformed with pGAPNORPpROT1 or with pGAPNORPpSHR3, both linearized with EcoRV. Individual clones were selected on nourseothricine plates and used for induction experiments.

Upon overexpression of ROT1 or SHR3, no significant enhancement of the secretion of IL10 or IFN-β was observed, in comparison with control clones expressing IL10 or IFN-β.

In the ROT1-expressing strains, somewhat more of a 31 kDa protein was detected in the medium. To test whether some of the tagged ROT1 proteins were secreted upon overexpression, Western blot-immunodetection was performed using anti-His antibodies. In both the media of the control strain and the ROT1 or SHR3-expressing strains, a faint band of approximately 31 kDa could be detected. Moreover, upon deglycosylation with PNGaseF, part of this band shifted to a faster migrating band. It was therefore concluded that this band is not related to ROT1.

Generation of expression vectors for the *P. pastoris* homologues of LHS1, CNE1 and EPS1 was also underway. Upon PCR amplification of the chaperone genes on *P. pastoris* genomic DNA, the PCR product for EPS1 (1945 bp) was cut with EcoRI and Non and ligated into the vector fragment of pGAPNORPpROT1, cut with the same enzymes and transformed to *E. coli*. Because the genes for CNE1 and LHS1 contain EcoRI sites, the CNE1 (1753 bp)- and LHS1 (2700 bp)-PCR products were fused by PCR with the GAP promoter DNA of pGAPNORPpROT1 (500 bp). The resulting PCR-DNA was then cut with NotI and NsiI (CNE1) or with NotI and AvrII (LHS1) and ligated with the vector fragment cut with the same enzymes and transformed to *E. coli*. Clones were checked by colony-PCR for the presence of chaperone containing plasmids. Once completed, the coding sequences for these chaperones would be fused with a C-terminal myc/His6 tag (His6 tag disclosed as SEQ ID NO: 438) and placed under control of the GAP promoter. The resulting plasmids would also confer resistance to nourseothricine.
Experimental Procedures Strains and growth conditions—*Escherichia coli* MC1061 was used as the host strain for all molecular experiments. *E. coli* was cultivated in LB medium containing the appropriate antibiotics for selection. The *Pichia pastoris* GlycoSwitch GnMan5 and GalGnMan5 strains expressing recombinant human alfa-antitrypsin were used in this analysis. ThcGnMan5 strain is a GS115 (Invitrogen, Carlsbad, Calif., USA)— derived strain that modifies its glycoproteins predominantly with GlcNAcMan5GlcNAc2 N-glycans due to inactivation of Och1 and overexpression of an ER-localized *T. reesei* α-1,2-mannosidase and a Golgi-localised human GlcNAc transferase. The GalGnM5 strain was derived from the GnM5 strain by transformation of the latter with a Golgi-localized human Galactosyl transferase fused to the *S. cerevisiae* UDP-Glc-4-epimerase Gal10. This strain predominantly modifies its glycoproteins with GalGlcNAcMan5GlcNAc2 N-glycans. *Pichia pastoris* cultures were grown in YPD medium, minimal medium or BMGY and induced in BMMY medium. All *Pichia pastoris* media were prepared as described in the *Pichia* instruction manual (Invitrogen, Carlsbad, Calif., USA).

Vector construction—All molecular experiments were carried out according to standard procedures (Sambrook et al., 1989). Phusion polymerase was used in PCR reactions according to manufacturer's instructions (Finnzymes, Espoo, Finland). To construct the expression vectors for the chaperone genes Sil1, Rot1 and Shr3, the chaperone genes were amplified by PCR on genomic DNA. The primers for the PCR reaction were designed to amplify the complete gene without the stop codon and to incorporate an EcoRI restriction site upstream and a NotI site downstream of the gene to allow subcloning. Ater amplification, the genes were cloned into pCR®4Blunt-TOPO® (Invitrogen, Carlsbad, Calif., USA) and sequenced. After EcoRI/NotI digestion the chaperon genes were inserted into the pGAPNOURCre vector in which the Cre recombinase gene was removed by EcoRI/NotI digest. This created a transcriptional fusion of the chaperon gene with a myc and His6 tag (SEQ ID NO: 438). The pGAP-NOURCre vector was generated by deletion of the *Pichia* autosomal replication sequence (PARS) from the pGAPNorCre1PARS1 vector by NsiI digest and self ligation. After selection of good clones, the chaperone expression vectors were opened by AvrII or EcoRV digest for transformation of *Pichia pastoris* strains. Insertion of the vector in the *Pichia pastoris* genome of AvrII opened vectors was targeted to the Gap promoter locus while EcoRV opened vectors was inserted randomly.

Yeast treatments—Cells were grown in 5 ml BMGY medium at 30° C. After 48 h of incubation, the medium of the cultures was replaced by BMMY. The induction was performed for 48 h by spiking the cultures twice a day with 1% methanol. The cultures were harvested by centrifugation for 5 minutes at 3000 g. Medium and cell pellet were frozen at −20° C.

EXAMPLE-5

A set of 54 *P. pastoris* genes was identified that contain a signal sequence, as discussed hereinabove. The expression of these genes in *P. pastoris* was assessed using microarray data published by Graf et al. (2008)[48], the presence of these proteins in *P. pastoris* grown in glucose containing medium (Mattanovich et al., 2009)[50] and for the protein abundance of their homologues in *S. cerevisiae* (Brockmann et al., 2007[46]; Ghaemmaghami et al., 2003[47]; Liu et al., 2004[49]; Newman et al., 2006[51]) (Table 8).

Based on these data ten genes (13 *P. pastoris* sequences) were selected for further analysis. The efficiency of these signal sequences is assessed in comparison with the prepro sequence of α-mating factor (α-MF) to drive the secretion of N-terminally tagged human IL10 upon methanol induction. The human IL10 expression plasmid pKai61EA-hIL10 is used. In this plasmid the mature hIL10 sequence is preceded by the prepro sequence from α-MF, followed by a His6-tag (SEQ ID NO: 438) and a DEVD cleavage site (SEQ ID NO: 439). The His6-tag (SEQ ID NO: 438) facilitates the purification of the acid-labile IL10 protein and the DEVD cleavage site (SEQ ID NO: 439) makes it possible to remove this tag by incubation with purified caspase-3.

To facilitate the exchange of the α-MF prepro sequence with the signal sequences from the candidate genes, 13 synthetic genes are obtained that can be cut out using BstBI and KpnI and that contain the signal sequence of the candidate gene followed by His6-tag (SEQ ID NO: 438), DEVD-site (SEQ ID NO: 439) and part of the mature hIL10.

In a first attempt the BstBI-KpnI fragment of the synthetic genes was PCR amplified with specific primers and subsequently cut with BstBI and KpnI and ligated into the vector fragment of pKai61EA-hIL10, cut with the same enzymes. The ligation mixture was then used for transformation of *E. coli*. Individual clones selected on zeocine containing plates were checked by colony PCR. Candidate clones were already identified for chr1-4_0611 and chr1-4_0426.

EXAMPLE-6

The initializing step in yeast O-glycosylation is known to be catalysed by a family of protein mannosyltransferases (PMT). As described hereinabove, in the *Pichia pastoris* genome, 5 orthologs of the PMT genes were annotated, with representatives in the 3 subfamilies. In *S. cerevisiae*, deletion of only one of these genes was found to be insufficient to abolish O-glycosylation. The double and triple knockouts resulted in a loss of O-glycosylation but showed a severe defect in growth. In this Example, two approaches are described for generating PMT deficient *Pichia pastoris* strains which could result in an O-glycosylation deficient strain.

In one approach, disruptions of the PMT ORFs are made through the use of a knock-in vector by single homologous recombination. In the second approach, PMT knock-outs are made by double homologous recombination.
Experimental Procedures Strains and growth conditions—*Escherichia coli* competent strains are used as the host strain for all molecular experiments. *E. coli* is cultivated in LB medium containing the appropriate antibiotics for selection. The *Pichia pastoris* GS115 strain (Invitrogen, Carlsbad, Calif., USA) and glycoengineered strains are used in this analysis, which can express a protein of interest. *Pichia pastoris* cultures are grown in YPD medium, minimal medium or BMGY and induced in BMMY medium. All *Pichia pastoris* media are prepared as described in the *Pichia* instruction manual (Invitrogen, Carlsbad, Calif., USA).

Vector construction—All molecular experiments are carried out according to standard procedures (Sambrook et al., 1989). Phusion polymerase is used in PCR reactions according to manufacturer's instructions (Finnzymes, Espoo, Finland).

To construct knock-in vectors for the PMT genes, a fragment of these genes is amplified by PCR. The primers for the PCR reaction are designed to amplify a fragment that has low similarity to other regions in the genome, is not the full length gene, and is located so the protein fragment preceding the fragment is not functional. In addition, the primers contain restriction sites for subcloning of the fragment. In this fragment a restriction site, unique in the final vector, is incorporated to allow later linearization. After amplification, the genes are cloned into pCR®4Blunt-TOPO® (Invitrogen, Carlsbad, Calif., USA) and sequenced. This fragment is cloned into a *Pichia* vector containing a selectable marker. After selection of good clones, the PMT knock-in vectors are opened by restriction digest using the unique site in the PMT fragment for transformation of *Pichia pastoris* strains. Insertion of the vectors in the *Pichia pastoris* genome will be targeted to the respective PMT loci.

To construct knock-out vectors for the PMT genes, two fragments of the PMT loci are amplified by PCR, cloned into the pCR®4Blunt-TOPO® vector (Invitrogen, Carlsbad, Calif., USA) and sequenced. The primers for the PCR reaction are designed to amplify fragments within the PMT ORF, promoter or 5'UTR in a way that when these two fragments recombine with the PMT allele it will create an inactive allele. The primers contain restriction sites for subcloning of the fragments and a unique restriction site upstream of the 5' fragment and downstream of the 3' fragment. These fragments will be cloned into a *P. pastoris* vector up and downstream of a selectable marker. After selection of good clones, the PMT knock-out vectors are cut by restriction digest using the unique site incorporated into the PMT fragment, after which the excised fragment will be used for transformation of *Pichia pastoris* strains.

EXAMPLE-7

The stability of certain proteins expressed in *Pichia pastoris* has been observed to be influenced by the action of proteases such as protease A and B. As described above, in the *Pichia pastoris* genome, a series of orthologs of novel protease genes were identified and annotated, with representatives in the serine protease, aspartyl protease and cysteine protease subfamilies. One strategy is described in this example to generate a series of strains of *Pichia pastoris* deficient in one or more of the identified protease activities. This strategy can be applied to any strain of *Pichia pastoris* that expresses a heterologous protein to compare the stability of that heterologous protein with or without the particular protease being active. One application of this strategy is to take a strain that expresses a protein of interest and use a set or "kit" of the insertional inactivation ("knock-in") vectors to generate a series of derivative strains that each lack activity of one of the endogenous proteases of *Pichia*.

To generate protease deficient *P. pastoris* strains, two we describe two approaches, one generates a disruption of the individual protease ORFs through knock-in of the vector by single homologous recombination. The second approach generates true protease knock-outs by double homologous recombination.

Experimental Procedures

Strains and growth conditions—*Escherichia coli* competent strains are used as the host strain for all molecular experiments. *E. coli* is cultivated in LB medium containing the appropriate antibiotics for selection. The *Pichia pastoris* GS115 strain (Invitrogen, Carlsbad, Calif., USA) or glycoengineered strains are used in this analysis, these strains can express a protein of interest. *Pichia pastoris* cultures are grown in YPD medium, minimal medium or BMGY and induced in BMMY medium. All *Pichia pastoris* media are prepared as described in the *Pichia* instruction manual (Invitrogen, Carlsbad, Calif., USA).

Figure 8:
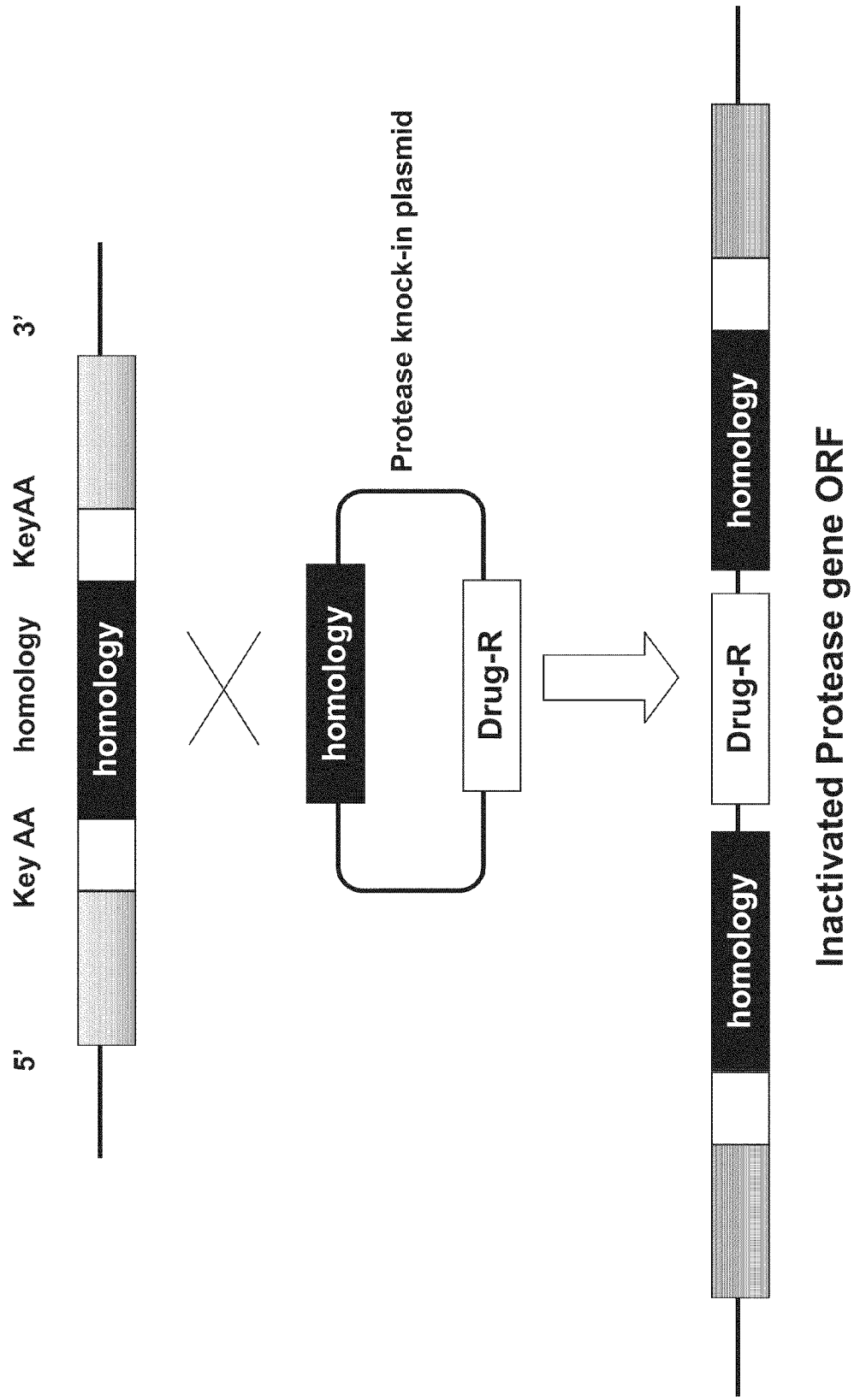
FIG. 8. Protease Gene Insertional Inactivation Strategy. A drug resistance marker or other auxotrophic marker can be used for this method.

Vector construction—All molecular experiments are carried out according to standard procedures (Sambrook et al., 1989). Phusion polymerase is used in PCR reactions according to manufacturer's instructions (Finnzymes, Espoo, Finland). To construct the knock-in vectors for the protease genes, a fragment of the corresponding gene is amplified by PCR. The primers for the PCR reaction are designed to amplify a fragment that has low similarity to other regions in the genome, is not the full length gene, and is located so the protein fragment preceding the fragment is not functional. This is readily achieved by using segments of the gene that lie within the highly conserved DNA/protein motifs that correspond to essential amino acid residues in the active site of that particular class of protease. In addition, the primers contain restriction sites for subcloning of the fragment. In this fragment a restriction site, unique in the final vector, is incorporated to allow later linearization. After amplification, the genes are cloned into pCR®4Blunt-TOPO® (Invitrogen, Carlsbad, Calif., USA) and sequenced. This fragment is cloned into a *Pichia* vector containing a selectable marker. After selection of good clones, the protease knock-in vectors are opened by restriction digest using the unique site in the protease fragment for transformation of *Pichia pastoris* strains. Insertion of the vectors in the *Pichia pastoris* genome are targeted to the respective protease gene loci. FIG. 8 shows the DNA sequences for one strategy of protease inactivation by knock-in.

To construct the knock-out vectors for the protease genes, two fragments of the protease loci are amplified by PCR, cloned into the pCR®4Blunt-TOPO® vector (Invitrogen, Carlsbad, Calif., USA) and sequenced. The primers for the PCR reaction are designed to amplify fragments within the protease ORF, promoter or 5'UTR in such a way that when these two fragments recombine with the protease allele it creates an inactive allele. The primers contain restriction sites for subcloning of the fragments and a unique restriction site upstream of the 5' fragment and downstream of the 3' fragment. These fragments are cloned into a *P. pastoris* vector up and downstream of a selectable marker. After selection of good clones, the protease knock-out vectors are cut by restriction digest using the unique site incorporated into the protease fragment, after which the excised fragment is used for transformation of *Pichia pastoris* strains. In this way, more stable gene knock-out constructs are generated.

REFERENCES

1. Hamilton, S. R. & Gerngross, T. U. Glycosylation engineering in yeast: the advent of fully humanized yeast. *Curr. Opin. Biotechnol.* 18, 387-392 (2007).
2. Jacobs, P. P., Geysens, S., Vervecken, W., Contreras, R. & Callewaert, N. Engineering complex-type N-glycosylation in *Pichia pastoris* using GlycoSwitch technology. *Nat. Protoc.* 4, 58-70 (2009).
3. Ratner, M. Pharma swept up in biogenerics gold rush. *Nat. Biotechnol.* 27, 299-301 (2009).
4. Potgieter, T. I. et al. Production of monoclonal antibodies by glycoengineered *Pichia pastoris*. *J. Biotechnol.* 139, 318-325 (2009).
5. Mogelsvang, S., Gomez-Ospina, N., Soderholm, J., Glick, B. S., Stachelin, L. A. Tomographic evidence for continuous turnover of Golgi cisternae in *Pichia pastoris*. *Mol. Biol. Cell* 14, 2277-2291 (2003).

6. Hartner, F. S. et al. Promoter library designed for fine-tuned gene expression in *Pichia pastoris*. *Nucleic Acids Res.* 36, e76 (2008).
7. Vervecken, W. et al. In vivo synthesis of mammalian-like, hybrid-type N-glycans in *Pichia pastoris*. *Appl. Environ. Microbial.* 70, 2639-2646 (2004).
8. Bobrowicz, P. Engineering of an artificial glycosylation pathway blocked in core oligosaccharide assembly in the yeast *Pichia pastoris*: production of complex humanized glycoproteins with terminal galactose. *Glycobiology* 14, 757-766 (2004).
9. Trimble, R. B. et al. Characterization of N- and O-linked glycosylation of recombinant human bile salt-stimulated lipase secreted by *Pichia pastoris*. *Glycobiology* 14, 265-274 (2004).
10. Mille, C., et al. Identification of a new family of genes involved in beta-1,2-mannosylation of glycans in *Pichia pastoris* and *Candida albicans*. *J. Biol. Chem.* 283, 9724-9736 (2008).
11. Dalle, F. et al. Beta-1,2- and alpha-1,2-linked oligomannosides mediate adherence of *Candida albicans* blastospores to human enterocytes in vitro. *Infect. Immun.* 71, 7061-7068 (2003).
12. Nasab et al., *Mol Biol Cell*. 19:3758-68, 2008.
13. *Glycobiology* 12(12): 821-828, 2002.
14. *Pichia Protocols. Methods in Molecular Biology* 103, 27-39, 1998.
15. Higgins and Cregg, *Pichia Protocols. Methods in Molecular Biology* 103, 1-16, 1998.
16. Margulies, M. et al. Genome sequencing in microfabricated high-density picoliter reactors. *Nature* 437, 376-380 (2005).
17. Pop, M., Kosack, D. S. & Salzberg, S. L. Hierarchical scaffolding with Bambus. *Genome Res.* 14, 149-159 (2004).
18. Foissac, S. et al. Genome Annotation in Plants and Fungi: EuGene as a Model Platform. *Current Bioinformatics* 3, 89-97 (2008).
19. Wang, K., Ussery, D. W. & Brunak, S. Analysis and prediction of gene splice sites in four *Aspergillus* genomes. *Fungal Genet. Biol.* 46 Suppl 1, S14-18 (2009).
20. Ter-Hovhannisyan, V., Lomsadze, A., Chernoff, Y. & Borodovsky, M. Gene prediction in novel fungal genomes using an ab initio algorithm with unsupervised training. *Genome Res.*, 13 (2008).
21. Stanke, M. et al. Gene prediction in eukaryotes with a generalized hidden Markov model that uses hints from external sources. *BMC Bioinformatics* 7, 62 (2006).
22. The Universal Protein Resource (UniProt) 2009. *Nucleic Acids Res.* 37, D169-174 (2009).
23. Pruitt, K. D., Tatusova, T. & Maglott, D. R. NCBI reference sequences (RefSeq): a curated non-redundant sequence database of genomes, transcripts and proteins. *Nucleic Acids Res.* 35, D61-65 (2007).
24. Mulder, N. J. et al. New developments in the InterPro database. *Nucleic Acids Res.* 35, D224 (2007).
25. Ashburner, M. et al. Gene ontology: tool for the unification of biology. The Gene Ontology Consortium. *Nat. Genet.* 25, 25-29 (2000).
26. Edgar, R. C. MUSCLE: multiple sequence alignment with high accuracy and high throughput. *Nucleic Acids Res.* 32, 1792-1797 (2004).
27. Parra, G., Bradnam, K., Ning, Z., Keane, T. & Korf, I. Assessing the gene space in draft genomes. *Nucleic Acids Res.* 37, 289-297 (2009).
28. Marthey, S. et al. FUNYBASE: a FUNgal phYlogenomic dataBASE. *BMC Bioinformatics* 9, 456 (2008).
29. Griffiths-Jones, S. et al. Rfam: annotating non-coding RNAs in complete genomes. *Nucleic Acids Res.* 33, D121-124 (2005).
30. Lowe, T. M. & Eddy, S. R. tRNAscan-SE: a program for improved detection of transfer RNA genes in genomic sequence. *Nucleic Acids Res.* 25, 955-964 (1997).
31. Pinheiro, M. et al. Statistical, computational and visualization methodologies to unveil gene primary structure features. *Methods Inf. Med.* 45, 163-168 (2006).
32. Schmidt, H. A., Strimmer, K., Vingron, M. & von Haeseler, A. TREE-PUZZLE: maximum likelihood phylogenetic analysis using quartets and parallel computing. *Bioinformatics* 18, 502-504 (2002).
33. Rossignol, T. et al. CandidaDB: a multi-genome database for *Candida* species and related *Saccharomycotina*. *Nucleic Acids Res.* 36, D557-D561 (2007).
34. Jeffries, T. et al. Genome sequence of the lignocellulose-bioconverting and xylose-fermenting yeast *Pichia stipitis*. *Nat. Biotechnol*, 25, 319-326 (2007).
35. Enright, A. J., Van Dongen, S. & Ouzounis, C. A. An efficient algorithm for large-scale detection of protein families. *Nucleic Acids Res.* 30, 1575 (2002).
36. Finn, R. et al. The Pfam protein families database. *Nucleic Acids Res.* 36, D281 (2008).
37. Felsenstein, J. Inferring phylogenies from protein sequences by parsimony, distance, and likelihood methods. *Methods Enzymol.* 266, 418-427 (1996).
38. Ohi, H., Okazaki, N., Uno, S., Miura, M. & Hiramatsu, R. Chromosomal DNA patterns and gene stability of *Pichia pastoris*. *Yeast* 14, 895-903 (1998).
39. Huse, S. M., Huber, J. A., Morrison, H. G., Sogin, M. L. & Welch, D. M. Accuracy and quality of massively parallel DNA pyrosequencing. *Genome Biol.* 8, R143 (2007).
40. Kanehisa, M. et al. KEGG for linking genomes to life and the environment. *Nucleic Acids Res.* 36, D480 (2008).
41. Schmid, R. & Blaxter, M. annot8r: GO, EC and KEGG annotation of EST datasets. *BMC Bioinformatics* 9, 180 (2008).
42. Emanuelsson, O., Brunak, S., von Heijne, G. & Nielsen, H. Locating proteins in the cell using TargetP, SignalP and related tools. *Nat. Protoc.* 2, 953-971 (2007).
43. Hu, S. et al. Codon optimization, expression, and characterization of an internalizing anti-ErbB2 single-chain antibody in *Pichia pastoris*. *Protein Expr. Purif*: 47, 249-257 (2006).
44. Friberg, M., von Rohr, P. & Gonnet, G. Limitations of codon adaptation index and other coding DNA-based features for prediction of protein expression in *Saccharomyces cerevisiae*. *Yeast* 21, 1083-1093 (2004).
45. Hani, J. & Feldmann, H. tRNA genes and retroelements in the yeast genome. *Nucleic Acids Res.* 26, 689-696 (1998).
46. Brockmann et al. (2007) *PLoS Computational Biology* 3, e57.
47. Ghaemmaghami et al. (2003) *Nature* 425, 737.
48. Graf et al. (2008) *BMC Genomics* 9, 390.
49. Liu et al. (2004) *Anal Chem* 76, 4193.
50. Mattanovich et al. (2009) *Microbial Cell Factories* 8, 29.
51. Newman et al. (2006) *Nature* 441, 840.

TABLE 1

Primers used in the genome assembly process. The sequences listed under "Primers used for sequencing" are designated as SEQ ID NOS: 836-889, respectively, in order of appearance. The sequences listed under "Primers used for probes" are designated as SEQ ID NOS: 890-913, respectively, in order of appearance. The sequences listed under "Primers used for fragment joining" are designated as SEQ ID NOS: 914-927, 436, and 437, respectively, in order of appearance.

5' Primers used for sequencing 3'

| | |
|---|---|
| 13 | CCTATTCTCTCTTATCCCGACG |
| 16 | GAAGGTTTATCGGCAACATC |
| 29 | GGAAGATGCAGAGGATGTTAGG |
| 30 | AGGTTATACTGTGTGTAGTACAGATGG |
| 33 | CATCTATAACGAGTCAAAGGATGA |
| 35 | TGGAGTGAATGGAAGTTCAGAG |
| 36 | GATTAGCTAAGTTGCCCTATTAGG |
| 37 | AAATTGTCGTTCTCACAACAGG |
| 38 | CATCTTAAGAATACATCATATGCACC |
| 39 | CCATGTTGCACTCACACTTGG |
| 40 | CGTTGAGTAGCTTTCTCCTGTCC |
| 41 | TATCACTCCATATGGCTCTTGG |
| 42 | GTAGAGTAGCTGACCTAAAGTCTTGG |
| 43 | AAGCCGTAGAGGAGTGTAAACG |
| 48 | GAACTTCAACTGTCATTATTGATGG |
| 49 | CAGGCATCTTCAGAGGGTACTC |
| 50 | TTCCTGTGGCAGATATCAGCT |
| 51 | GAGAGTACTAACGATTCTTCACTCACT |
| 52 | TTACCAATCACGTAGTTCGCTC |
| 53 | GACTTCTAACGGGTGAGATATCC |
| 54 | TAGGTCAGTGCTTGATTGTAATCTC |
| 55 | AATCGACAGGGATTGCTCAA |
| 56 | ACACAAGGAGTTAGGGTACTAAGC |
| 57 | CCACTTTGAGTTCCTTGATCTCAC |
| 58 | CATTGACACTCCTTACAATGTGC |
| 63 | TTTGCGAGTTCATGAAGAAGAGG |
| 64 | GAGTGGTATCAGAAACTTCAGATG |
| 65 | GACCCTGGTAGTCTCAATCTAAG |
| 66 | CTCACCATATAAGATTTATTCTGATAAAGC |
| 67 | GCTCAACTTTCTGAACTTGCTCA |
| 68 | CATCAAAGTCCAGTAAGCAACCC |
| 69 | GGAGCTGTGTTATTTACTATTGAGG |
| 70 | ATGATTTCGAAAGGTTCTACCCC |
| 71 | TACTAACTTTGAGTTTAGAGGATGG |
| 72 | AGGGAAGTCTAAGTTCTTTCGC |
| 73 | GATGATAACGGTGCCTGGTTCA |
| 74 | GTATACCAGTTTCCCAACAATCTTAG |
| 75 | GGGGTTGGAATTTGCTCGATAA |
| 76 | TACAGATGAATCTGGGTCGGTG |
| 77 | CTGOTACTTACGAAACCACGTA |
| 78 | TTTCGTAAGTACCAGTCCATGG |
| 79 | GTGGTAGCTGGGGTGGTT |
| 80 | TCTGTCTAATGCTTACCATCAGC |
| 81 | CCCTCTGTCGATCTCAGGTTT |
| 82 | CTGAACAGCATTGAAGATAAAAAACG |
| 83 | CAGAAGTTTATGGCTGATATGATGC |
| 84 | GATAGTGGTGTTGGGAGGATATG |
| 85 | AGAATGATTTGGGAGATACGAGC |
| 86 | GCTGCCCTTTGAGTATCAGATC |
| 87 | GCTGGCCAATCTCATCTCATG |
| 88 | GGAAGGATTTGGGCTAATAAACTG |
| 115 | CAACTATCCACTTGCTCATAACAGAC |
| 116 | CCTACAGGGTTTCCATGTGATG |
| 117 | GGTAAGATGAACTAATTCACAAGGTG |

5' Primers used for probes 3'

| | |
|---|---|
| Chr1 | ATCGACTGAGCTTCAAGTTAATGTGC |
| | TTCAAGCAGTCTCCATCACAATCC |
| Chr2 | ACTCTGGTGGAGTAACCGTACTCG |
| | ATTGTCTCCAATGCTTCTTGTACTACC |
| Chr3 | CTACGATTATGATGTCAGTGCCAGTG |
| | GTGAGAACAACTAAAGAATTATTGGAGC |
| Chr4 | TAGCACGGTAGATCTTGTGACTTGG |
| | GTAGAAGAGCCATTGTTCCATGTG |
| FragB | GCTTGCAGAAGATGATTACAAACTTGC |
| | GACTGAACTTGTTGGATGTCTAAGGAG |
| FragD | TCTATACAATGTCCAAGTGGACCAAG |
| | GTTTCTTCGACGAACGATGATCC |

TABLE 1-continued

Primers used in the genome assembly process. The sequences listed under "Primers used for sequencing" are designated as SEQ ID NOS: 836-889, respectively, in order of appearance. The sequences listed under "Primers used for probes" are designated as SEQ ID NOS: 890-913, respectively, in order of appearance. The sequences listed under "Primers used for fragment joining" are designated as SEQ ID NOS: 914-927, 436, and 437, respectively, in order of appearance.

| | |
|---|---|
| C2 | AGCACGACGGAGTCTAAGATTCC |
| | GTCAGAGGTGAAATTCTTGGATCG |
| C34 | TATGTCTTCTCCTGTTGTTCCTACCTCC |
| | CGGAATCAATGATTAGCTCATTGG |
| C121 | GAATTCAGATGCTGATTTACTTGCAC |
| | TGGATAAGCAATGGAGGAAGTTCTG |
| C131 | CATTAGTAGGAGCTTCCAAGGTACTGT |
| | AGTCCGTGGCAATAGAGCGATTG |
| C157 | TCACCAAGAAAGCTCTTATTTGGAGAG |
| | ATTTCAGTCTCGCATTGTCCGACT |
| C159 | CAAAGAAGCTAGCTGTGGATGGAG |
| | AACTGTAGGAACTCCATTCATCGGTG |

5' Primers used for fragment joining 3'

| | |
|---|---|
| 1 | CGTTTAACGTCGATAGGCTAG |
| 2 | CAGCAGTCAGACCCTTAATGTC |
| 4 | GCAGAAAAGTTACCAAGTGAGC |
| 5 | TCGTGCCATGGTAGTATTCCT |
| 6 | TCTCAAACTGTTCAAAGACTTGTAC |
| 8 | TAATGAAGGACAAATAATTTCAGC |
| 9 | TGTTCACATAGCCAACTGATACTG |
| 62 | GGCCGGGAATGCTATTTGGT |
| 60 | TTTGGCATTATGCGAAAAGAATAGGAC |
| 12 | GCAAGCTATTGGAAACAACC |
| 15 | ATTTTGATAGGAAGCTTAGATTGC |
| 17 | CCAACTCGTGACAACAACCTC |
| 21 | GCCACCAACTTCAGTAGTCCAC |
| 23 | CCTTAGAAGTCGTTATATGGAAGTG |
| 25 | ATACGCATGTGGAGATTCCTC |
| 26 | CTCTCATCCAACCAGTTGACC |

TABLE 2

A. Genome sequencing and assembly statistics

454 Sequencing

| Sequenced Reads | Sequenced Length (bp) | Paired-end reads |
|---|---|---|
| 897,197 | 218,602,026 | 11,538 |

MIRA assembly

| Assembled reads | Assembled Contigs | Contigs (>500 bp) | Length (bp) | N50 | L50 (Kbp) | Average coverage |
|---|---|---|---|---|---|---|
| 885,659 | 1,154 | 230 | 9,658,092 | 40 | 77 | 20 |

Contig joning

| Joined contigs | Supercontigs | Length (Mbp) | Chromosomes |
|---|---|---|---|
| 203 | 10 | 9.3 | 4 |

B. Genome Contents Overview

General information

Size (Mbp): 9.3 (not including rDNA loci, estimated at 0.12 Mbp)
Genome GC content (%): 41.1
Assembled chromosomes: 4
Coding genes Coding genes: 5,313
Coding %: 79.6
Coding GC (%) 41.6

TABLE 2-continued

Mean gene length (bp) 1,442

Single exon genes: 4,680

RNA genes tRNA genes: 123

5s rRNA genes: 21

Mitochondrial genome

Size (bp): 36,119

Genome GC content (%): 22

Coding genes: 16 tRNA genes: 31

N50: number of contigs that collectively cover at least 50% of the assembly.

L50: length of the shortest contig among those that collectively cover 50% of the assembly

TABLE 3

Resequencing of selected known *P. Pastoris* ORFs.
Comparison of sequence differences between our 454 sequence and the
ORF of genes present in Genbank. The genes containing sequence difference
and our 454 sequence are given in the last column.

|    | Gene Name | Locus id | CDS (bp) | Differences Genbank | Differences Sanger |
|----|-----------|----------|----------|---------------------|--------------------|
| 1  | Cyc | chr4_0018 | 333 | 0 | |
| 2  | Delta 15-fatty acid desaturase | chr4_0743 | 1248 | 5 | 0 |
| 3  | YPS2 | chr3_0299 | 1584 | 0 | |
| 4  | PFK3 | chr4_0943 | 1056 | 1 | 0 |
| 5  | FET3 | chr2-1_0787 | 1890 | 5 | 0 |
| 6  | EF-1 | FragB_0052 | 1380 | 5 | 0 |
| 7  | GAS1 | chr1-3_0226 | 1617 | 0 | |
| 8  | PMR1 | chr1-4_0325 | 2775 | 0 | |
| 9  | Methionine synthase | chr2-1_0160 | 2307 | 10 | 0 |
| 10 | Sphingolipid C9-methyltransferase | chr4_0465 | 1471 | 0 | |
| 11 | DES | chr3_0939 | 1083 | 2 | 1 |
| 12 | SLD1 | chr1-1_0013 | 1629 | 0 | |
| 13 | VAC8 | chr1-4_0101 | 1671 | 0 | |
| 14 | FTR1 | chr1-4_0040 | 1098 | 0 | |
| 15 | KEX2 | chr2-1_0304 | 2334 | 0 | |
| 16 | YPS1 | chr4_0584 | 1800 | 2 | 0 |
| 17 | PRC1 | chr1-4_0013 | 1572 | 0 | |
| 18 | PDI | chr4_0844 | 1554 | 2 | 1 |
| 19 | YPT-like | chr1-4_0627 | 919 | 0 | |
| 20 | SEC4 | chr3_0143 | 615 | 0 | |
| 21 | FAD2 | chr4_0052 | 1263 | 1 | 0 |
| 22 | ALG3 | chr4_0712 | 1398 | 6 | 0 |
| 23 | EF-2 | chr2-1_0812 | 2605 | 0 | |
| 24 | PNO1 | chr1-4_0410 | 2334 | 0 | |
| 25 | GSA10 | chr2-1_0641 | 2391 | 1 | 0 |
| 26 | CBS | chr2-2_0137 | 1506 | 2 | 0 |
| 27 | ceramide glucosyltransferase | chr3_0357 | 1530 | 0 | |
| 28 | GDI1 | chr3_0531 | 1344 | 0 | |
| 29 | GSA9 | chr1-4_0555 | 3941 | 0 | |
| 30 | SEC12 | chr4_0606 | 3117 | 0 | |
| 31 | SAR1 | chr1-1_0180 | 648 | 0 | |
| 32 | SEC18 | chr3_0342 | 2277 | 7 | 0 |
| 33 | ACT1 | chr3_1169 | 1728 | 0 | |
| 34 | UGT51B1 | chr4_0167 | 3636 | 0 | |
| 35 | GSA12 | chr3_0931 | 1632 | 1 | 0 |
| 36 | GSA11 | chr1-3_0168 | 5580 | 24 | 0 |
| 37 | SEC17 | chr2-1_0644 | 936 | 7 | 0 |
| 38 | SEC13 | chr1-3_0057 | 943 | 3 | 0 |
| 39 | AOX2 promoter | chr4_0821 | 1550 | 0 | |
|    | Total length | | 70295 | | |
|    | Total differences | | | 84 | 2 |
|    | | Accuracy | | | 1/35147 bp |

TABLE 4

Nuclear tRNA genes identified in the *P. pastoris* genome
Overview of *P. pastoris* tRNA genes

| tRNA species | Anticodon | *P. pastoris* | intron | *S. cerevisiae*[1] | intron |
|---|---|---|---|---|---|
| tRNA-Ala | AGC | 5 | | 11 | |
| tRNA-Ala | UGC | 2 | | 5 | |
| tRNA-Arg | ACG | 2 | i | 6 | |
| tRNA-Arg | CCG | 1 | | 1 | |
| tRNA-Arg | CCU | 1 | | 1 | |
| tRNA-Arg | UCG | 1 | | 0 | |
| tRNA-Arg | UCU | 4 | | 11 | |
| tRNA-Ans | GUU | 4 | | 10 | |
| tRNA-Asp | GUC | 6 | | 15 | |
| tRNA-Cys | GCA | 2 | | 4 | |
| tRNA-Gln | CUG | 2 | | 1 | |
| tRNA-Gln | UUG | 3 | | 9 | |
| tRNA-Glu | CUC | 4 | | 2 | |
| tRNA-Glu | UUC | 5 | | 14 | |
| tRNA-Gly | CCC | 1 | | 2 | |
| tRNA-Gly | GCC | 5 | | 16 | |
| tRNA-Gly | UCC | 3 | | 3 | |
| tRNA-His | GUG | 3 | | 7 | |
| tRNA-Ile | AAU | 5 | | 13 | |
| tRNA-Ile | UAU | 1 | i | 2 | i |
| tRNA-Leu | AAG | 2 | | 0 | |
| tRNA-Leu | CAA | 3 | i | 10 | i |
| tRNA-Leu | CAG | 1/1 | —/i | 0 | |
| tRNA-Leu | GAG | 0 | | 1 | |
| tRNA-Leu | UAA | 1 | | 7 | |
| tRNA-Leu | UAG | 1 | i | 3 | i |
| tRNA-Lys | CUU | 5 | | 14 | |
| tRNA-Lys | UUU | 3 | i | 7 | i |
| tRNA-Met$_{initiator}$ | CAU | 2 | | 5 | |
| tRNA-Met$_{elongator}$ | CAU | 2 | i | 5 | |
| tRNA-Phe | GAA | 5 | i | 10 | i |
| tRNA-Pro | AGG | 2 | | 2 | |
| tRNA-Pro | CGG | 1 | | 0 | |
| tRNA-Pro | UGG | 4 | | 10 | i |
| tRNA-Ser | AGA | 4 | | 11 | |
| tRNA-Ser | CGA | 1 | | 1 | i |
| tRNA-Ser | GCU | 2 | i | 4 | i |
| tRNA-Ser | UGA | 2 | i | 3 | i |

TABLE 4-continued

Nuclear tRNA genes identified in the *P. pastoris* genome
Overview of *P. pastoris* tRNA genes

| tRNA species | Anticodon | *P. pastoris* | intron | *S. cerevisiae*[1] | intron |
|---|---|---|---|---|---|
| tRNA-Thr | AGU | 5 | | 11 | |
| tRNA-Thr | CGU | 1 | | 1 | |
| tRNA-Thr | UGU | 1 | | 4 | |
| tRNA-Trp | CCA | 3 | i | 6 | i |
| tRNA-Tyr | GUA | 4 | i | 8 | i |
| tRNA-Val | AAC | 5 | | 14 | |
| tRNA-Val | UAC | 1 | | 2 | |
| tRNA-Val | CAC | 1 | | 2 | |
| total | | 123 | | 274 | |
| different tRNAs | | 45 | | 42 | |

[1]Hani and Feidmann (1998) Nucleic acids Research, 26 (3) 689

TABLE 5A

Methanol pathway genes in *P. pastoris*
Overview of *P. pastoris* genes involved in methanol metabolism (shown in FIG. 3A)

| Reference | Gene | EC code | Locus id |
|---|---|---|---|
| 1 | AOX | 1.1.3.13 | chr4_0152 |
| | | | chr4_0821 |
| 2 | FLD | 1.2.1.1 | chr3_1028 |
| 3 | FGH | 3.1.2.12 | chr3_0867 |
| 4 | FDH | 1.2.1.2 | chr3_0932 |
| 5 | CAT | 1.11.1.6 | chr2-2_0131 |
| 6 | DAS | 2.2.1.3 | chr3_0832 |
| | | | chr3_0834 |
| 7 | DAK | 2.7.1.29 | chr3_0841 |
| 8 | TPI | 5.3.1.1 | chr3_0951 |
| 9 | FBA | 4.1.21.13 | chr1-1_0072 |
| | | | chr1-1_0319 |
| 10 | FBP | 3.1.3.11 | chr3_0868 |

TABLE 5B

Protein secretion pathway in *P. pastoris*
Overview of *P. pastoris* genes involved in secreted (glyco)protein post-translational processes (shown in FIG. 3B)

| Reference | Process or complex | Gene | locus id |
|---|---|---|---|
| 1 | Sec61 complex | SEC61 | chr1-3_0202 |
| | | SBH1 | chr2-2_0210 |
| | | SSS1 | chr1-1_0023 |
| 2 | OST complex | STT3 | chr1-4_0685 |
| | | " | chr1-4_0496 |
| | | SWP1 | chr1-3_0248 |
| | | WBP1 | chr2-1_0423 |
| | | OST1 | chr3_0741 |
| | | OST2 | chr2-2_0346 |
| | | OST3 | chr4_0610 |
| | | OST4 | chr2-2 62421-62516 |
| | | OST6 | chr3_1142 |
| 3 | Signal Peptidase complex | SPC1 | chr1-1_0491 |
| | | SPC2 | chr2-1_0589 |
| | | SPC3 | chr4_0874 |
| | | SEC11 | chr1-4_0187 |
| 4 | Quality control Chaperones | ROT1 | fragB_0048 |
| | | LHS1 | chr1-3_0063 |
| | | CNE1 | chr2-1_0322 |
| | | YDJ1 | chr2-2_0066 |
| | | EPS1 | chr2-1_0421 |
| | | SHR3 | chr1-3_0116 |
| | | KAR2 | chr2-1_0140 |
| | | SIL1 | chr1-1_0237 |

TABLE 5B-continued

Protein secretion pathway in *P. pastoris*
Overview of *P. pastoris* genes involved in secreted (glyco)protein
post-translational processes (shown in FIG. 3B)

| Reference | Process or complex | Gene | locus id |
|---|---|---|---|
| | Folding sensors | HTM1(MNL1) | chr3_0891 |
| | | UGGT | chr1-3_0114 |
| | | " | chr3_0929 |
| 5 | Early N-glycan processing | GLS1 | chr1-1_0215 |
| | | GLS2 | chr2-1_0778 |
| | | MNS1 | chr2-1_0753 |
| | | GTB1 | chr3_0179 |
| 6 | N-glycan precursor synthesis | SEC59 | chr2-1_0498 |
| | | ALG7 | chr2-1_0727 |
| | | ALG13 | chr1-4_0448 |
| | | ALG14 | chr3_0944 |
| | | ALG1 | chr2-1_0759 |
| | | ALG2 | c121_0002 |
| | | ALG12 | chr4_0544 |
| | | ALG11 | chr1-4_0417 |
| | | ALG3 | chr4_0712 |
| | | ALG9 | chr2-2_0036 |
| | | ALG6 | chr2-1_0549 |
| | | ALG10 | Chr1-4_0475 |
| | | ALG8 | chr3_0999 |
| 7 | O-Glycosylation | PMT1 | chr2-1_0212 |
| | | PMT2 | chr2-1_0256 |
| | | PMT3 | " |
| | | PMT4 | chr1-4_0033 |
| | | PMT5 | chr1-1_0286 |
| | | PMT6 | chr4_0777 |
| 8 | Nucleotide sugar synthesis | | |
| | GDP-Mannose synthesis | PMI40 | chr3_1115 |
| | | MPG1(PSA1) | chr3_0870 |
| | | " | chr2-1_0093 |
| | | ALG4 | chr2-2_0053 |
| | UDP-Glc synthesis | UGP1 | chr1-3_0122 |
| | | (QRI1) | chr3_0676 |
| | UDP-GlcNAc synthesis | GFA1 | chr2-1_0626 |
| | | GNA1 | chr4_0066 |
| | | PCM1 | chr1-1_0067 |
| | | QRI1/UAP1 | chr3_0676 |
| | UDP-Gal synthesis | Gal10 | chr4_0839 |
| 9 | Nucleotide sugar transport | | |
| | GDP-Mannose transport | VRG4 | chr3_0916 |
| | | GDA1 | chr4_0021 |
| | UDP-GlcNAc transport | YEA4 | chr1-3_0163 |
| | UDP-Gal transport | HUT1 | chr2-1_0692 |
| | | Pisti UDP-GalT | chr4_0810 |
| | | (VRG4) | chr3_0916 |
| | | (YEA4) | chr1-3_0163 |
| 10 | Golgi N-glycan processing | | |
| | Hyperglycosyl and core type | OCH1 | chr1-3_0251 |
| | | MNN9 | chr4_0103 |
| | | VAN1 | chr2-1_0772 |
| | | MNN10 | chr2-2_0185 |
| | | MNN11 | chr2-2_0125 |
| | | HOC1 | chr3_0620 |
| | | ANP1 | chr3_0515 |
| | | MNN2 | chr1-4_0037 |
| | | MNN5 | chr3_0370 |
| | | MNN6 | chr3_1162 |
| | | " | chr3_0215 |
| | | MNN4 | chr1-4_0409 |
| | | " | chr2-1_0718 |
| | | " | chr2-1_0706 |
| | | PNO1 | chr1-4_0410 |
| | β-Mannosyltransferase | | chr1-4_0696 |
| | | | chr4_0471 |
| | | | chr4_0450 |
| | | | chr4_0451 |
| 11 | Pro-peptidase | KEX2 | chr2-1_0304 |
| | | STE13 | chr2-2_0310 |
| | | DAP2 | chr3_0896 |
| 12 | Protease | | |
| | Aspartic-type endopeptidase | YPS1 | chr4_0584 |
| | | YPS2 | chr3_0299 |
| | | " | chr3_1157 |

TABLE 5B-continued

Protein secretion pathway in *P. pastoris*
Overview of *P. pastoris* genes involved in secreted (glyco)protein post-translational processes (shown in FIG. 3B)

| Reference | Process or complex | Gene | locus id |
|---|---|---|---|
| | | YPS3 | chr3_0303 |
| | | " | chr3_0866 |
| | | YPS7 | chr3_0394 |
| | | MKC7 | chr1-1_0379 |
| | | PEP4 | chr3_1087 |
| | Cysteine-type peptidase | ATG4 | chr1-4_0522 |
| | | GPI8 | chr4_0261 |
| | | HSP31 | chr3_0691 |
| | | HSP32 | " |
| | | HSP33 | " |
| | | SNO4 | " |

TABLE 6

Location of TATA elements in certain *Pichia pastoris* promoters.

| class | SEQ# | Site (−bp vs. ATG) | tata-type | Site (−bp vs. ATG) | tata-type |
|---|---|---|---|---|---|
| glycolyse | 60 | 23 | TACAA | | |
| | 61 | 135 | TATAA | | |
| | 62 | 143 | TATAA | | |
| | 63 | 55 | TATA | | |
| | 64 | 106 | TATAA | | |
| | 65 | 229 | TATAA | | |
| | 66 | 53 | TACAA | | |
| | 67 | 205 | TACAA | 81 | TATATA |
| | 68 | 89 | TATAA | | |
| | 69 | | | | |
| | 70 | 61 | TACAA | 24 | TATA |
| | 71 | 122 | TATAA | | |
| | 72 | 71 | TATAA | | |
| | 73 | 74/21 | TATAA | | |
| | 74 | 70 | TATAA | | |
| | 75 | 136 | TATAA | | |
| | 76 | 52 | TATATATA | | |
| | 77 | 66 | TATAA | | |
| | 78 | 68/108 | TACAA | | |
| | 79 | 117 | TATAA | | |
| | 80 | 47/106 | TATAA | | |
| | 81 | 25 | TATAA | | |
| | 82 | 82 | TATAA | | |
| | 83 | 32 | TATA | | |
| | 84 | 78 | TATAA | 72 | |
| | 85 | 112 | TATATA | 145 | TATA |
| high expression | 96 | 75 | TATAA | | |
| | 97 | 84 | TATAA | | |
| | 98 | | | | |
| | 99 | 14/78 | TATAA | 22 | TACAA |
| | 100 | | | | |
| | 101 | 87 | TATAA | | |
| | 102 | 95 | TATAA | | |
| | 103 | 29/45 | TATAA | 19 | TATA |
| | 104 | 21 | TATA | | |
| | 105 | | | | |
| | 106 | | | | |
| | 107 | 38 | TATAA | | |
| | 108 | | | | |
| | 109 | | | | |
| | 110 | | | | |
| | 111 | 21 | TATA | | |
| | 112 | | | | |
| | 113 | 76 | TATA | | |
| | 114 | 70 | TACAA | | |
| | 115 | 8 | TATATATA | | |
| | 116 | 120 | TATA | | |
| | 117 | | | | |
| | 118 | | | | |
| | 119 | 66 | TATAA | | |
| | 120 | | | | |
| | 121 | 54 | TACAA | | |
| | 122 | | | | |
| | 123 | | | | |
| | 124 | | | | |
| S. cerv | 125 | | | | |
| | 126 | 82 | TATAA | | |
| | 127 | 68 | TATAA | | |
| | 128 | 67 | TATA | | |
| MeOH | 169 | 76 | TATAA | | |
| | 170 | 50 | TATATATA | | |
| | 171 | 48 | TATAA | | |
| | 172 | 54 | TATAA | | |
| | 173 | 102 | TATAA | 45 | TACAA |
| | 174 | 61 | TACAA | 24 | TATA |
| | 175 | 34/99 | TATAA | 12 | TATA |
| | 176/65 | 229 | TATAA | | |
| | 177/66 | 53 | TACAA | | |
| | 178 | 81 | TATATA | | |
| Xyl- and Arabinose | XYL1 | 63 | TATAA | | |
| | XYL2 | | | | |
| | XYL3 | 82/91 | TATA | | |
| | RPE1 | 55 | TATATA | 48 | TATA |
| | LXR1 | | | | |

TABLE 7

Relative glycan contribution

| GlycoSwitch strain | Man5 | GnMan5 | GalGnMan5 |
|---|---|---|---|
| GnMan5 | 21.26 ± 0.52 | 78.74 ± 0.52 | |
| GnMan5::UDP-GlcNAcT | 30.52 ± 2.27 | 69.48 ± 2.27 | |
| GalGnMan5 | 19.62 ± 0.64 | 8.30 ± 0.38 | 72.08 ± 1.01 |
| GalGnMan5::UDP-GalT | 21.53 ± 1.91 | 9.49 ± 3.75 | 68.98 ± 4.69 |
| GalGnMan5::UDP-Glc-4-epi | 20.69 ± 1.72 | 9.18 ± 0.41 | 70.13 ± 1.66 |

Table shows average ± standard deviation (n = 12).

TABLE 8

| | Pichia pastoris | | | Saccharomyces cerevisiae | | | | |
|---|---|---|---|---|---|---|---|---|
| To check | Pipas annotation | Graf wild-type | Maltanovich Secreted* | Name | Newman | Ghaemmaghami | Liu (relative) | Brockmann |
| * | chr2-1__0140 | 54500 | | KAR2 | 197.0 | 336941.9 | 156.0 | 48808.8 |
| ** | chr1-1__0160/chr4__0844 | 249 | | PDI1 | 407.0 | #N/A | 195.0 | 32771.3 |
| * | chr4__0559 | | | CRH1 | 163.5 | 29521.4 | #N/A | 29521.4 |
| * | chr1-4__0426 | 120000 | * | BGL2 | | 45010.4 | 27.0 | 28279.0 |
| * | chr1-4__0013 | 16700 | | PRC1 | | 44049.8 | 21.0 | 27096.5 |
| * | chr2-1__0052 | 12100 | * | SCW11 | 127.5 | 22621.3 | #N/A | 22621.3 |
| ** | chr1-1__0267/chr4__0545 | 3260 | | CPR5 | 112.5 | #N/A | 37.0 | 13586.4 |
| ** | chr1-3__0226/chr1-3__0227 | 51600 | * | GAS1 | 6241.5 | 12359.8 | 27.0 | 11953.7 |
| * | chr1-4__0611 | 16000 | | APE3 | | 4738.8 | 70.0 | 11809.0 |
| * | chr2-2__0148 | 186000 | | PST1 | 181.0 | 11676.9 | #N/A | 11676.9 |
| | chr3__0179 | | | | 64.5 | 9755.8 | #N/A | 9755.8 |
| | chr3__1003 | 1750 | * | CTS1 | 194.0 | 6348.4 | #N/A | 6348.4 |
| | chr1-3__0229 | | * | SCW4 | 575.0 | 6185.6 | 8.0 | 6175.1 |
| | chr3__0419 | 329 | | ECM14 | | 468.4 | 26.0 | 5896.7 |
| | chr3__0299/chr4__0584 | 14900 | | YPS1 | | 5436.2 | #N/A | 5436.2 |
| | chr2-1__0454 | 46000 | * | EXG1 | 171.5 | 4277.0 | 8.0 | 5220.8 |
| | chr1-4__0037/ chr3__0370/chr3__0767 | 2300 | | MNN2 | 129.5 | 6725.3 | 1.0 | 4416.7 |
| | chr3__0107 | 977 | | CTS2 | | 3049.1 | #N/A | 3049.1 |
| | chr1-1__0147 | | | DFG5 | 343.0 | 2948.6 | #N/A | 2948.6 |
| | chr3__0120 | 1760 | | BIG1 | 64.0 | 3464.9 | 1.0 | 2786.6 |
| | FragB__0048 | | | ROT1 | 635.5 | 2360.9 | 2.0 | 2687.8 |
| | chr1-4__0242 | | | DCW1 | 403.0 | 2583.7 | #N/A | 2583.7 |
| | chr1-1__0293 | 21800 | | UTR2 | 684.0 | #N/A | 1.0 | 2108.2 |
| | chr3__0633 | 7380 | | | | 1417.9 | 1.0 | 1763.1 |
| | chr1-1__0130 | | * | | | 64.3 | 2.0 | 1539.5 |
| | chr1-4__0017 | 20.4 | | PPN1 | | 319.3 | 1.0 | 1213.8 |
| | chr1-1__0379 | | | MKC7 | | 538.4 | #N/A | 538.4 |
| | chr2-1__0156 | 1870 | | NHX1 | 121.0 | 521.1 | #N/A | 521.1 |
| | chr3__0394 | 9960 | | YPS7 | 47.0 | 148.8 | #N/A | 148.8 |
| | chr4__0305 | 4810 | | PIR1 | 538.0 | | | |
| | chr1-4__0164/chr3__0076 | 61300 | * | PRY2 | | #N/A | #N/A | #N/A |
| | chr3__0306 | 985 | | GAS2 | | #N/A | #N/A | #N/A |
| | chr3__0303/chr3__0866 | | | YPS3 | 50.5 | #N/A | #N/A | #N/A |
| | chr3__0517 | | | ZPS1 | | #N/A | #N/A | #N/A |

TABLE 9

Relationships between the sequences disclosed in association with "SEQ" designations in the specification and the sequence identifiers ("SEQ ID NO") in the Sequence Listing.

| "SEQ" Designation | Function/Property/Homology | "5' region" SEQ ID NO | "ORF" SEQ ID NO | "Downstream" SEQ ID NO | "AA" SEQ ID NO | "Peptide" SEQ ID NO |
|---|---|---|---|---|---|---|
| 0001 | Secreted protein | 1 | 2 | 3 | 4 | N/A |
| 0002 | Secreted protein | 5 | 6 | 7 | 8 | N/A |
| 0003 | Secreted protein | N/A | 9 | N/A | 10 | N/A |
| 0004 | Secreted protein | 11 | 12 | 13 | 14 | N/A |
| 0005 | Secreted protein | 15 | 16 | 17 | 18 | N/A |
| 0006 | Secreted protein | 19 | 20 | 21 | 22 | N/A |
| 0007 | Secreted protein | N/A | 23 | N/A | 24 | 25 |
| 0008 | Secreted protein | N/A | 26 | N/A | 27 | 28 |
| 0009 | Secreted protein | N/A | 29 | N/A | 30 | 31 |
| 0010 | Secreted protein | N/A | 32 | 33 | N/A | 34 |
| 0011 | Secreted protein | N/A | 35 | N/A | 36 | 37 |
| 0012 | Secreted protein | N/A | 38 | N/A | 39 | 40 |
| 0013 | Secreted protein | N/A | 41 | N/A | 42 | 43 |
| 0014 | Secreted protein | N/A | 44 | N/A | 45 | 46 |
| 0015 | Secreted protein | N/A | 47 | N/A | 48 | 49 |
| 0016 | Secreted protein | N/A | 50 | N/A | 51 | 52 |
| 0017 | Secreted protein | N/A | 53 | N/A | 54 | 55 |
| 0018 | Secreted protein | N/A | 56 | N/A | 57 | 58 |
| 0019 | Secreted protein | N/A | 59 | N/A | 60 | 61 |
| 0020 | Secreted protein | N/A | 62 | N/A | 63 | 64 |
| 0021 | Secreted protein | N/A | 65 | N/A | 66 | 67 |
| 0022 | Secreted protein | N/A | 68 | N/A | 69 | 70 |
| 0023 | Secreted protein | N/A | 71 | N/A | 72 | 73 |
| 0024 | Secreted protein | N/A | 74 | N/A | 75 | 76 |
| 0025 | Secreted protein | N/A | 77 | N/A | 78 | 79 |
| 0027 | Secreted protein | N/A | 80 | N/A | 81 | 82 |

TABLE 9-continued

Relationships between the sequences disclosed in association with "SEQ" designations in the specification and the sequence identifiers ("SEQ ID NO") in the Sequence Listing.

| "SEQ" Designation | Function/Property/Homology | "5' region" SEQ ID NO | "ORF" SEQ ID NO | "Downstream" SEQ ID NO | "AA" SEQ ID NO | "Peptide" SEQ ID NO |
|---|---|---|---|---|---|---|
| 0028 | Secreted protein | N/A | 83 | N/A | 84 | 85 |
| 0029 | Secreted protein | N/A | 86 | N/A | 87 | 88 |
| 0030 | Secreted protein | N/A | 89 | N/A | 90 | 91 |
| 0031 | Secreted protein | N/A | 92 | N/A | 93 | 94 |
| 0032 | Secreted protein | N/A | 95 | N/A | 96 | 97 |
| 0033 | Secreted protein | N/A | 98 | N/A | 99 | 100 |
| 0034 | Secreted protein | N/A | 101 | N/A | 102 | 103 |
| 0035 | Secreted protein | N/A | 104 | N/A | 105 | 106 |
| 0036 | Secreted protein | N/A | 107 | N/A | 108 | 109 |
| 0037 | Secreted protein | N/A | 110 | N/A | 111 | 112 |
| 0038 | Secreted protein | N/A | 113 | N/A | 114 | 115 |
| 0039 | Secreted protein | N/A | 116 | N/A | 117 | 118 |
| 0040 | Secreted protein | N/A | 119 | N/A | 120 | 121 |
| 0041 | Secreted protein | N/A | 122 | N/A | 123 | 124 |
| 0042 | Secreted protein | N/A | 125 | N/A | 126 | 127 |
| 0043 | Secreted protein | N/A | 128 | N/A | 129 | 130 |
| 0044 | Secreted protein | N/A | 131 | N/A | 132 | 133 |
| 0045 | Secreted protein | N/A | 134 | N/A | 135 | 136 |
| 0046 | Secreted protein | N/A | 137 | N/A | 138 | 139 |
| 0047 | Secreted protein | N/A | 140 | N/A | 141 | 142 |
| 0048 | Secreted protein | N/A | 143 | N/A | 144 | 145 |
| 0049 | Secreted protein | N/A | 146 | N/A | 147 | 148 |
| 0050 | Secreted protein | N/A | 149 | N/A | 150 | 151 |
| 0051 | Secreted protein | N/A | 152 | N/A | 153 | 154 |
| 0052 | Secreted protein | N/A | 155 | N/A | 156 | 157 |
| 0053 | Secreted protein | N/A | 158 | N/A | 159 | 160 |
| 0054 | Secreted protein | N/A | 161 | N/A | 162 | 163 |
| 0055 | Involved in secretion | 164 | 165 | 166 | 167 | N/A |
| 0056 | Involved in secretion | 168 | 169 | 170 | 171 | N/A |
| 0057 | Involved in secretion | 172 | 173 | 174 | 175 | N/A |
| 0058 | Involved in secretion | 176 | 177 | 178 | 179 | N/A |
| 0059 | Involved in secretion | 180 | 181 | 182 | 183 | N/A |
| 0060 | Homologue of gene(s) involved in the glycolysis pathway | 184 | 185 | 186 | 187 | N/A |
| 0061[1] | Homologue of gene(s) involved in the glycolysis pathway | 188 | 189 | 190 | 191 | N/A |
| 0062 | Homologue of gene(s) involved in the glycolysis pathway | 192 | 193 | 194 | 195 | N/A |
| 0063 | Homologue of gene(s) involved in the glycolysis pathway | 196 | 197 | 198 | 199 | N/A |
| 0064 | Homologue of gene(s) involved in the glycolysis pathway | 200 | 201 | 202 | 203 | N/A |
| 0065 | Homologue of gene(s) involved in the glycolysis pathway | 204 | 205 | 206 | 207 | N/A |
| 0066 | Homologue of gene(s) involved in the glycolysis pathway | 208 | 209 | 210 | 211 | N/A |
| 0067 | Homologue of gene(s) involved in the glycolysis pathway | 212 | 213 | 214 | 215 | N/A |
| 0068 | Homologue of gene(s) involved in the glycolysis pathway | 216 | 217 | 218 | 219 | N/A |
| 0069 | Homologue of gene(s) involved in the glycolysis pathway | 220 | 221 | 222 | 223 | N/A |
| 0070 | Homologue of gene(s) involved in the glycolysis pathway | 224 | 225 | 226 | 227 | N/A |
| 0071 | Homologue of gene(s) involved in the glycolysis pathway | 228 | 229 | 230 | 231 | N/A |
| 0072 | Homologue of gene(s) involved in the glycolysis pathway | 232 | 233 | 234 | 235 | N/A |
| 0073 | Homologue of gene(s) involved in the glycolysis pathway | 236 | 237 | 238 | 239 | N/A |
| 0074 | Homologue of gene(s) involved in the glycolysis pathway | 240 | 241 | 242 | 243 | N/A |
| 0075 | Homologue of gene(s) involved in the glycolysis pathway | 244 | 245 | 246 | 247 | N/A |
| 0076 | Homologue of gene(s) involved in the glycolysis pathway | 248 | 249 | 250 | 251 | N/A |
| 0077 | Homologue of gene(s) involved in the glycolysis pathway | 252 | 253 | 254 | 255 | N/A |
| 0078 | Homologue of gene(s) involved in the glycolysis pathway | 256 | 257 | 258 | 259 | N/A |
| 0079 | Homologue of gene(s) involved in the glycolysis pathway | 260 | 261 | 262 | 263 | N/A |

TABLE 9-continued

Relationships between the sequences disclosed in association with "SEQ" designations in the specification and the sequence identifiers ("SEQ ID NO") in the Sequence Listing.

| "SEQ" Designation | Function/Property/Homology | "5' region" SEQ ID NO | "ORF" SEQ ID NO | "Downstream" SEQ ID NO | "AA" SEQ ID NO | "Peptide" SEQ ID NO |
|---|---|---|---|---|---|---|
| 0080 | Homologue of gene(s) involved in the glycolysis pathway | 264 | 265 | 266 | 267 | N/A |
| 0081 | Homologue of gene(s) involved in the glycolysis pathway | 268 | 269 | 270 | 271 | N/A |
| 0082 | Homologue of gene(s) involved in the glycolysis pathway | 272 | 273 | 274 | 275 | N/A |
| 0083 | Homologue of gene(s) involved in the glycolysis pathway | 276 | 277 | 278 | 279 | N/A |
| 0084 | Homologue of gene(s) involved in the glycolysis pathway | 280 | 281 | 282 | 283 | N/A |
| 0085 | Homologue of gene(s) involved in the glycolysis pathway | 284 | 285 | 286 | 287 | N/A |
| 0086 | Homologue of gene(s) involved in the homologous recombination | 288 | 289 | 290 | 291 | N/A |
| 0087 | Homologue of gene(s) involved in the homologous recombination | 292 | 293 | 294 | 295 | N/A |
| 0088 | Homologue of gene(s) involved in the homologous recombination | 296 | 297 | 298 | 299 | N/A |
| 0089 | Homologue of gene(s) involved in the homologous recombination | 300 | 301 | 302 | 303 | N/A |
| 0090 | Homologue of gene(s) involved in the homologous recombination | 304 | 305 | 306 | 307 | N/A |
| 0091 | Homologue of gene(s) involved in the homologous recombination | 308 | 309 | 310 | 311 | N/A |
| 0092 | Homologue of gene(s) involved in the homologous recombination | 312 | 313 | 314 | 315 | N/A |
| 0093 | Homologue of gene(s) involved in the homologous recombination | 316 | 317 | 318 | 319 | N/A |
| 0094 | Homologue of gene(s) involved in the homologous recombination | 320 | 321 | 322 | 323 | N/A |
| 0095 | Homologue of gene(s) involved in the homologous recombination | 324 | 325 | 326 | 327 | N/A |
| 0096 | High expression level | 328 | 329 | 330 | 331 | N/A |
| 0097 | High expression level | 332 | 333 | 334 | 335 | N/A |
| 0098 | High expression level | 336 | 337 | 338 | 339 | N/A |
| 0099 | High expression level | 340 | 341 | 342 | 343 | N/A |
| 0100 | High expression level | 344 | 345 | 346 | 347 | N/A |
| 0101 | High expression level | 348 | 349 | 350 | 351 | N/A |
| 0102 | High expression level | 352 | 353 | 354 | 355 | N/A |
| 0103 | High expression level | 356 | 357 | 358 | 359 | N/A |
| 0104 | High expression level | 360 | 361 | 362 | 363 | N/A |
| 0105 | High expression level | 364 | 365 | 366 | 367 | N/A |
| 0106 | High expression level | 368 | 369 | 370 | 371 | N/A |
| 0107 | High expression level | 372 | 373 | 374 | 375 | N/A |
| 0108 | High expression level | 376 | 377 | 378 | 379 | N/A |
| 0109 | High expression level | 380 | 381 | 382 | 383 | N/A |
| 0110 | High expression level | 384 | 385 | 386 | 387 | N/A |
| 0111 | High expression level | 388 | 389 | 390 | 391 | N/A |
| 0112 | High expression level | 392 | 393 | 394 | 395 | N/A |
| 0113 | High expression level | 396 | 397 | 398 | 399 | N/A |
| 0114 | High expression level | 400 | 401 | 402 | 403 | N/A |
| 0115 | High expression level | 404 | 405 | 406 | 407 | N/A |
| 0116 | High expression level | 408 | 409 | 410 | 411 | N/A |
| 0117 | High expression level | 412 | 413 | 414 | 415 | N/A |
| 0118 | High expression level | 416 | 417 | 418 | 419 | N/A |
| 0119 | High expression level | 420 | 421 | 422 | 423 | N/A |
| 0120 | High expression level | 424 | 425 | 426 | 427 | N/A |
| 0121 | High expression level | 428 | 429 | 430 | 431 | N/A |
| 0122 | High expression level | 432 | 433 | 434 | 435 | N/A |
| 0123 | High expression level | 440 | 441 | 442 | 443 | N/A |
| 0124 | High expression level | 444 | 445 | 446 | 447 | N/A |
| 0125 | Homologue of promotor(s) used for expression of proteins in *S. cerevisiae* | 448 | 449 | 450 | 451 | N/A |
| 0126 | Homologue of promotor(s) used for expression of proteins in *S. cerevisiae* | 452 | 453 | 454 | 455 | N/A |
| 0127 | Homologue of promotor(s) used for expression of proteins in *S. cerevisiae* | 456 | 457 | 458 | 459 | N/A |
| 0128 | Homologue of promotor(s) used for expression of proteins in *S. cerevisiae* | 460 | 461 | 462 | 463 | N/A |
| 0129 | Involved in nucleotide sugar synthesis and transport | 464 | 465 | 466 | 467 | N/A |

TABLE 9-continued

Relationships between the sequences disclosed in association with "SEQ" designations in the specification and the sequence identifiers ("SEQ ID NO") in the Sequence Listing.

| "SEQ" Designation | Function/Property/Homology | "5' region" SEQ ID NO | "ORF" SEQ ID NO | "Downstream" SEQ ID NO | "AA" SEQ ID NO | "Peptide" SEQ ID NO |
|---|---|---|---|---|---|---|
| 0130 | Involved in nucleotide sugar synthesis and transport | 468 | 469 | 470 | 471 | N/A |
| 0131 | Involved in nucleotide sugar synthesis and transport | 472 | 473 | 474 | 475 | N/A |
| 0132 | Involved in nucleotide sugar synthesis and transport | 476 | 477 | 478 | 479 | N/A |
| 0133 | Involved in O-glycosylation | 480 | 481 | 482 | 483 | N/A |
| 0134 | Involved in O-glycosylation | 484 | 485 | 486 | 487 | N/A |
| 0135 | Involved in O-glycosylation | 488 | 489 | 490 | 491 | N/A |
| 0136 | Involved in O-glycosylation | 492 | 493 | 494 | 495 | N/A |
| 0137 | Involved in O-glycosylation | 496 | 497 | 498 | 499 | N/A |
| 0138 | Mannosyltransferase | 500 | 501 | 502 | 503 | N/A |
| 0139 | Mannosyltransferase | 504 | 505 | 506 | 507 | N/A |
| 0140 | Mannosyltransferase | 508 | 509 | 510 | 511 | N/A |
| 0141 | Mannosyltransferase | 512 | 513 | 514 | 515 | N/A |
| 0142 | Mannosyltransferase | 516 | 517 | 518 | 519 | N/A |
| 0143 | Mannosyltransferase | 520 | 521 | 522 | 523 | N/A |
| 0144 | Mannosyltransferase | 524 | 525 | 526 | 527 | N/A |
| 0145 | Mannosyltransferase | 528 | 529 | 530 | 531 | N/A |
| 0146 | Mannosyltransferase | 532 | 533 | 534 | 535 | N/A |
| 0147 | Mannosyltransferase | 536 | 537 | 538 | 539 | N/A |
| 0148 | Mannosyltransferase | 540 | 541 | 542 | 543 | N/A |
| 0149 | Mannosyltransferase | 544 | 545 | 546 | 547 | N/A |
| 0150 | Mannosyltransferase | 548 | 549 | 550 | 551 | N/A |
| 0151 | Mannosyltransferase | 552 | 553 | 554 | 555 | N/A |
| 0152 | Mannosyltransferase | 556 | 557 | 558 | 559 | N/A |
| 0153 | Involved in ER glycosylation pathway | 560 | 561 | 562 | 563 | N/A |
| 0154 | Involved in ER glycosylation pathway | 564 | 565 | 566 | 567 | N/A |
| 0155 | Involved in ER glycosylation pathway | 568 | 569 | 570 | 571 | N/A |
| 0156 | Involved in ER glycosylation pathway | 572 | 573 | 574 | 575 | N/A |
| 0157 | Involved in ER glycosylation pathway | 576 | 577 | 578 | 579 | N/A |
| 0158 | Involved in ER glycosylation pathway | 580 | 581 | 582 | 583 | N/A |
| 0159 | Involved in ER glycosylation pathway | 584 | 585 | 586 | N/A | N/A |
| 0160 | Involved in ER glycosylation pathway | 587 | 588 | 589 | 590 | N/A |
| 0161 | Involved in ER glycosylation pathway | 591 | 592 | 593 | 594 | N/A |
| 0162 | Involved in ER glycosylation pathway | 595 | 596 | 597 | 598 | N/A |
| 0163 | Involved in ER glycosylation pathway | 599 | 600 | 601 | 602 | N/A |
| 0164 | Involved in ER glycosylation pathway | 603 | 604 | 605 | 606 | N/A |
| 0165 | Involved in ER glycosylation pathway | 607 | 608 | 609 | 610 | N/A |
| 0166 | "Remaining gene of the glycosylation pathway" | 611 | 612 | 613 | 614 | N/A |
| 0167 | "Remaining gene of the glycosylation pathway" | 615 | 616 | 617 | 618 | N/A |
| 0168 | "Remaining gene of the glycosylation pathway" | 619 | 620 | 621 | 622 | N/A |
| 0169 | Involved in methanol metabolism | 623 | 624 | 625 | 626 | N/A |
| 0170 | Involved in methanol metabolism | 627 | 628 | 629 | 630 | N/A |
| 0171 | Involved in methanol metabolism | 631 | 632 | 633 | 634 | N/A |
| 0172 | Involved in methanol metabolism | 635 | 636 | 637 | 638 | N/A |
| 0173 | Involved in methanol metabolism | 639 | 640 | 641 | 642 | N/A |
| 0174 | Involved in methanol metabolism | 643 | 644 | 645 | 646 | N/A |
| 0175 | Involved in methanol metabolism | 647 | 648 | 649 | 650 | N/A |
| 0176[2] | N/A | N/A | N/A | N/A | N/A | N/A |
| 0177[3] | N/A | N/A | N/A | N/A | N/A | N/A |
| 0178 | Involved in methanol metabolism | 651 | 652 | 653 | 654 | N/A |
| 0179 | Homologue of serine-type peptidase(s) | 655 | 656 | 657 | 658 | N/A |
| 0180 | Homologue of serine-type endopeptidase inhibitor(s) | 659 | 660 | 661 | 662 | N/A |

TABLE 9-continued

Relationships between the sequences disclosed in association with "SEQ" designations in the specification and the sequence identifiers ("SEQ ID NO") in the Sequence Listing.

| "SEQ" Designation | Function/Property/Homology | "5' region" SEQ ID NO | "ORF" SEQ ID NO | "Downstream" SEQ ID NO | "AA" SEQ ID NO | "Peptide" SEQ ID NO |
|---|---|---|---|---|---|---|
| 0181 | Homologue of aspartic-type endopeptidase(s) | 663 | 664 | 665 | 666 | N/A |
| 0182 | Homologue of aspartic-type endopeptidase(s) | 667 | 668 | 669 | 670 | N/A |
| 0183 | Homologue of aspartic-type endopeptidase(s) | 671 | 672 | 673 | 674 | N/A |
| 0184 | Homologue of aspartic-type endopeptidase(s) | 675 | 676 | 677 | 678 | N/A |
| 0185 | Homologue of aspartic-type endopeptidase(s) | 679 | 680 | 681 | N/A | N/A |
| 0186 | Homologue of aspartic-type endopeptidase(s) | 682 | 683 | 684 | 685 | N/A |
| 0187 | Chaperone | 686 | 687 | 688 | 689 | N/A |
| 0188 | Chaperone | 690 | 691 | 692 | 693 | N/A |
| 0189 | Chaperone | 694 | 695 | 696 | 697 | N/A |
| 0190 | Chaperone | 698 | 699 | 700 | 701 | N/A |
| 0191 | Chaperone | 702 | 703 | 704 | 705 | N/A |
| 0192 | Chaperone | 706 | 707 | 708 | 709 | N/A |
| 0193 | Chaperone | 710 | 711 | 712 | 713 | N/A |
| 0194 | Chaperone | 714 | 715 | 716 | 717 | N/A |
| 0195 | Chaperone | 718 | 719 | 720 | 721 | N/A |
| 0196 | Chaperone | 722 | 723 | 724 | 725 | N/A |
| 0197 | Chaperone | 726 | 727 | 728 | 729 | N/A |
| 0198 | Chaperone | 730 | 731 | 732 | 733 | N/A |
| 0199 | Chaperone | 734 | 735 | 736 | 737 | N/A |
| 0200 | Chaperone | 738 | 739 | 740 | 741 | N/A |
| 0201 | 5S ribosomal RNA gene | 742 | N/A | N/A | N/A | N/A |
| 0202 | Involved in xylose metabolism | 743 | 744 | N/A | 745 | N/A |
| 0203 | Involved in xylose metabolism | 746 | 747 | N/A | 748 | N/A |
| 0204 | Involved in xylose metabolism | 749 | 750 | N/A | 751 | N/A |
| 0205 | Involved in xylose metabolism | 752 | 753 | N/A | 754 | N/A |
| 0206 | Involved in arabinose metabolism | 755 | 756 | N/A | 757 | N/A |
| 0207 | Involved in arabinose metabolism | 758 | 759 | N/A | 760 | N/A |
| 0208 | Involved in threhalose metabolism | 761 | 762 | 763 | 764 | N/A |
| 0209 | Involved in threhalose metabolism | 765 | 766 | 767 | 768 | N/A |
| 0210 | β-mannosyltransferase | 769 | 770 | 771 | 772 | N/A |
| 0211 | β-mannosyltransferase | 773 | 774 | 775 | 776 | N/A |
| 0212 | β-mannosyltransferase | 777 | 778 | 779 | 780 | N/A |

[1]These sequences (SEQ0061, or SEQ ID NOS: 188-191) are also disclosed on pages 131 to 132 of the document entitled "*P. pastoris* Sequences" in the application as filed.
[2]SEQ0176 refers to SEQ0065.
[3]SEQ0177 refers to SEQ0066.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08440456B2). An electronic copy of the "Sequence Listing" will also be available from the USPTO upon request and payment of the fee set forth in 37 CFR 1.19(b)(3).

What is claimed is:

1. An expression vector for overexpression of chaperones, comprising, from 5' to 3', a promoter, operably linked to a coding sequence as set forth in any one of SEQ ID NOS: 687, 691, 695, 699, 703, 707, 711, 715, 719, 723, 727, 731, 735, and 739, and a transcription termination sequence.

2. A collection of expression vectors, each vector in said collection comprising from 5' to 3', a promoter, operably linked to a coding sequence as set forth in any one of SEQ ID NOS: 687, 691, 695, 699, 703, 707, 711, 715, 719, 723, 727, 731, 735, and 739, and a transcription termination sequence, wherein the coding sequences in the vectors differ from one another.

3. A genetically engineered methylotrophic yeast strain, comprising an expression vector which encodes at least one chaperone set forth in any one of SEQ ID NOS: 689, 693, 697, 701, 705, 709, 713, 717, 721, 725, 729, 733, 737, and 741, wherein said expression vector is capable of overexpressing said at least one chaperone in said strain.

4. The strain of claim 3, capable of overexpressing multiple chaperones.

\* \* \* \* \*